(12) United States Patent
Wallenborg et al.

(10) Patent No.: US 11,383,012 B2
(45) Date of Patent: *Jul. 12, 2022

(54) APPARATUS FOR EXTRACORPOREAL BLOOD TREATMENT

(71) Applicant: GAMBRO LUNDIA AB, Lund (SE)

(72) Inventors: Anders Wallenborg, Bjärred (SE); Anders Nilsson, Södra Sandby (SE); Kristian Solem, Kävlinge (SE); Thomas Hertz, Lund (SE); Paolo Rovatti, Finale Emilia (IT); Carlo Alberto Lodi, Modena (IT); Alessandro Surace, Carpi (IT); Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 497 days.

This patent is subject to a terminal disclaimer.

(21) Appl. No.: 16/463,788

(22) PCT Filed: Oct. 26, 2017

(86) PCT No.: PCT/EP2017/077528
§ 371 (c)(1),
(2) Date: May 23, 2019

(87) PCT Pub. No.: WO2018/095690
PCT Pub. Date: May 31, 2018

(65) Prior Publication Data
US 2019/0275230 A1 Sep. 12, 2019

(30) Foreign Application Priority Data
Nov. 25, 2016 (SE) .................................. 1651541-3

(51) Int. Cl.
*A61M 1/34* (2006.01)
*A61M 1/16* (2006.01)
*A61M 1/36* (2006.01)

(52) U.S. Cl.
CPC ........ *A61M 1/3406* (2014.02); *A61M 1/1601* (2014.02); *A61M 1/1603* (2014.02);
(Continued)

(58) Field of Classification Search
CPC .............. A61M 1/1601; A61M 1/1603; A61M 1/1605; A61M 1/1613; A61M 1/1615;
(Continued)

(56) References Cited

U.S. PATENT DOCUMENTS

| 4,508,622 A | 4/1985 | Polaschegg et al. |
| 5,567,320 A | 10/1996 | Goux et al. |

(Continued)

FOREIGN PATENT DOCUMENTS

| CN | 103547300 | 1/2014 |
| CN | 107666919 | 2/2018 |

(Continued)

OTHER PUBLICATIONS

Chinese Search Report—Application No. 201780084751.8 dated May 24, 2021—3 pages.
(Continued)

*Primary Examiner* — John Kim
(74) *Attorney, Agent, or Firm* — K&L Gates LLP

(57) ABSTRACT

An extracorporeal blood treatment apparatus is provided comprising a filtration unit (2) connected to a blood circuit (17) and to a dialysate circuit (32), a preparation device (9) for preparing and regulating the composition of the dialysis fluid; a control unit (12) is configured for setting a sodium concentration value for the dialysis fluid in the dialysis supply line (8) at a set point; the setting of the sodium concentration includes the sub-step of calculating the sodium concentration value as an algebraic sum of a main contribution term based on the blood plasma conductivity and of an adjustment contribution term based on a concen-
(Continued)

tration of at least a substance in the dialysis fluid chosen in the group including bicarbonate, potassium, acetate, lactate, citrate, magnesium, calcium, sulphate, and phosphate.

22 Claims, 3 Drawing Sheets

(52) U.S. Cl.
CPC ........ *A61M 1/1605* (2014.02); *A61M 1/1607* (2014.02); *A61M 1/1609* (2014.02); *A61M 1/1613* (2014.02); *A61M 1/1615* (2014.02); *A61M 1/1617* (2014.02); *A61M 1/1656* (2013.01); *A61M 1/341* (2014.02); *A61M 1/342* (2013.01); *A61M 1/3403* (2014.02); *A61M 1/3413* (2013.01); *A61M 1/3424* (2014.02); *A61M 1/3431* (2014.02); *A61M 1/3434* (2014.02); *A61M 1/3437* (2014.02); *A61M 1/3455* (2013.01); *A61M 1/3462* (2013.01); *A61M 1/3465* (2014.02); *A61M 1/361* (2014.02); *A61M 1/3607* (2014.02); *A61M 1/3612* (2014.02); *A61M 1/3621* (2013.01); *A61M 1/3609* (2014.02); *A61M 2230/005* (2013.01); *A61M 2230/20* (2013.01); *A61M 2230/65* (2013.01)

(58) Field of Classification Search
CPC .. A61M 1/1617; A61M 1/3413; A61M 1/342; A61M 1/3403; A61M 1/3406; A61M 1/3424; A61M 1/3431; A61M 1/3434; A61M 1/3437; A61M 1/3455; A61M 1/3465; A61M 1/3607; A61M 1/3462; A61M 1/36; A61M 1/3612; A61M 1/361; A61M 1/3621
See application file for complete search history.

(56) References Cited

U.S. PATENT DOCUMENTS

| | | |
|---|---|---|
| 5,744,031 A | 4/1998 | Bene |
| 6,110,384 A | 8/2000 | Goux et al. |
| 6,123,847 A | 9/2000 | Bene |
| 6,126,831 A | 10/2000 | Rainer et al. |
| 6,187,199 B1 | 2/2001 | Rainer |
| 6,860,866 B1 | 3/2005 | Thomas et al. |
| 7,077,819 B1 | 7/2006 | Rainer et al. |
| 8,182,692 B2 | 5/2012 | Gotch |
| 9,199,027 B2 | 12/2015 | Fontanazzi et al. |
| 10,434,236 B2 | 10/2019 | Rovatti et al. |
| 10,828,410 B2* | 11/2020 | Nilsson .................. G01N 27/04 |
| 2008/0296226 A1 | 12/2008 | Gotch |
| 2010/0168925 A1 | 7/2010 | Hilgers et al. |
| 2012/0018379 A1 | 1/2012 | Gross et al. |
| 2013/0116650 A1 | 5/2013 | Vantard et al. |
| 2013/0274642 A1 | 10/2013 | Orhan et al. |
| 2014/0263064 A1 | 9/2014 | Jones et al. |
| 2015/0343129 A1 | 12/2015 | Surace et al. |
| 2018/0147335 A1* | 5/2018 | Nilsson ................ A61M 1/3413 |
| 2021/0015984 A1* | 1/2021 | Nilsson .................. G01R 19/22 |

FOREIGN PATENT DOCUMENTS

| | | |
|---|---|---|
| EP | 0330892 | 9/1989 |
| EP | 547025 | 6/1993 |
| EP | 0578585 | 10/1996 |
| EP | 920877 | 6/1999 |
| EP | 1104682 | 6/2001 |
| EP | 1389475 | 2/2004 |
| EP | 1395314 | 3/2004 |
| EP | 1776971 | 4/2007 |
| EP | 2377563 | 10/2011 |
| EP | 2292284 | 2/2014 |
| WO | 9855166 | 12/1998 |
| WO | 0002604 | 1/2000 |
| WO | 2005044339 | 5/2005 |
| WO | 2005063320 | 7/2005 |
| WO | 2010121805 | 10/2010 |
| WO | 2012127298 | 9/2012 |
| WO | 2012148781 | 11/2012 |
| WO | 2012172398 | 12/2012 |
| WO | 2016026569 | 2/2016 |
| WO | 2016188950 | 12/2016 |
| WO | 2016188951 | 12/2016 |
| WO | 2016188952 | 12/2016 |
| WO | 2017080969 | 5/2017 |
| WO | 2017080970 | 5/2017 |
| WO | 2018095691 | 5/2018 |
| WO | 2018095694 | 5/2018 |

OTHER PUBLICATIONS

Chinese Office Action—Application No. 201780084751.8 dated May 31, 2021—18 pages.
Goureau Y., et al. "Evaluation of Plasma Sodium Concentration During Hemodialysis By Computerization of Dialysate Conductivity", vol. 36, No. 3., Jul. 1, 1990; (4 pages).
International Search Report and Written Opinion for International Application No. PCT/EP2017/077528, dated Jan. 17, 2018; (16 pages).
Swedish Search Report for Swedish Application No. 1651541-3 dated Jul. 3, 2017; (7 pages).
Lauer, et al., "Sodium Fluxes During Hemodialysis", Trans AM Soc Artif Intern Organs (1983), vol. 29, pp. 684-687.

* cited by examiner

APPARATUS FOR EXTRACORPOREAL BLOOD TREATMENT

PRIORITY CLAIM

The present application is a National Phase of International Application No. PCT/EP2017/077528, filed Oct. 26, 2017, which claims priority to Swedish Application No. 1651541-3, filed Nov. 25, 2016, the entire contents of each of which are incorporated herein by reference and relied upon.

TECHNICAL FIELD

The present invention relates to an apparatus for extracorporeal blood treatment and a method for controlling the extracorporeal blood treatment apparatus.

In particular, the invention may be used for regulating the conductivity of a dialysis liquid during a hemodialysis a hemofiltration, or hemodiafiltration treatment.

In more detail, the apparatus and the method are particularly adapted for properly regulating the concentration of sodium in the dialysis liquid, particularly to run an isotonic or an isonatric or an isonatrikalemic dialysis treatment.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids and by the production of ammonium salts.

In individuals who have lost the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45).

In order to overcome renal dysfunction, resort is conventionally made to a blood treatment involving extracorporeal circulation through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side.

Furthermore, a pressure difference is created between the two compartments of the dialyzer which are delimited by the semipermeable membrane, so that a fraction of the plasma fluid passes by ultrafiltration through the membrane into the compartment containing the dialysis liquid.

The blood treatment which takes place in a dialyzer as regards waste from the metabolism and electrolytes results from two mechanisms of molecular transport through the membrane.

On the one hand, the molecules migrate from the liquid where their concentration is higher to the liquid where their concentration is lower. This is diffusive transport.

On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as hemodialysis).

As regards the regulation of the acid/base equilibrium inside the body, the approach adopted to overcome renal deficiency is to act on a mechanism by which the acid/base equilibrium inside the body is regulated, this mechanism consisting of the buffer systems of the blood, the main one of which comprises carbonic acid, as a weak acid, associated with its alkali salt, bicarbonate. This is why, in order to correct acidosis in a patient suffering from renal insufficiency, he is administered with bicarbonate via the vascular route, directly or indirectly, during a hemodialysis session.

Moreover, it must be underlined that sodium is the main ionic solute of extracellular volume. From literature search and according to the main opinion leaders in the dialysis field, the determination of dialysis fluid sodium concentration to be used during the dialysis treatment appears as one of the major challenges of dialysis prescription.

The dialysis fluid sodium concentration significantly affects the sodium balance and the intracellular hydration of the patient with implications on hemodialysis tolerance and also long term patient survival.

Hypertonic dialysis fluid sodium prescription will result in a positive sodium balance followed by a water shift from the intracellular to extracellular compartment. The intracellular dehydration increases vasopressin release and provokes thirst with the consequence of a greater inter-dialytic weight gain and hypertension.

On the contrary, a dialysis fluid sodium concentration that is too low (i.e., hypotonic) will provoke a negative sodium gradient with a water shift in the intracellular compartment, which is responsible for intra-dialytic cramps, headache, hypovolemia and risk of hypotension.

One of current opinions is the idea that sodium balance should be maintained null during a dialysis treatment: this is based on the so-called "sodium set point" theory, according to which both healthy subjects and dialysis patients tend to maintain a stable extra-cellular sodium concentration.

As above mentioned, sodium is removed during dialysis through convection and diffusion. The main sodium removal process during dialysis is convective. If we assume that the ultrafiltrate fluid is basically isotonic, convection does not change the tonicity of the extracellular fluid.

There is a need to help the physician to prescribe a "physiological" dialysis fluid composition to treat the patient.

Moreover, a second need is to have a bio-sensing-based therapy which is easy to use and designed also for operators not very skilled or working in crowded and very busy dialysis rooms.

To at least partly solve the above mentioned drawbacks, document U.S. Pat. No. 4,508,622 teaches a dialysis device in which the electrolyte composition of the untreated and treated fluids routed through the dialyzer may be determined and the composition of the dialysis solution adapted to the patient's requirements.

A first electrolyte detector (conductivity cell) is provided upstream of the dialyzer and a second electrolyte detector (conductivity cell) is provided downstream of the dialyzer. Each detector is coupled to a readout element through which both of the values of the dialysis solution may be observed and eventually controlled. In more detail, the apparatus according to U.S. Pat. No. 4,508,622 consists essentially of a unit for production of the dialysis solution and a dialyzer connected to the unit and followed downstream by a pump to produce a vacuum in the dialyzer on the side of the dialysis fluid. The detector mounted upstream of the dialyzer, and connected with a control unit, measures the conductivity of the total dialysis solution.

A second detector is mounted downstream of dialyzer and is connected with a comparator which is, in turn, connected to a differentiation unit. A control signal is provided by the differentiation unit to control unit if there is a difference in the differentiation unit that deviates from the predetermined nominal value.

During dialysis fluid circulation, if detector generates a signal to the evaluation unit and subsequently to the differentiation unit which deviates by a certain amount from the signal generated by detector, i.e., a difference in value appears which deviates from the predetermined value for differentiation unit, the difference unit activates the control unit, which in turn switches concentrate pump on or off as a function of the higher or lower concentration in the dialysis solution to be produced. A treatment in which the dialysis fluid has the same conductivity of the blood and of the spent dialysis fluid, is one of the described implementations.

However, the dialysis fluid and the blood reach the same conductivity after a certain time lapse which clearly affects the pre-dialytic plasma sodium content. Therefore, the method described in U.S. Pat. No. 4,508,622 in not properly an 'isoconductive' dialysis treatment.

In any case, 'isoconductive' dialysis has been shown to lead to undesired sodium loading in the patient.

Moreover, the prior art devices include dialysis apparatus wherein the conductivity of dialysis fluid is controlled in order to reach a desired post-dialysis plasmatic conductivity, i.e. conductivity (or sodium concentration) of the patient's blood at the end of the dialysis treatment.

It is known, for example from EP 1389475, a dialysis apparatus provided with a conductivity system that computes the dialysis fluid conductivity (corresponding to the dialysis fluid sodium concentration) from periodic measurements of the sodium blood concentration allowing the sodium level of the patient to reach a prescribed end-of-session value.

This dialysis apparatus includes a bag and a pump for infusing a patient with an infusion solution containing sodium at a determined and known concentration.

A structure for determining the sodium concentration $[Na^+]_{dial}$ of the dialysis liquid is also provided so that the patient's body tends towards a desired sodium concentration $[Na^+]_{des}$, as a function of the dialysance D for sodium of the dialyser, of the desired sodium concentration $[Na^+]_{des}$ inside the patient's body, of the infusion flow rate and of the sodium concentration $[Na^+]_{sol}$ of the infusion solution.

A control unit drives the pump for regulating the sodium concentration of the dialysis liquid such that this concentration is equal (tends towards) to the determined concentration $[Na^+]_{dial}$.

As previously mentioned, one of the problems of the dialysis apparatus of the discussed prior art is presently the choice of the appropriate post-dialysis plasmatic conductivity target.

EP 2377563 discloses a dialysis apparatus comprising a blood treatment unit with an online preparation device for preparing a dialysis fluid containing sodium and comprising a dialysis preparation section for regulating the concentration of sodium in the dialysis fluid. The blood circuit is configured to circulate extracorporeal blood through the blood chamber; control means determines a value representative of the sodium concentration in the blood and are programmed for driving the dialysis preparation section as a function of the determined plasma sodium value, such that the substance concentration in the dialysis fluid tends towards the substance concentration in the blood.

The plasma sodium content is determined by measuring the inlet and outlet conductivities of the dialysis fluid upstream and downstream the dialyzer, by then changing the conductivity upstream the filter by a prefixed step and measuring a second time the inlet and outlet conductivities of the dialysis fluid upstream and downstream the dialyzer with the modified conductivity value.

With the methods described, for example in EP 547025 or in EP 920877, it is possible to determine the plasma conductivity and thereby to properly regulate the dialysis fluid preparation section.

The described system however changes the blood conductivity and tonicity since the dialysis fluid enters into contact and exchange significantly with blood before a plasma conductivity calculation; the effect on plasma conductivity is in an amount proportional to the difference between blood and dialysis fluid conductivities.

Finally, document U.S. Pat. No. 8,182,692 describes a dialysis apparatus providing a treatment in which a dialysis fluid having a sodium concentration substantially equal to the estimated current sodium concentration in the patient's blood is performed by placing the dialysis fluid in communication with the patient's blood across the semi-permeable membrane to perform a dialysis treatment on the patient's blood without substantially altering the sodium concentration of the patient's blood during the performance of the dialysis treatment.

In more detail, a solution supply device, containing a conductivity-testing solution, is selectively placed in communication with dialyzer and the blood flowing therein.

According to this patent, any subject, including hemodialysis patients, has a set level of sodium in his body, referred to as the "set point." The set point of a subject tends to remain relatively constant, and sodium levels deviating too far from the set point may cause discomfort to the subject. Given the above, the method of the prior art includes causing blood to flow through blood conduit of the dialyzer and flowing the conductivity-testing solution in the opposite direction through the dialyzer.

Conductivity detectors measure the conductivity of conductivity-testing solution as the solution enters and exits dialyzer. Conductivity-testing solution is formulated such that electrically conductive solutes other than sodium in the patient's blood have little or no effect on the conductivity measurements of conductivity-testing solution.

According to U.S. Pat. No. 8,182,692, due to the closely matched concentrations of electrically conductive solutes, such as phosphate, sulfate, bicarbonate, potassium, calcium, and magnesium, in conductivity-testing solution and in the patient's blood, little diffusion of those electrically conductive solutes occurs across membrane. Consequently, the conductivity measurements of conductivity-testing solution is closely correlated with the level of sodium in the patient's blood.

Therefore, conductivity-testing solution is exclusively used to accurately determine the level of sodium in the patient's blood as a function of the change in conductivity across dialyzer of the conductivity-testing solution.

Control unit then determines the level of sodium in the patient's blood as a function of the measured conductivity values.

After determining the concentration of sodium in the patient's blood, dialysis fluid may be prepared to include a concentration of sodium that is substantially equal to the concentration of sodium determined to exist in the patient's blood.

Moreover, US2012/018379 discloses an apparatus and a method for the determination and regulation of the concentration of one dissolved substance (e.g. sodium) in a dialysis fluid circuit of a hemodialysis machine.

The user presets the sodium regulation range before the start of the dialysis using an estimated value for the dialysis fluid sodium required to achieve the isonatric state or a lab measurement of the patient sodium or a value determined by the regulation from earlier treatments. In addition, the distribution volume of the patient is input for the application of the model for the correction of the diffusive balance. Furthermore, the initial concentrations of bicarbonate and potassium in the patient are set. They come from an analysis by means of a blood gas analyzer before the start of the dialysis treatment.

After the start of the treatment, the dialysis fluid flow and the conductivity are determined upstream and downstream of the dialyzer and a calculation of the updated current bicarbonate and potassium concentration in the patient takes place with it being assumed that the potassium clearance corresponds to the sodium clearance and that the bicarbonate clearance corresponds to 70% of the sodium clearance. The sodium clearance from the blood flow is estimated until the presence of the first clearance measurement.

The calculation of the conductivity balance and of the correction term for the ion exchange and thus for the sodium balance then takes place from these data.

The conductivity of fluids measured upstream and downstream, the sodium balance and the correction term for the dialysate conductivity downstream of the dialyzer are then the input values for the sodium regulation. The desired conductivity thus determined is finally converted into a desired value for the dialysis fluid sodium while taking account of the composition of the dialysis concentrate and this preset value is transmitted to a metering unit for dialysis fluid preparation.

SUMMARY

An aim of the present invention is providing an extracorporeal blood treatment apparatus able to automatically perform a proper setting of the dialysis fluid content of a substance, particularly an ionic substance, present in the blood as well.

In detail it is an aim of the present invention to provide an extracorporeal blood treatment apparatus with a proper tool helping the physician to prescribe a "physiological" dialysis fluid composition, particularly to run an isotonic, isonatric or isonatrikalemic dialysis treatment.

A further aim of the invention is to make available an extracorporeal blood treatment apparatus provided with a selectable biosensing-based therapy which is easy to use and designed for not skilled operators or users working in crowded and busy dialysis rooms.

It is an object to provide an extracorporeal blood treatment apparatus configured to run an isotonic, isonatric or isonatrikalemic dialysis treatment in any of hemodialysis (HD), hemofiltration (HF) and hemodiafiltration (HDF) treatment modes.

It is an aim of the invention to provide an extracorporeal blood treatment machine configured to automatically perform a proper automatic setting of the dialysis fluid conductivity.

A further aim of the invention is to make available a dialysis apparatus able to provide an automated delivery and control of the dialysis prescription, particularly in order to restore at each dialysis session the proper sodium-water equilibrium to the patient.

At least one of the above-indicated aims is attained by an apparatus and a corresponding method as in one or more of the appended claims, taken singly or in any combination.

According to a first independent aspect of the invention an extracorporeal blood treatment device is provided including:
- a filtration unit (2) having a primary chamber (3) and a secondary chamber (4) separated by a semi-permeable membrane (5);
- a blood withdrawal line (6) connected to an inlet of the primary chamber (3);
- a blood return line (7) connected to an outlet of the primary chamber (3), said blood lines being configured for connection to a patient cardiovascular system;
- a dialysis supply line (8) including at least an infusion line (39) connected to said blood circuit, optionally connected to an inlet of the secondary chamber (4);
- a dialysis effluent line (13) connected to an outlet of the secondary chamber (4);
- a preparation device (9) for preparing a dialysis fluid connected to said supply line (8) and comprising regulating means (10) for regulating the composition of the dialysis fluid;
- a control unit (12) configured to run at least a hemofiltration treatment (HF) or a hemodiafiltration treatment (HDF), each of said treatment including an infusion of substitution fluid through said infusion line (39), the control unit (12) being connected to the regulating means (10) and programmed for receiving a value representative of a first parameter, the first parameter being chosen in the group including a plasma conductivity, a plasma conductivity-related parameter, a concentration of at least a substance in the blood, a concentration-related parameter of at least a substance in the blood, in particular an amount removed or added of at least a substance too; wherein said control unit (12) is configured for setting a second parameter value for the dialysis fluid in the dialysis supply line (8) at a set point, said second parameter of the dialysis fluid being at least one chosen in a group including a conductivity of the dialysis fluid, a conductivity-related parameter of the dialysis fluid, a concentration of at least a substance in the dialysis fluid and a concentration-related parameter of at least a substance in the dialysis fluid;
- wherein the setting of the second parameter value in the dialysis fluid includes the sub-step of calculating the parameter value as a function of a main contribution term based on the first parameter and as a function of an adjustment contribution term based on a concentration of at least a substance in the dialysis fluid chosen in the group including bicarbonate, potassium, acetate, lactate, citrate, magnesium, calcium, sulphate, and phosphate.

In a further independent aspect, an apparatus for extracorporeal blood treatment is provided comprising:
- a filtration unit (2) having a primary chamber (3) and a secondary chamber (4) separated by a semi-permeable membrane (5);

a blood withdrawal line (6) connected to an inlet of the primary chamber (3);
a blood return line (7) connected to an outlet of the primary chamber (3), said blood lines being configured for connection to a patient cardiovascular system;
a dialysis effluent line (13) connected to an outlet of the secondary chamber (4);
a control unit (12) configured to run at least a hemofiltration treatment (HF) or a hemodiafiltration treatment (HDF), each of said treatment including an infusion of substitution fluid through said infusion line (39), the control unit (12) being programmed for receiving a value representative of a parameter of the blood in said blood lines (6, 7), the blood parameter being chosen in the group including a plasma conductivity, a plasma conductivity-related parameter, wherein said control unit (12) is configured for:
   calculating a parameter value, said parameter value being chosen in a group including a concentration of at least a substance in the blood and a concentration-related parameter of at least a substance in the blood; wherein the calculating the parameter value is performed as a function of a main contribution term based on the blood parameter and as a function of an adjustment contribution term based on a concentration of at least a substance in the dialysis fluid chosen in the group including bicarbonate, potassium, acetate, lactate, citrate, magnesium, calcium, sulphate, and phosphate;
   storing said parameter value in a memory connected to the control unit (12), in particular the parameter value is the plasma sodium concentration.

In a further independent aspect a method for setting parameters in an apparatus for extracorporeal blood treatment is provided, the apparatus comprising:
a filtration unit (2) having a primary chamber (3) and a secondary chamber (4) separated by a semi-permeable membrane (5);
a blood withdrawal line (6) connected to an inlet of the primary chamber (3);
a blood return line (7) connected to an outlet of the primary chamber (3), said blood lines being configured for connection to a patient cardiovascular system;
a dialysis supply line (8) including at least an infusion line (39) connected to said blood circuit, optionally connected to an inlet of the secondary chamber (4);
a dialysis effluent line (13) connected to an outlet of the secondary chamber (4);
a preparation device (9) for preparing a dialysis fluid connected to said supply line (2) and comprising regulating means (10) for regulating the composition of the dialysis fluid;
a control unit (12) configured to run at least a hemofiltration treatment (HF) or a hemodiafiltration treatment (HDF), each of said treatment including an infusion of substitution fluid through said infusion line (39), the control unit (12) being connected to the regulating means (10) and programmed for receiving a value representative of a parameter of the blood in said blood lines (6, 7), the blood parameter being chosen in the group including a plasma conductivity, a plasma conductivity-related parameter, a concentration of at least a substance in the blood, a concentration-related parameter of at least a substance in the blood, the method comprising the following steps performed by the control unit:
   setting a parameter value for the dialysis fluid in the dialysis supply line (8) at a set point, said parameter of the dialysis fluid being at least one chosen in a group including a conductivity of the dialysis fluid, a conductivity-related parameter of the dialysis fluid, a concentration of at least a substance in the dialysis fluid and a concentration-related parameter of at least a substance in the dialysis fluid;
wherein the setting of the parameter value in the dialysis fluid includes the sub-step of calculating the parameter value as a function of a main contribution term based on the blood parameter and as a function of an adjustment contribution term based on a concentration of at least a substance in the dialysis fluid chosen in the group including bicarbonate, potassium, acetate, lactate, citrate, magnesium, calcium, sulphate, and phosphate.

In a $2^{nd}$ aspect according to anyone of the previous aspects, the control unit is configured to calculate the adjustment contribution term based on the concentration of two or more substances in the dialysis fluid chosen in the group including bicarbonate, potassium, acetate, lactate, citrate, magnesium, calcium, sulphate, and phosphate, in particular as a function of the concentration of at least three of said substances, optionally as a function of the concentration of bicarbonate, potassium, acetate, and/or citrate, in the dialysis fluid.

In a $3^{rd}$ aspect according to anyone of the previous aspects, the control unit is configured to calculate the adjustment contribution term as a function of the difference, in particular a weighted difference, in concentration of at least a substance in the dialysis fluid and the same substance in the blood plasma, wherein for HDF pre-dilution treatment and HF pre-dilution treatment, said plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $4^{th}$ aspect according to anyone of the previous aspects, the control unit is configured to calculate the adjustment contribution term as a function of the difference, in particular a weighted difference, in concentration of at least a substance in the dialysis fluid and the same substance in the plasma, said substance being chosen in the group including bicarbonate, potassium, acetate, lactate, and citrate, in particular as a function of the difference, in particular a weighted difference, in concentration of at least two of said substances, optionally as a function of the difference, in particular a weighted difference, in concentration of bicarbonate, potassium, and acetate in the dialysis fluid and plasma, even more optionally as a function of the difference, in particular a weighted difference, in concentration of bicarbonate, potassium, citrate, and acetate in the dialysis fluid and plasma, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a 5th aspect according to anyone of the previous aspects, the blood parameter is the plasma conductivity, or the concentration of at least a substance in the blood, said substance being in particular sodium.

In a 6th aspect according to anyone of the previous aspects, the parameter of the dialysis fluid is the conductivity of the dialysis fluid, or the concentration of at least a substance in the dialysis fluid, said substance being in particular sodium.

In a 7th aspect according to anyone of the previous aspects, the blood parameter is the plasma conductivity and the parameter of the dialysis fluid is the conductivity of the dialysis fluid.

In a 8th aspect according to anyone of the previous aspects, the blood parameter is the concentration of at least a substance in the blood, said substance being in particular sodium, and wherein the parameter of the dialysis fluid is the concentration of at least a substance in the dialysis fluid, said substance being in particular sodium.

In a 9th aspect according to the previous aspect, the blood parameter is the concentration of at least a substance in the blood, and wherein the parameter of the dialysis fluid is the concentration of at least the same substance in the dialysis fluid.

In a 10th aspect according to anyone of the previous aspects, the main contribution term is dimensionally a concentration of a substance in a fluid.

In a 11th aspect according to the previous aspect, the main contribution term is a dialysis fluid concentration of sodium at an isoconductive dialysis.

In a 12th aspect according to anyone of the previous aspects, the main contribution term affects the dialysis fluid parameter value for at least 80% of the parameter value, the adjustment contribution term contributes to the dialysis fluid parameter value for less than 20% of the parameter value, in particular the main contribution term affecting the dialysis fluid parameter value for at least 90% of the parameter value, the adjustment contribution term contributing to the dialysis fluid parameter value for less than 10% of the parameter value.

In a 13th aspect according to anyone of the previous aspects, the sub-step of calculating the parameter value as a function of the main contribution term and the adjustment contribution term is a sub-step of calculating an algebraic sum of at least the main contribution term and the adjustment contribution term and particularly wherein the adjustment contribution term is dimensionally a concentration of a substance in a fluid.

In a 14th aspect according to the previous aspect, the adjustment contribution term is the sodium concentration set point adjustment relative to an isoconductive dialysis to provide a treatment chosen in the group including isotonic dialysis, isonatric dialysis and isonatrikalemic dialysis.

In a 15th aspect according to anyone of the previous aspects, the plasma conductivity related parameter is a parameter representative of an isoconductive dialysis.

In a 16th aspect according to anyone of the previous aspects, the control unit drives the regulating means (10) for regulating the conductivity or the concentration of at least a substance in the dialysis fluid, the control unit setting the second parameter value for the dialysis fluid in the dialysis supply line (8) at the calculated set point.

In a 17th aspect according to the previous aspect, the regulating means (10) regulates the concentration of at least a substance in the dialysis fluid, in particular an ionic substance, such as sodium.

In a 18th aspect according to the previous aspect, the control unit drives the regulating means (10) for regulating the sodium concentration in the dialysis fluid to set the parameter value for the dialysis fluid in the dialysis supply line (8) at the calculated set point.

In a 19th aspect according to anyone of the previous aspects, the control unit is configured to calculate the adjustment contribution term as a function of the molar conductivities of at least a substance in the dialysis fluid chosen in the group including sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$), in particular as a function of the molar conductivities of at least two of said substances, in more detail as a function of the molar conductivities of at least three of said substances, optionally as a function of the molar conductivities of sodium bicarbonate ($NaHCO_3$), sodium chloride (NaCl), sodium acetate ($NaCH_3COO$), and/or trisodium citrate ($Na_3C_6H_5O_7$), and potassium chloride (KCl).

In a 20th aspect according to anyone of the previous aspects, the control unit is configured to calculate the adjustment contribution term as a function of a difference between two molar conductivities.

In a 21st aspect according to anyone of the previous aspects, the control unit is configured to calculate the adjustment contribution term as a function of a difference between a first molar conductivity of a substance chosen in the group including sodium bicarbonate ($NaHCO_3$), sodium acetate ($NaCH_3COO$), trisodium citrate ($Na_3C_6H_5O_7$), sodium lactate ($NaC_3H_5O_3$), potassium chloride (KCl), and a molar conductivity of sodium chloride (NaCl).

In a 22nd aspect according to anyone of the previous aspects, the control unit is configured to calculate the adjustment contribution term as a function of a difference between a molar conductivity of sodium bicarbonate ($NaHCO_3$), and a molar conductivity of sodium chloride (NaCl).

In a 23rd aspect according to anyone of the previous aspects, the control unit is configured to calculate the adjustment contribution term as a function of a difference between a molar conductivity of sodium acetate ($NaCH_3COO$), and a molar conductivity of sodium chloride (NaCl).

In a 24th aspect according to anyone of the previous aspects, the control unit is configured to calculate the adjustment contribution term as a function of a difference between a molar conductivity of trisodium citrate ($Na_3C_6H_5O_7$), and a molar conductivity of sodium chloride (NaCl).

In a 25th aspect according to anyone of the previous aspects, the control unit is configured to calculate the adjustment contribution term as a function of a difference between a molar conductivity of potassium chloride (KCl), and a molar conductivity of sodium chloride (NaCl).

In a 26th aspect according to anyone of the previous aspects, the control unit is configured to calculate the adjustment contribution term as a function of an estimated or measured plasma water concentration of at least a substance chosen in the group including bicarbonate, potassium, acetate, lactate and citrate, in particular as a function of the estimated or measured plasma water concentration of at least two of said substances, in more detail as a function of the estimated plasma water concentration of at least three of said substances, optionally as a function of the estimated plasma water concentration of bicarbonate, potassium, citrate, and acetate, in particular for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $27^{th}$ aspect according to the previous aspect, the estimated plasma water concentration of at least a substance chosen in the group including bicarbonate, potassium, citrate, and acetate is the mean pre-dialysis values of the corresponding substance for large patient populations or historical data of the corresponding substance for the individual patient or theoretical values of the corresponding substance or measured values of the corresponding substance.

In a $28^{th}$ aspect according to anyone of the previous aspects $26^{th}$ and $27^{th}$, the estimated plasma water concentration is adjusted by a respective fixed adjusting factor taking account of the Donnan effect.

In a $29^{th}$ aspect according to anyone of the previous aspects, the control unit is configured to calculate the adjustment contribution term as an algebraic sum of at least two components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma, in particular for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $30^{th}$ aspect according to anyone of the previous aspects, the control unit is configured to calculate the adjustment contribution term as an algebraic sum of at least three components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma, the third component being function of the difference, in particular a weighted difference, in concentration of at least a third substance in the dialysis fluid and the same third substance in the blood plasma, optionally a fourth component being function of the difference, in particular a weighted difference, in concentration of at least a fourth substance in the dialysis fluid and the same fourth substance in the blood plasma, in particular for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $31^{st}$ aspect according to anyone of the previous aspects, the control unit is configured to calculate the adjustment contribution term as an algebraic sum of at least two components, a first component being function of a concentration of at least a substance in the dialysis fluid and/or in the blood plasma, a second component being function of a concentration of at least a second substance in the dialysis fluid and/or in the blood plasma, in particular for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $32^{nd}$ aspect according to anyone of the previous aspects, the control unit is configured to calculate the adjustment contribution term as an algebraic sum of at least three components, a first component being function of a concentration of at least a substance in the dialysis fluid and/or in the blood plasma, a second component being function of a concentration of at least a second substance in the dialysis fluid and/or in the blood plasma, a third component being function of a concentration of at least a third substance in the dialysis fluid and/or in the blood plasma, optionally a fourth component being function of a concentration of at least a fourth substance in the dialysis fluid and/or in the blood plasma, in particular for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $33^{rd}$ aspect according to anyone of the previous aspects $29^{th}$ to $32^{nd}$, said substance is chosen in the group including bicarbonate anions ($HCO_3^-$), acetate anions ($CH_3COO^-$), citrate anions ($C_6H_5O_7^{3-}$), and potassium ions ($K^+$).

In a $34^{th}$ aspect according to anyone of the previous aspects, the control unit is configured to calculate the adjustment contribution term as a function of at least one flow rate, in particular the dialysate flow rate at the outlet of the secondary chamber (4).

In a $35^{th}$ aspect according to anyone of the previous aspects, the control unit is configured to calculate the adjustment contribution term as a function of at least an efficiency parameter of the filtration unit (2), in particular a clearance of the filtration unit (2), optionally the urea clearance.

In a $36^{th}$ aspect according to anyone of the previous aspects, the control unit is configured to calculate the adjustment contribution term as a function of at least a ratio between one flow rate, in particular the dialysate flow rate at the outlet of the secondary chamber (4), and an efficiency parameter of the filtration unit (2), in particular a clearance of the filtration unit (2), optionally the urea clearance.

In a $37^{th}$ aspect according to anyone of the previous aspects, the control unit is configured to calculate the adjustment contribution term as an algebraic sum of at least two, and particularly three or four or five, components, one component being function of at least a ratio between one flow rate, in particular the dialysate flow rate at the outlet of the secondary chamber (4), and an efficiency parameter of the filtration unit (2), in particular a clearance of the filtration unit (2), optionally the urea clearance.

In a 38$^{th}$ aspect according to anyone of the previous aspects, the control unit (12) is programmed for calculating said value representative of the parameter of the blood in said blood lines.

In a 39$^{th}$ aspect according to anyone of the previous aspects, the control unit (12) is programmed for receiving as an input said value representative of the parameter of the blood in said blood lines.

In a 40$^{th}$ aspect according to anyone of the previous aspects, the control unit (12) is programmed for storing in a memory said value representative of the parameter of the blood in said blood lines, said value representative of the parameter of the blood being not calculated by the control unit.

In a 41$^{st}$ aspect according to anyone of the previous aspects, the adjustment contribution term has a negative value.

In a 42$^{nd}$ aspect according to anyone of the previous aspects, the adjustment contribution term is a function of a rest term ($\kappa_{rest1}$; $\kappa_{rest2}$; $\kappa_{rest3}$), said rest term being a conductivity contribution from lesser solutes, in particular said lesser solutes being different from sodium, potassium, bicarbonate, and acetate, optionally said lesser solutes being different from sodium, potassium, citrate, bicarbonate, and acetate.

In a 43$^{rd}$ aspect according to anyone of the previous aspects, for a HDF pre-dilution treatment mode and/or for a HF pre-dilution treatment mode, the adjustment contribution term is:

$$c_{di,Na,isotonic,adj} = -\frac{1}{M_{\kappa_{NaCl}}}\left((M_{\kappa_{NaHCO_3}} - M_{\kappa_{NaCl}})\right. \quad (I)$$

$$\left(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\right) ++$$

$$(M_{\kappa_{NaAc}} - M_{\kappa_{NaCl}})$$

$$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right) ++$$

$$(M_{\kappa_{KCl}} - M_{\kappa_{NaCl}}) \cdot$$

-continued $$\left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right) ++ \frac{K_{b,Cit}}{K_u} \cdot$$

$$(M_{\kappa_{Na_3Cit}} - M_{\kappa_{NaCl}})\left((0.167\alpha_{bi}^{-3} + 0.125\alpha_{bi}^{-2} + 0.706\alpha_{bi}^{-1}) \cdot \cdot \right.$$

$$\left. \frac{Q_b \cdot f_{Cit} \cdot c_{pw,artCit} + Q_{inf} \cdot c_{di,Cit}}{Q_b \cdot f_{Cit} \cdot Q_{Cit}} - \right.$$

$$\left. c_{di,Na_3Cit}\right) ++ \frac{Q_{do}}{K_u}(\kappa_{rest1} + \kappa_{rest2})$$

wherein:

in HF treatment mode, the clearance being equal to the dialyzer outlet flow, i.e. $K_u = Q_{do}$;

$$\frac{Q_b \cdot f_{HCO_3} \cdot c_{pw,artHCO_3} + Q_{inf} \cdot c_{di,HCO_3}}{Q_b \cdot f_{HCO_3} + Q_{inf}}$$

is a diluted plasma water concentration of bicarbonate in blood entering the filtration unit;

$$\frac{Q_b \cdot f_{Ac} \cdot c_{pw,artAc} + Q_{inf} \cdot c_{di,Ac}}{Q_b \cdot f_{Ac} + Q_{inf}}$$

is a diluted plasma water concentration of acetate in blood entering the filtration unit;

$$\frac{Q_b \cdot f_K \cdot c_{pw,artK} + Q_{inf} \cdot c_{di,K}}{Q_b \cdot f_K + Q_{inf}}$$

is a diluted plasma water concentration of potassium in blood entering the filtration unit;

$$\frac{Q_b \cdot f_{Cit} \cdot c_{pw,artCit} + Q_{inf} \cdot c_{di,Cit}}{Q_b \cdot f_{Cit} \cdot Q_{Cit}}$$

is a diluted plasma water concentration of citrate in blood entering the filtration unit;

| | |
|---|---|
| $c_{di, Na, set, isotonic, adj}$ | Sodium set point adjustment (relative to isoconductive state) required to provide isotonic dialysis; |
| $M_{\kappa, NaHCO_3}$ | Molar conductivity of sodium bicarbonate (NaHCO$_3$); |
| $M_{\kappa, NaCl}$ | Molar conductivity of sodium chloride (NaCl); |
| $M_{\kappa, NaAc}$ | Molar conductivity of sodium acetate (NaCH$_3$COO); |
| $M_{\kappa, KCl}$ | Molar conductivity of potassium chloride (KCl); |
| $M_{\kappa, Na_3Cit}$ | Molar conductivity of trisodium citrate (Na$_3$C$_6$H$_5$O$_7$) at ionic strength 150 mM; |
| $\kappa_{rest1}$ | Conductivity contribution from lesser solutes 1; |
| $\kappa_{rest2}$ | Conductivity contribution from lesser solutes 2; |
| $c_{di, HCO_3}$ | Dialysis fluid concentration of bicarbonate as set by the operator; |
| $c_{di, K}$ | Dialysis fluid concentration of potassium ions (K$^+$) as determined by the used concentrate; |
| $c_{di, Ac}$ | Dialysis fluid concentration of acetate as determined by the used concentrate; |
| $c_{di, Na_3Cit}$ | Dialysis fluid concentration of total citrate as determined by the used concentrate; |

| | |
|---|---|
| $Q_{do}$ | Dialysate flow rate at filtration unit outlet (i.e., $Q_{di} + Q_{uf}$); |
| $K_u$ | Filtration unit clearance for urea; |
| $K_{b,\,Cit}$ | Filtration unit clearance for citrate; |
| $\alpha_{bi}$ | Donnan factor in HF/HDF pre-dilution mode; |

In a 44$^{th}$ aspect according to anyone of the previous aspects 1$^{st}$ to 42$^{nd}$, for a HDF pre-dilution treatment mode and/or for a HF pre-dilution treatment mode, the adjustment contribution term is (formula II):

$$c_{di,Na,isoNa,adj} = -\frac{1}{M_{\kappa_{NaCl}}}\left(\left(M_{\kappa_{NaHCO_3}} - M_{\kappa_{NaCl}}\right)\right.$$

$$\left(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\right) + +$$

$$\left(M_{\kappa_{NaAc}} - M_{\kappa_{NaCl}}\right)$$

$$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right) + +$$

$$M_{\kappa_{KCl}} \cdot \left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right) + +$$

$$\frac{K_{b,Cit}}{K_u} \cdot \left(M_{\kappa_{Na_3Cit}} - M_{\kappa_{NaCl}}\right)$$

$$\left(\left(0.167\alpha_{bi}^{-3} + 0.125\alpha_{bi}^{-2} + 0.706\alpha_{bi}^{-1}\right)\cdot\cdot\right.$$

$$\frac{Q_b \cdot f_{Cit} \cdot c_{pw,artCit} + Q_{inf} \cdot c_{di,Cit}}{Q_b \cdot f_{Cit} \cdot Q_{Cit}} -$$

$$\left.\left.c_{di,Na_3Cit}\right)\right) + + \frac{Q_{do}}{K_u} \kappa_{rest3}$$

wherein:

in HF treatment mode, the clearance being equal to the dialyzer outlet flow, i.e.

$$K_u = \frac{Q_b \cdot f_{HCO_3} \cdot c_{pw,artHCO_3} + Q_{inf} \cdot c_{di,HCO_3}}{Q_b \cdot f_{HCO_3} + Q_{inf}}$$

$Q_{do}$;

is a diluted plasma water concentration of bicarbonate in blood entering the filtration unit;

$$\frac{Q_b \cdot f_{Ac} \cdot c_{pw,artAc} + Q_{inf} \cdot c_{di,Ac}}{Q_b \cdot f_{Ac} + Q_{inf}}$$

is a diluted plasma water concentration of acetate in blood entering the filtration unit;

$$\frac{Q_b \cdot f_K \cdot c_{pw,artK} + Q_{inf} \cdot c_{di,K}}{Q_b \cdot f_K + Q_{inf}}$$

is a diluted plasma water concentration of potassium in blood entering the filtration unit;

$$\frac{Q_b \cdot f_{Cit} \cdot c_{pw,artCit} + Q_{inf} \cdot c_{di,Cit}}{Q_b \cdot f_{Cit} + Q_{inf}}$$

is a diluted plasma water concentration of citrate in blood entering the filtration unit;

| | |
|---|---|
| $c_{di,\,Na,\,set,\,isoNa,\,adj}$ | Sodium set point adjustment (relative to isoconductive state) required to provide isonatric dialysis; |
| $M_{\kappa,\,NaHCO_3}$ | Molar conductivity of sodium bicarbonate (NaHCO$_3$); |
| $M_{\kappa,\,NaCl}$ | Molar conductivity of sodium chloride (NaCl); |
| $M_{\kappa,\,NaAc}$ | Molar conductivity of sodium acetate (NaCH$_3$COO); |
| $M_{\kappa,\,KCl}$ | Molar conductivity of potassium chloride (KCl); |
| $M_{\kappa,\,Na_3Cit}$ | Molar conductivity of trisodium citrate (Na$_3$C$_6$H$_5$O$_7$) at ionic strength 150 mM; |
| $\kappa_{rest3}$ | Conductivity contribution from lesser solutes 3; |
| $c_{di,\,HCO_3}$ | Dialysis fluid concentration of bicarbonate as set by the operator; |
| $c_{di,\,K}$ | Dialysis fluid concentration of potassium ions (K$^+$) as determined by the used concentrate; |
| $c_{di,\,Ac}$ | Dialysis fluid concentration of acetate as determined by the used concentrate; |
| $c_{di,\,Na_3Cit}$ | Dialysis fluid concentration of total citrate as determined by the used concentrate; |
| $Q_{do}$ | Dialysate flow rate at filtration unit outlet (i.e., $Q_{di} + Q_{uf}$); |
| $K_u$ | Filtration unit clearance for urea; |
| $K_{b,\,Cit}$ | Filtration unit clearance for citrate; |
| $\alpha_{bi}$ | Donnan factor in HF/HDF pre-dilution mode; |

In a 45$^{th}$ aspect according to anyone of the previous aspects 1$^{st}$ to 42$^{nd}$, for a HDF pre-dilution treatment mode and/or for a HF pre-dilution treatment mode, the adjustment contribution term is (formula III):

$$c_{di,Na,isoNaK,adj} = -\frac{1}{M_{K_{NaCl}}}\Bigg(\left(M_{K_{NaHCO_3}} - M_{K_{NaCl}}\right) \tag{III}$$

$$\left(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\right) + +$$

$$\left(M_{K_{NaAc}} - M_{K_{NaCl}}\right)$$

$$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right) + +$$

$$\left(M_{K_{KCl}} - M_{K_{NaCl}}\right) \cdot$$

$$\left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right) + +$$

$$\frac{K_{b,Cit}}{K_u} \cdot \left(M_{K_{Na_3Cit}} - 3 M_{K_{NaCl}}\right)$$

-continued $$\left((0.167 \alpha_{bi}^{-3} + 0.125 \alpha_{bi}^{-2} + 0.706 \alpha_{bi}^{-1}) \cdot \cdot \right.$$

$$\left. \frac{Q_b \cdot f_{Cit} \cdot c_{pw,artCit} + Q_{inf} \cdot c_{di,Cit}}{Q_b \cdot f_{Cit} + Q_{inf}} - \right.$$

$$\left. c_{di,Na_3Cit}\right)\Bigg) + + \frac{Q_{do}}{K_u} \kappa_{rest3}$$

wherein:

in HF treatment mode, the clearance being equal to the dialyzer outlet flow, i.e.

$$K_u = \frac{Q_b \cdot f_{HCO_3} \cdot c_{pw,artHCO_3} + Q_{inf} \cdot c_{di,HCO_3}}{Q_b \cdot f_{HCO_3} + Q_{inf}}$$

$Q_{do}$;

is a diluted plasma water concentration of bicarbonate in blood entering the filtration unit;

$$\frac{Q_b \cdot f_{Ac} \cdot c_{pw,artAc} + Q_{inf} \cdot c_{di,Ac}}{Q_b \cdot f_{Ac} + Q_{inf}}$$

is a diluted plasma water concentration of acetate in blood entering the filtration unit;

$$\frac{Q_b \cdot f_K \cdot c_{pw,artK} + Q_{inf} \cdot c_{di,K}}{Q_b \cdot f_K + Q_{inf}}$$

is a diluted plasma water concentration of potassium in blood entering the filtration unit;

$$\frac{Q_b \cdot f_{Cit} \cdot c_{pw,artCit} + Q_{inf} \cdot c_{di,Cit}}{Q_b \cdot f_{Cit} + Q_{inf}}$$

is a diluted plasma water concentration of citrate in blood entering the filtration unit;

| | |
|---|---|
| $c_{di, Na, set, isoNa+K, adj}$ | Sodium set point adjustment (relative to isoconductive state) required to provide isonatrikalemic dialysis; |
| $M_{K, NaHCO_3}$ | Molar conductivity of sodium bicarbonate (NaHCO$_3$); |
| $M_{K, NaCl}$ | Molar conductivity of sodium chloride (NaCl); |
| $M_{K, NaAc}$ | Molar conductivity of sodium acetate (NaCH$_3$COO); |
| $M_{K, KCl}$ | Molar conductivity of potassium chloride (KCl); |
| $M_{K, Na_3Cit}$ | Molar conductivity of trisodium citrate (Na$_3$C$_6$H$_5$O$_7$) at ionic strength 150 mM; |
| $\kappa_{rest3}$ | Conductivity contribution from lesser solutes 3; |
| $c_{di, HCO_3}$ | Dialysis fluid concentration of bicarbonate as set by the operator; |
| $c_{di, K}$ | Dialysis fluid concentration of potassium ions (K$^+$) as determined by the used concentrate; |
| $c_{di, Ac}$ | Dialysis fluid concentration of acetate as determined by the used concentrate; |
| $c_{di, Na_3Cit}$ | Dialysis fluid concentration of total citrate as determined by the used concentrate; |
| $Q_{do}$ | Dialysate flow rate at filtration unit outlet (i.e., $Q_{di} + Q_{uf}$); |
| $K_u$ | Filtration unit clearance for urea; |
| $K_{b, Cit}$ | Filtration unit clearance for citrate; |
| $\alpha_{bi}$ | Donnan factor in HF/HDF pre-dilution mode; |

In a 46th aspect according to anyone of the previous aspects 1$^{st}$ to 42$^{nd}$, for a HDF post-dilution treatment mode and/or for a HF post-dilution treatment mode, the adjustment contribution term is (formula IV):

$$c_{di,Na,isotonic,adjh} = \tag{IV}$$

$$-\frac{1}{M_{K_{NaCl}}}\Bigg(\left(M_{K_{NaHCO_3}} - M_{K_{NaCl}}\right)\left(\frac{1}{\alpha} * c_{pw,HCO_3} - c_{di,HCO_3}\right) +$$

$$\left(M_{K_{NaAc}} - M_{K_{NaCl}}\right)\left(\frac{1}{\alpha} * c_{pw,Ac} - c_{di,Ac}\right) + + \left(M_{K_{KCl}} - M_{K_{NaCl}}\right)$$

$$(a * c_{pw,K} - c_{di,K}) + + \frac{K_{b_{Cit}}}{K_u}(M_{Na_3Cit} - M_{K_{NaCl}})$$

$$((0.167\alpha^{-3} + 0.125\alpha^{-2} + 0.706\alpha^{-1}) * c_{pw,Na_3Cit} -$$

$$c_{di,Na_3Cit}) + + \frac{Q_{do}}{K_u}(\kappa_{rest1} + \kappa_{rest2})\Bigg)$$

wherein:

| | |
|---|---|
| $c_{di, Na, isotonic, adj}$ | Sodium concentration set point adjustment (relative to isoconductive state) required to provide isotonic dialysis; |
| $M_{\kappa, NaHCO_3}$ | Molar conductivity of sodium bicarbonate ($NaHCO_3$); |
| $M_{\kappa, NaCl}$ | Molar conductivity of sodium chloride (NaCl); |
| $M_{\kappa, NaAc}$ | Is the molar conductivity of sodium acetate ($NaCH_3COO$); |
| $M_{\kappa, KCl}$ | Molar conductivity of potassium chloride (KCl); |
| $M_{\kappa, Na_3Cit}$ | Molar conductivity of trisodium citrate ($Na_3C_6H_5O_7$); |
| $\kappa_{rest1}$ | Conductivity contribution from lesser solutes 1; |
| $\kappa_{rest2}$ | Conductivity contribution from lesser solutes 2; |
| $c_{di, HCO_3}$ | Dialysis fluid concentration of bicarbonate as set by the operator; |
| $c_{di, K}$ | Dialysis fluid concentration of potassium ions ($K^+$) as determined by the used concentrate; |
| $c_{di, Ac}$ | Dialysis fluid concentration of acetate as determined by the used concentrate; |
| $c_{di, Na_3Cit}$ | Dialysis fluid concentration of total citrate as determined by the used concentrate; |
| $c_{pw, HCO_3}$ | Estimated or measured pre-dialysis concentration of bicarbonate anions ($HCO_3^-$) in plasma water; |
| $c_{pw, Ac}$ | Estimated or measured pre-dialysis concentration of acetate anions ($CH_3COO^-$) in plasma water; |
| $c_{pw, K}$ | Estimated or measured pre-dialysis concentration of potassium ions ($K^+$) in plasma water; |
| $c_{pw, Na_3Cit}$ | Estimated or measured or known pre-dialysis concentration of total citrate in plasma water; |
| $Q_{do}$ | Dialysate flow rate at filtration unit outlet (i.e., $Q_{di} + Q_{uf}$); |
| $K_u$ | Filtration unit clearance for urea; |
| $K_{b, Cit}$ | Filtration unit clearance for citrate; |
| $\alpha$ | Donnan factor; |

In a 47th aspect according to anyone of the previous aspects 1st to 42nd, for a HDF post-dilution treatment mode and/or for a HF post-dilution treatment mode, the adjustment contribution term is (formula V):

$$c_{di,Na,isoNa,adj} = -\frac{1}{M_{\kappa_{NaCl}}} \Bigg( \left(M_{\kappa_{NaHCO_3}} - M_{\kappa_{NaCl}}\right)\left(\frac{1}{\alpha} * c_{pw,HCO_3} - c_{di,HCO_3}\right) +$$

$$\left(M_{\kappa_{NaAc}} - M_{\kappa_{NaCl}}\right)\left(\frac{1}{\alpha} * c_{pw,Ac} - c_{di,Ac}\right) + +$$

$$\frac{K_{b_{Cit}}}{K_u}(M_{Na_3Cit} - 3M_{\kappa_{NaCl}})$$

$$((0.167\alpha^{-3} + 0.125\alpha^{-2} + 0.706\alpha^{-1}) * c_{pw,Na_3Cit} -$$

$$c_{di,Na_3Cit}) + + M_{\kappa_{KCl}}(\alpha * c_{pw,K} - c_{di,K}) + \frac{Q_{do}}{K_u}\kappa_{rest3} \Bigg)$$

wherein:

| | |
|---|---|
| $c_{di, Na, isoNa, adj}$ | Sodium concentration set point adjustment (relative to isoconductive state) required to provide isonatric dialysis; |
| $M_{\kappa, NaHCO_3}$ | Molar conductivity of sodium bicarbonate ($NaHCO_3$); |
| $M_{\kappa, NaCl}$ | Molar conductivity of sodium chloride (NaCl); |
| $M_{\kappa, NaAc}$ | Is the molar conductivity of sodium acetate ($NaCH_3COO$); |
| $M_{\kappa KCl}$ | Molar conductivity of potassium chloride (KCl); |
| $M_{\kappa, Na_3Cit}$ | Molar conductivity of trisodium citrate ($Na_3C_6H_5O_7$); |
| $\kappa_{rest3}$ | Conductivity contribution from lesser solutes 3; |
| $c_{di, HCO_3}$ | Dialysis fluid concentration of bicarbonate as set by the operator; |
| $c_{di, K}$ | Dialysis fluid concentration of potassium ions ($K^+$) as determined by the used concentrate; |
| $c_{di, Ac}$ | Dialysis fluid concentration of acetate as determined by the used concentrate; |
| $c_{di, Na_3Cit}$ | Dialysis fluid concentration of total citrate as determined by the used concentrate; |
| $c_{pw, HCO_3}$ | Estimated or measured pre-dialysis concentration of bicarbonate anions ($HCO_3^-$) in plasma water; |
| $c_{pw, Ac}$ | Estimated or measured pre-dialysis concentration of acetate anions ($CH_3COO^-$) in plasma water; |
| $c_{pw, K}$ | Estimated or measured pre-dialysis concentration of potassium ions ($K^+$) in plasma water; |
| $c_{pw, Na_3Cit}$ | Estimated or measured or known pre-dialysis concentration of total citrate in plasma water; |
| $Q_{do}$ | Dialysate flow rate at filtration unit outlet (i.e., $Q_{di} + Q_{uf}$); |
| $K_u$ | Filtration unit clearance for urea; |
| $K_{b, Cit}$ | Filtration unit clearance for citrate; |
| $\alpha$ | Donnan factor; |

In a 48th aspect according to anyone of the previous aspects $1^{st}$ to $42^{nd}$, for a HDF post-dilution treatment mode and/or for a HF post-dilution treatment mode, the adjustment contribution term is (formula VI):

$$c_{di,Na,isoNa+K,adj} = \\ -\frac{1}{M_{\kappa_{NaCl}}}\Bigg((M_{\kappa_{NaHCO_3}} - M_{\kappa_{NaCl}})\left(\frac{1}{\alpha} * c_{pw,HCO_3} - c_{di,HCO_3}\right) + \\ (M_{\kappa_{NaAc}} - M_{\kappa_{NaCl}})\left(\frac{1}{\alpha} * c_{pw,Ac} - c_{di,Ac}\right) + + \frac{K_{b_{Cit}}}{K_u} \\ (M_{Na_3Cit} - 3M_{\kappa_{NaCl}})((0.167\alpha^{-3} + 0.125\alpha^{-2} + 0.706\alpha^{-1}) * \\ c_{pw,Na_3Cit} - c_{di,Na_3Cit}) + + \\ (M_{\kappa_{KCl}} - M_{\kappa_{NaCl}})(\alpha * c_{pw,K} - c_{di,K}) + \frac{Q_{do}}{K_u}\kappa_{rest3}\Bigg)$$ (VI)

wherein:

| | |
|---|---|
| $c_{di, Na, isoNa+K, adj}$ | Sodium concentration set point adjustment (relative to isoconductive state) required to provide isonatrikalemic dialysis; |
| $M_{\kappa, NaHCO_3}$ | Molar conductivity of sodium bicarbonate ($NaHCO_3$); |
| $M_{\kappa, NaCl}$ | Molar conductivity of sodium chloride (NaCl); |
| $M_{\kappa, NaAc}$ | Is the molar conductivity of sodium acetate ($NaCH_3COO$); |
| $M_{\kappa, KCl}$ | Molar conductivity of potassium chloride (KCl); |
| $M_{\kappa, Na_3Cit}$ | Molar conductivity of trisodium citrate ($Na_3C_6H_5O_7$); |
| $\kappa_{rest1}$ | Conductivity contribution from lesser solutes 3; |
| $c_{di, HCO_3}$ | Dialysis fluid concentration of bicarbonate as set by the operator; |
| $c_{di, K}$ | Dialysis fluid concentration of potassium ions ($K^+$) as determined by the used concentrate; |
| $c_{di, Ac}$ | Dialysis fluid concentration of acetate as determined by the used concentrate; |
| $c_{di, Na_3Cit}$ | Dialysis fluid concentration of total citrate as determined by the used concentrate; |
| $c_{pw, HCO_3}$ | Estimated or measured pre-dialysis concentration of bicarbonate anions ($HCO_3^-$) in plasma water; |
| $c_{pw, Ac}$ | Estimated or measured pre-dialysis concentration of acetate anions ($CH_3COO^-$) in plasma water; |
| $c_{pw, K}$ | Estimated or measured pre-dialysis concentration of potassium ions ($K^+$) in plasma water; |
| $c_{pw, Na_3Cit}$ | Estimated or measured or known pre-dialysis concentration of total citrate in plasma water; |
| $Q_{do}$ | Dialysate flow rate at filtration unit outlet (i.e., $Q_{di} + Q_{uf}$); |
| $K_u$ | Filtration unit clearance for urea; |
| $K_{b, Cit}$ | Filtration unit clearance for citrate; |
| $\alpha$ | Donnan factor; |

In a $49^{th}$ aspect according to anyone of the previous aspects, the control unit is configured to calculate the plasma conductivity as a function of at least one flow rate, in particular said flow rate being chosen in the group including the dialysate flow rate at the outlet of the secondary chamber (4) and the blood flow rate in the blood lines (6, 7).

In a $50^{th}$ aspect according to the previous aspect, the control unit is configured to calculate the plasma conductivity as a function of the dialysate flow rate at the outlet of the secondary chamber (4) and the blood flow rate in the blood lines (6, 7).

In a $51^{st}$ aspect according to anyone of the previous aspects, the control unit is configured to calculate the plasma conductivity as a function of at least an efficiency parameter of the filtration unit (2), in particular a clearance of the filtration unit (2), optionally the urea clearance.

In a $52^{nd}$ aspect according to anyone of the previous aspects, the control unit is configured to calculate the plasma conductivity as a function of at least an initial conductivity of the dialysate.

In a $53^{rd}$ aspect according to anyone of the previous aspects, the control unit is configured to calculate the plasma conductivity as a function of at least a conductivity of the dialysis fluid in the dialysis supply line (8).

In a $54^{th}$ aspect according to anyone of the previous aspects, the control unit is configured to calculate the plasma conductivity according to the following formula (IV):

$$\kappa'_{p,1} = \kappa_{0,do} + \frac{Q_{do}}{Q_{Bset}}(\kappa_{0,do} - \kappa_{0,di})$$ (VII)

wherein:

| | |
|---|---|
| $\kappa_{p, 1}$ | Plasma conductivity first estimate; |
| $Q_{do}$ | Dialysate flow rate at filtration unit outlet (i.e., $Q_{di} + Q_{uf}$); |
| $Q_{bset}$ | Set blood flow rate at filtration unit inlet; |
| $\kappa_{0, di}$ | Dialysis fluid conductivity at the filtration unit inlet for a pure electrolyte solution; |
| $\kappa_{0, do}$ | Dialysate conductivity at the filtration unit outlet for a pure electrolyte solution; |

In a $55^{th}$ aspect according to anyone of the previous aspects, the control unit is configured to calculate the plasma conductivity according to the following formula (V):

$$\kappa''_{p,1} = \kappa_{0,di} + \frac{Q_{do}}{K_u}(\kappa_{0,do} - \kappa_{0,di})$$ (VIII)

wherein:

| | |
|---|---|
| $\kappa_{p, 1}$ | Plasma conductivity first estimate; |
| $Q_{do}$ | Dialysate flow rate at filtration unit outlet (i.e., $Q_{di} + Q_{uf}$); |

| | |
|---|---|
| $K_u$ | Filtration unit clearance for urea; |
| $\kappa_{0,di}$ | Dialysis fluid conductivity at the filtration unit inlet for a pure electrolyte solution; |
| $\kappa_{0,do}$ | Dialysate conductivity at the filtration unit outlet for a pure electrolyte solution; |

In a 56$^{th}$ aspect according to anyone of the previous aspects, immediately after calculating an initial plasma conductivity, the control unit is configured to drive the regulating means (10) to change the composition of the dialysis fluid and to set the dialysis fluid conductivity substantially equal to the calculated plasma conductivity.

In a 57$^{th}$ aspect according to the previous aspect, after setting the dialysis fluid conductivity substantially equal to the calculated plasma conductivity, the control unit is configured to execute a second calculating step, based on a second determined initial conductivity of the dialysate and on a second corresponding conductivity of the dialysis fluid in the dialysis supply line (8), of a second estimate of the initial plasma conductivity, said calculating the second estimate being performed maintaining the dialysis fluid conductivity substantially constant and substantially equal to the calculated plasma conductivity.

In a 58$^{th}$ aspect according to anyone of the previous aspects, after calculating the second estimate of the initial plasma conductivity, the control unit is configured to drive the regulating means (10) to change the composition of the dialysis fluid and to set the dialysis fluid conductivity substantially equal to said second estimate.

In a 59$^{th}$ aspect according to anyone of the previous aspects, the control unit is programmed to allow selection of at least one treatment mode chosen in the group including HF, HDF and HF treatment mode and to optionally allow selection between isotonic dialysis, isonatric dialysis, and isonatrikalemic dialysis, the control unit is configured to drive the regulating means as a function of the calculated plasma conductivity and of the chosen treatment mode to set either a desired dialysis fluid inlet conductivity or a desired dialysis fluid inlet substance concentration, in particular said substance being sodium.

In a 60$^{th}$ aspect according to the previous aspect, the control unit is programmed to keep the desired dialysis fluid inlet conductivity substantially constant throughout the remainder of the treatment.

In a 61$^{st}$ aspect according to anyone of the previous aspects, the setting of the second parameter value in the dialysis fluid includes the sub-step of calculating the parameter value as a function of the main contribution term, the adjustment contribution term and a compensation contribution term.

In a 62$^{nd}$ aspect according to the previous aspect, the compensation contribution term is dimensionally a concentration of a substance in a fluid.

In a 63$^{rd}$ aspect according to the previous two aspects, the sub-step of calculating the parameter value as a function of the main contribution term, the adjustment contribution term and the compensation contribution term is a sub-step of calculating an algebraic sum of at least the main contribution term, the adjustment contribution term and the compensation contribution term.

In a 64$^{th}$ aspect according to the previous three aspects, the compensation contribution term is a sodium compensation term to compensate for occurred unwanted sodium transfers during treatment.

In a 65$^{th}$ aspect according to the previous four aspects, the compensation contribution term is a sodium compensation term to compensate for unwanted sodium transfers occurred during calculation of said value representative of the parameter of the blood in said blood lines, particularly at the start of the treatment.

In a 66$^{th}$ aspect according to the previous aspect, the compensation contribution term has generally a negative value.

In a 67$^{th}$ aspect according to the previous six aspects, the control unit (12) is further configured, during a monitoring phase, to re-determine the blood parameter, the monitoring phase occurring a predetermined number of times during the treatment, at each monitoring phase an unwanted net transfer of a substance, e.g. sodium, occurs through the semipermeable membrane (5), the compensation contribution term is a sodium compensation term to compensate for occurred unwanted sodium transfers during the monitoring phase.

In a 68$^{th}$ aspect according to the previous seven aspects, the compensation contribution term for the unwanted substance transfer is calculated for distributing a compensation for the substance during the remaining treatment time.

In a 69$^{th}$ aspect according to the previous eight aspects, the compensation contribution term is a function of the remaining treatment time, i.e. total treatment time (T) minus elapsed treatment time ($t_i$), in particular is a function of $1/(T-t_i)$.

In a 70$^{th}$ aspect according to the previous nine aspects, the compensation contribution term is a function of the difference between the calculated substance, e.g. sodium, set point ($C_{di,Na,set,isotonic}$, $C_{di,Na,set,isoNa}$, $C_{di,Na,set,isoNa+K}$) and the actual dialysis fluid same substance, e.g. sodium, concentration set point ($c_{duva,set,actual}$) used during treatment.

In a 71$^{st}$ aspect according to the previous ten aspects, the compensation contribution term is calculated according to the following formula:

$$\sum_i \frac{1}{T-t_i} \int_{t_i}^{t_i+\Delta t_i} (c_{di,Na,set} - c_{di,Na,actual,i}) dt \quad \text{(IX)}$$

wherein $C_{di,Na,set,actual}$ is the actual dialysis fluid sodium concentration set point used during the treatment;

$C_{di,Na,set}$ is the calculated sodium set point which may correspond to either dialysis fluid concentration of sodium ions (Na$^+$) to provide isotonic dialysis $C_{di,Na,set,isotonic}$ or dialysis fluid concentration of sodium ions (Na$^+$) to provide isonatric dialysis $C_{di,Na,set,isoNa}$ or dialysis fluid concentration of sodium ions (Na$^+$) to provide isonatrikalemic dialysis $C_{di,Na,set,isoNa+K}$;

T is the total treatment time; and $t_i$ is the elapsed treatment time.

In a 72$^{nd}$ aspect according to the previous eleven aspects, the second parameter value in the dialysis fluid is calculated according to the following relation:

$$c_{di,Na,set,compensated} = c_{di,Na,set} + \sum_i \frac{1}{T-t_i} \int_{t_i}^{t_i+\Delta t_i} (c_{di,Na,set} - c_{di,Na,actual,i}) dt \quad \text{(X)}$$

wherein $C_{di,Na,set,actual}$ is the actual dialysis fluid sodium concentration set point used during the treatment;

$C_{di,Na,set}$, is the calculated sodium set point which may correspond to either dialysis fluid concentration of sodium ions (Na$^+$) to provide isotonic dialysis $C_{di,Na,set,isotonic}$ or dialysis fluid concentration of sodium ions (Na$^+$) to provide isonatric dialysis $C_{di,Na,set,isoNa}$ or dialysis fluid concentration of sodium ions (Na$^+$) to provide isonatrikalemic dialysis $C_{di,Na,set,isoNa+K}$;

T is the total treatment time; and $t_i$ is the elapsed treatment time.

In a 73$^{rd}$ aspect according to anyone of the previous aspects, the control unit (12) is not configured to run an HD treatment mode.

In a 74$^{th}$ aspect according to anyone of the previous aspects, in HDF pre-dilution mode and/or in HF pre-dilution mode, the control unit (12) is configured to calculate a diluted plasma water concentration of one or more substances due to pre-infusion flow, the substance being chosen in the group including bicarbonate, potassium, acetate, lactate, citrate.

In a 75$^{th}$ aspect according to anyone of the previous aspects, the control unit (12) is configured to store in a memory instruction for configuring the apparatus to run a HD or a HDF or HF treatment.

In a 76$^{th}$ aspect according to anyone of the previous aspects, the control unit (12) is configured to use a diluted plasma concentration in calculating the second parameter of the blood.

In a 77$^{th}$ aspect according to the previous aspect, the diluted plasma concentration is function of an infusion fluid flow rate, the infusion fluid being infused in the blood circuit upstream the filtration unit along a blood circulation direction.

Further characteristics and advantages of the present invention will better emerge from the detailed description that follows of at least an embodiment of the invention, illustrated by way of non-limiting example in the accompanying figures of the drawings.

BRIEF DESCRIPTION OF THE DRAWINGS

The description will now follow, with reference to the appended figures, provided by way of non-limiting example, in which.

DETAILED DESCRIPTION

Blood Treatment Apparatus

Figure 1:
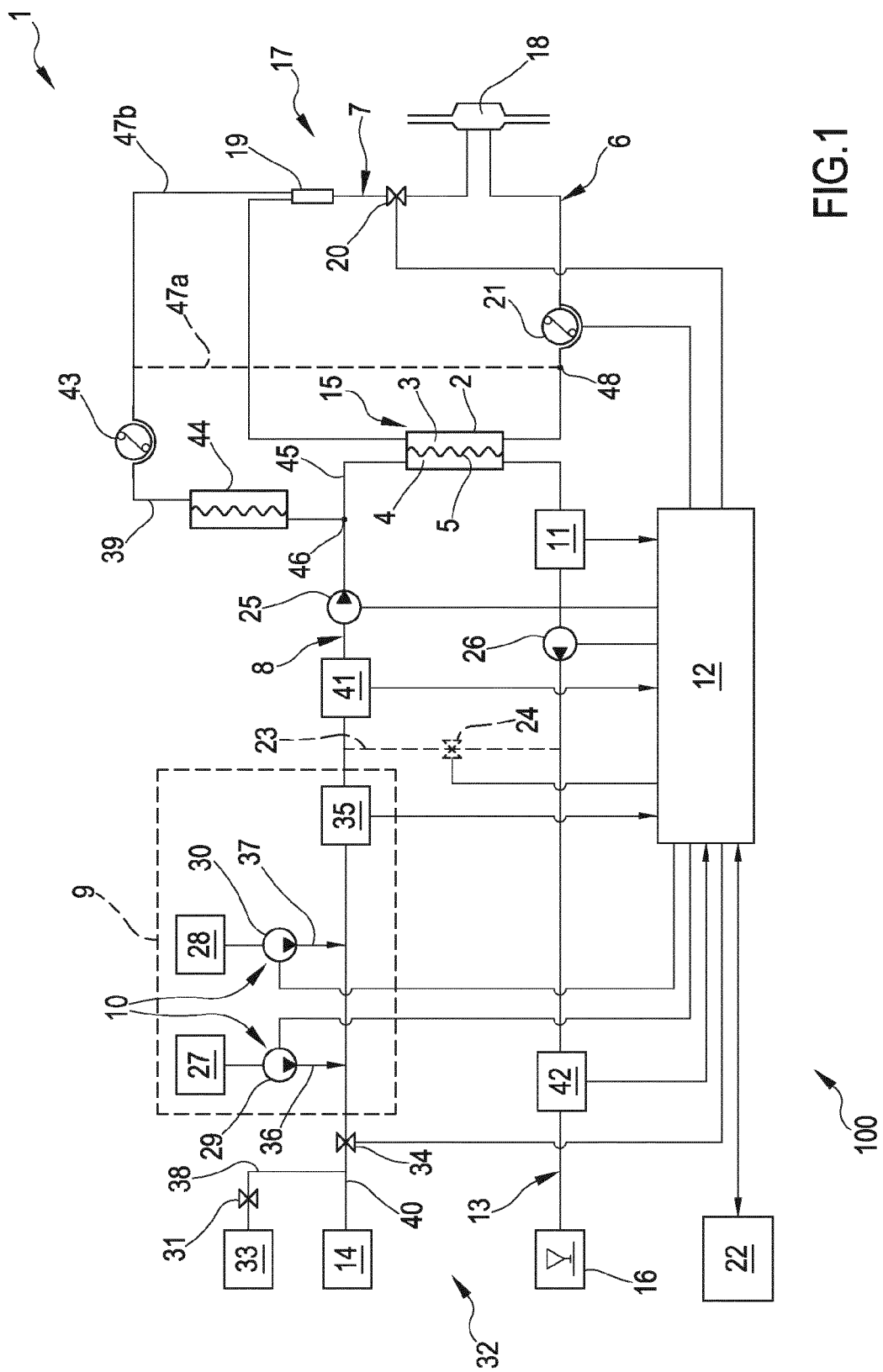
FIG. 1 schematically represents an extracorporeal blood treatment apparatus made according to an illustrating embodiment.
Figure 2:
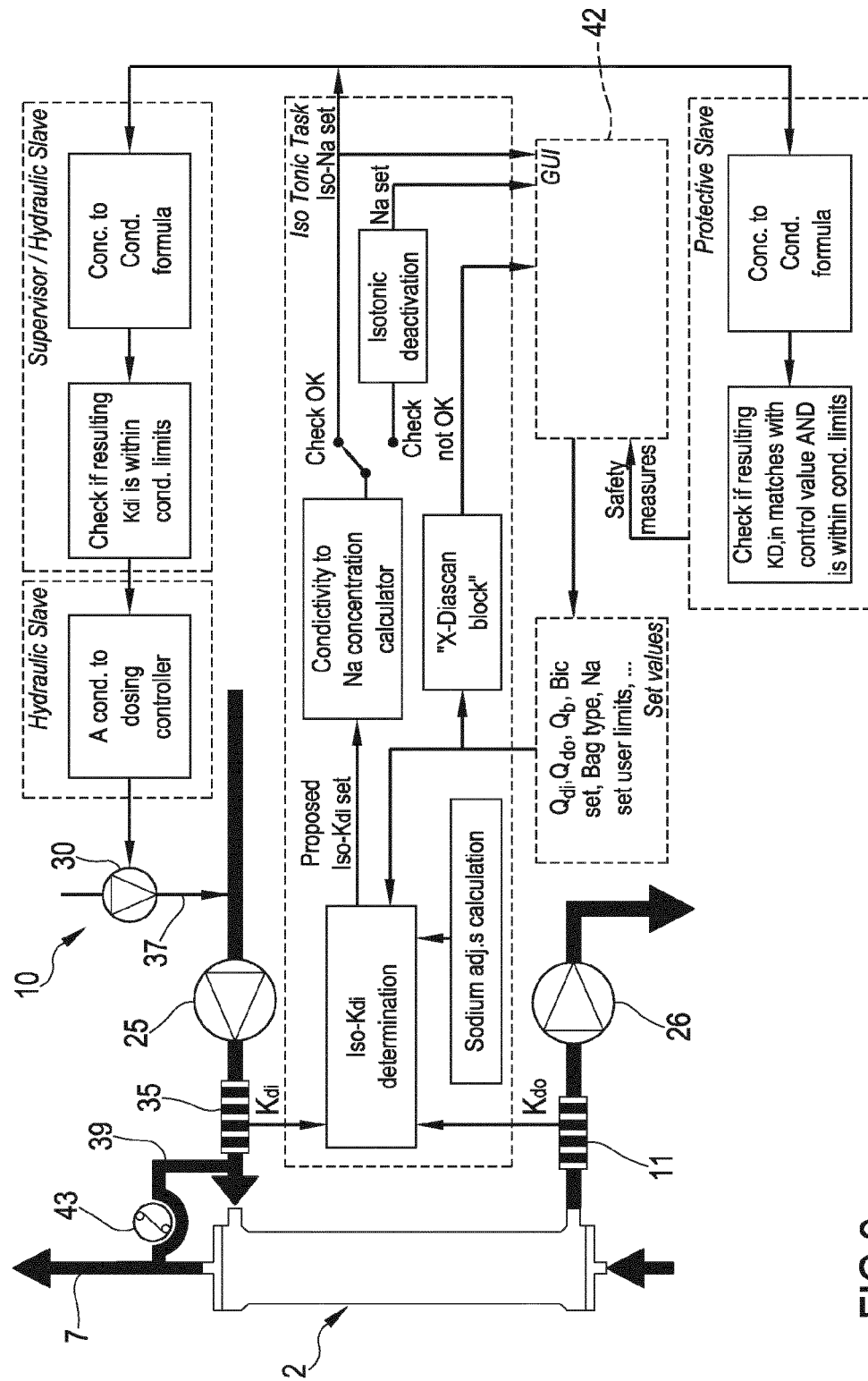
FIG. 2 is a schematic representing the main steps of the method of the present description.

FIG. 1 illustrates an extracorporeal blood treatment apparatus 1 in an embodiment of the invention.

An example of a hydraulic circuit 100 is schematically illustrated, but it is to be noted that the specific structure of the hydraulic circuit 100 is not relevant for the purposes of the present invention and therefore other and different circuits to those specifically shown in FIG. 1 might be used in consequence of the functional and design needs of each single medical apparatus.

The hydraulic circuit 100 exhibits a dialysis fluid circuit 32 presenting at least one dialysis supply line 8. Depending on the specific apparatus treatment mode, the dialysis supply line 8 may or, may not, assume different hydraulic circuit line configurations.

In a hemodialysis (HD) treatment mode, the supply line 8 is destined to transport a dialysis fluid from at least one source 14 towards a treatment station 15 where one or more filtration units 2, or dialyzers, operate. Dialysis fluid and blood exchange through the semipermeable membrane in the filtration unit 15 mainly by diffusion process.

In a hemofiltration (HF) treatment mode, the supply line 8 comprises an infusion line 39, which is destined to transport an infusion fluid from at least one source 14 to the blood circuit. The infusion line 39 may include an ultrafilter 44 to additionally filter the received fluid upstream the injection point into the blood circuit. The removal of waste products from the blood is achieved by using large amounts of ultrafiltration with simultaneous reinfusion of sterile replacement fluid in the blood circuit.

In a hemodiafiltration (HDF) treatment mode, the supply line 8 is destined to transport the dialysis fluid from the source 14 towards the treatment station 15 and also comprises the infusion line 39 to transport the infusion fluid from the source 14 to the blood circuit 17. HDF is a combination of hemodialysis and hemofiltration.

In general, though not essential, the source 14 for the supply line 8 and the infusion line 39 is the same (i.e. a dialysis fluid preparation devices 9). Of course, different sources may be used.

Additionally, the supply line 8 normally branches into the infusion line 39, infusing fluid in the blood circuit 17, and into an inlet line 45 directing the fluid to the treatment station 15. Referring to FIG. 1, a branch point is indicated with reference numeral 46.

Notwithstanding the fact that different hydraulic circuits 100 may be used to deliver HF, HD and HDF treatments having exclusively the relevant lines for the specific treatment (e.g. no infusion line 39 for HD, no inlet line 45 for HF), generally the hydraulic circuit 100 is of the kind shown in FIG. 1 and includes both infusion line 39 and inlet line 45, the apparatus control unit 12 may then control the passage of fluid trough said lines, depending on the selected treatment, by means e.g. proper valves or clamps.

The dialysis fluid circuit 32 further comprises at least one dialysis effluent line 13, destined for the transport of a dialysate liquid (spent dialysate and liquid ultrafiltered from the blood through a semipermeable membrane 5) from the treatment station 15 towards an evacuation zone, schematically denoted by 16 in FIG. 1.

The hydraulic circuit cooperates with a blood circuit 17, also schematically represented in FIG. 1 in its basic component parts. The specific structure of the blood circuit is also not fundamental, with reference to the present invention. Thus, with reference to FIG. 1, a brief description of a possible embodiment of a blood circuit is made, which is however provided purely by way of non-limiting example.

The blood circuit 17 of FIG. 1 comprises a blood withdrawal line 6 designed to remove blood from a vascular access 18 and a blood return line 7 designed to return the treated blood to the vascular access 18.

The blood circuit 17 of FIG. 1 further comprises a primary chamber 3, or blood chamber, of the blood filtration unit 2, the secondary chamber 4 of which is connected to the hydraulic circuit 100.

In greater detail, the blood withdrawal line 6 is connected at the inlet of the primary chamber 3, while the blood return line 7 is connected at the outlet of the primary chamber 3.

In turn, the dialysis supply line 8 is connected at the inlet of the secondary chamber 4, while the dialysis effluent line 13 is connected at the outlet of the secondary chamber 4.

The filtration unit 2, for example a dialyzer or a plasma filter or a hemofilter or a hemodiafilter, comprises, as mentioned, the two chambers 3 and 4 which are separated by a semipermeable membrane 5, for example of the hollow-fibre type or plate type.

The blood circuit 17 may also comprise one or more air separators 19: in the example of FIG. 1 a separator 19 is included at the blood return line 7, upstream of a safety valve 20.

Of course other air separators may be present in the blood circuit, such as positioned along the blood withdrawal line 6.

The safety valve 20 may be activated to close the blood return line 7 when, for example, for security reasons the blood return to the vascular access 18 has to be halted.

The extracorporeal blood treatment apparatus 1 may also comprise one or more blood pumps 21, for example positive displacement pumps such as peristaltic pumps; in the example of FIG. 1, a blood pump 21 is included on the blood withdrawal line 6.

The apparatus of above-described embodiment may also comprise a user interface 22 (e.g. a graphic user interface or GUI) and a control unit 12, i.e. a programmed/programmable control unit, connected to the user interface.

The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the medical apparatus may also comprise a closing device operating, for example, in the blood circuit 17 and/or in the dialysis fluid circuit 32 and commandable between one first operating condition, in which the closing device allows a liquid to flow towards the filtration unit 2, and a second operative position, in which the closing device blocks the passage of liquid towards the filtration unit 2.

In this case, the control unit 12 may be connected to the closing device and programmed to drive the closing device to pass from the first to the second operative condition, should an alarm condition have been detected.

In FIG. 1 the closing device includes the safety valve 20 (e.g. a solenoid valve) controlled by the unit 12 as described above. Obviously a valve of another nature, either an occlusive pump or a further member configured to selectively prevent and enable fluid passage may be used.

Alternatively or additionally to the safety valve 20, the closing device may also comprise a bypass line 23 which connects the dialysis fluid supply line 8 and the dialysate effluent line 13 bypassing the dialyzer, and one or more fluid check members 24 connected to the control unit 12 for selectively opening and closing the bypass line 23. The components (bypass line 23 and fluid check members 24), which may be alternative or additional to the presence of the safety valve 20 are represented by a broken line in FIG. 1.

The check members 24 on command of the control unit close the fluid passage towards the treatment zone and connect the source 14 directly with the dialysis effluent line 13 through the bypass line 23.

Again with the aim of controlling the fluid passage towards the filtration unit 2, a dialysis fluid pump 25 and a dialysate pump 26 may be included, located respectively on the dialysis fluid supply line 8 and on the dialysate effluent line 13 and also operatively connected to the control unit 12.

The apparatus also comprises a dialysis fluid preparation device 9 which may be of any known type, for example including one or more concentrate sources 27, 28 and respective concentrate pumps 29, 30 for the delivery, as well as at least a conductivity sensor 35.

Of course other kinds of dialysis fluid preparation devices 9 might be equivalently used, having a single or further concentrate sources and/or a single or more pumps.

Since the dialysis apparatus may comprise various liquid sources 14 (for example one or more water sources, one or more concentrate sources 27, 28, one or more sources 33 of disinfectant liquids) connected to the dialysis supply line 8 with respective delivery lines 36, 37 and 38, the apparatus may exhibit, at each delivery line, a respective check member (not all are shown) and, for example, comprising a valve member 31 and 34 and/or an occlusive pump.

The preparation device 9 may be any known system configured for on-line preparing dialysis fluid from water and concentrates.

The dialysis supply line 8 fluidly connects the preparation device 9 for preparing dialysis fluid to the filtration unit 2 and/or to the blood circuit 17. The preparation device 9 may be, for example, the one described in the U.S. Pat. No. 6,123,847 the content of which is herein incorporated by reference.

As shown, the dialysis supply line 8 connects the preparation device 9 for preparing dialysis fluid to the filtration unit 2 and comprises a main line 40 whose upstream end is intended to be connected to a source 14 of running water.

Delivery line/s 36/37 is/are connected to this main line 40, the free end of which delivery line/s is/are intended to be in fluid communication (for example immersed) in a container/s 27, 28 for a concentrated saline solution each containing sodium chloride and/or calcium chloride and/or magnesium chloride and/or potassium chloride.

Concentrate pump/s 29, 30 is/are arranged in the delivery line/s 36/37 in order to allow the metered mixing of water and concentrated solution in the main line 40. The concentrate pump/s 29, 30 is/are driven on the basis of the comparison between 1) a target conductivity value for the mixture of liquids formed where the main line 40 joins the delivery line/s 36/37, and 2) the value of the conductivity of this mixture measured by means of a conductivity sensor 35 arranged in the main line 40 immediately downstream of the junction between the main line 40 and the delivery line/s 36/37.

Therefore, as mentioned, the dialysis fluid may contain, for example, ions of sodium, calcium, magnesium, and potassium and the preparation device 9 may be configured to prepare the dialysis fluid on the basis of a comparison between a target conductivity value and an actual conductivity value of the dialysis fluid measured by the conductivity sensor 35 of the device 9.

The preparation device 9 comprises regulating means 10, of a known type (i.e. concentrate pump/s 29, 30), which is configured to regulate the concentration of a specific substance, in particular an ionic substance, in the dialysis liquid. Generally it is advantageous to control the sodium concentration of the dialysis fluid.

The dialysis supply line 8 forms an extension of the main line 40 of the preparation device 9 for preparing dialysis fluid. Arranged in this dialysis supply line, in the direction in which the liquid circulates, there are the first flow meter 41 and the dialysis fluid pump 25.

The supply line 8 branches (at branch point 46) into the infusion line 39, which, in the example of FIG. 1, is shown directly connected to the blood return line 7, in particular to the air separator 19 (solid line) via post infusion tract 47b.

Alternatively, the infusion line 39 may infuse infusion fluid in the blood withdrawal line 6 via pre-infusion tract 47a, in particular downstream the blood pump 21 (dotted line) at pre-infusion point 48.

It is also in the scope of the present description an embodiment including an infusion line 39 branching into a pre-infusion branch 47a and in a post infusion branch 47b directing infusion fluid, respectively, in the blood withdrawal line 6 and in the blood return line 7.

One or more infusion pumps 43 may be used to pump the desired flow of infusion fluid into the blood circuit. The infusion pump 43 may be a positive displacement pump (e.g. a peristaltic pump as shown) or any other pump adapted to displace infusion fluid (e.g. a volumetric pump).

The dialysis effluent line 13 may be provided with a dialysate pump 26 and a second flow meter 42. The first and second flow meters 41, 42 may be used to control (in a known manner) the fluid balance of a patient connected to the blood circuit 17 during a dialysis session.

A sensor 11 is provided on the dialysis effluent line 13, immediately downstream the filtration unit 2, to measure a parameter value of the dialysate in the dialysate effluent line.

In detail, the parameter of the dialysate, which is measured by the sensor 11 is at least one chosen in the group consisting of conductivity of the dialysate, a conductivity-related parameter of the dialysate, concentration of at least a substance in the dialysate and a concentration-related parameter of at least a substance in the dialysate.

In detail the sensor 11 is a conductivity sensor, which is connected to the dialysis effluent line 13, and is configured to detect conductivity values of the dialysate downstream of the filtration unit 2.

Alternatively (or in combination) sensor 11 may include a concentration sensor configured for measuring the concentration of at least one substance in the dialysate, such as sodium concentration.

Correspondingly, sensor 35 on the dialysis fluid supply line may be not a conductivity sensor and, differently, may include a concentration sensor configured for measuring the concentration of at least one substance in the dialysis fluid, such as sodium concentration.

The control unit 12 of the dialysis apparatus represented in FIG. 1 may be connected to a (graphic) user interface 22 through which it may receive instructions, for example target values, such as blood flow rate $Q_b$, dialysis fluid flow rate $Q_{di}$, infusion liquid flow rate $Q_{inf}$ (pre infusion and/or post infusion), patient weight loss WL. The control unit 12 furthermore may receive detected values by the sensors of the apparatus, such as the aforementioned flow meters 41, 42, the (e.g. conductivity) sensor 35 of the preparation device 9 and the (e.g. conductivity) sensor 11 in the dialysis effluent line 13. On the basis of the instructions received and the operating modes and algorithms which have been programmed, the control unit 12 drives the actuators of the apparatus, such as the blood pump 21, the aforementioned dialysis fluid and dialysate pumps 25, 26, and the preparation device 9, and the infusion pump 43.

As already mentioned, the described embodiments are intended to be non-limiting examples. In particular the circuits of FIG. 1 should not be interpreted as defining or limiting, as an apparatus such as in the invention may comprise other additional or alternative components to those described.

For example an ultrafiltration line may be included, with at least one respective pump connected to the dialysis effluent line 13.

The blood circuit of FIG. 1 is intended for double needle treatments; however, this is a non-limiting example of the blood set.

Indeed, the apparatus may be configured to perform single needle treatments, i.e. the patient is connected to the extracorporeal blood circuit by way of a single needle and the extracorporeal line from the patient is then split into a withdrawal line and a return line, using, for example, an 'Y' connector. During single needle treatment, a blood withdrawal phase removing blood from patient is alternated to a blood return phase in which blood is restituted to the patient.

Furthermore one or more devices for measuring specific substance concentrations might be implemented either (or both) in the dialysis fluid side or (and) in the blood side of the hydraulic circuit. Concentration of calcium, potassium, magnesium, bicarbonate, and/or sodium might be desired to be known.

Finally, the above-cited one or more pumps and all the other necessary temperature, pressure, and concentration sensors may operate either on the dialysis supply line 8 and/or on the dialysis effluent line 13, in order to adequately monitor the preparation and movement of the liquid in the hydraulic circuit.

Given the above description of a possible embodiment of extracorporeal blood treatment apparatus, thereafter the specific working of the apparatus and the algorithm programming the control unit are described.

Definitions

We define the "dialysis fluid" as the fluid prepared and, when appropriate based on the selected treatment, introduced to the second chamber (4) of the filtration unit (2)—e.g. HD and HDF—, the dialyzer. The dialysis fluid may also be denoted "fresh dialysis fluid".

We define the "dialysate" as the fluid from the outlet from the second chamber (4) of the filtration unit (2), the dialyzer. Dialysate is the spent dialysis fluid, comprising the uremic toxins removed from the blood.

We define "infusion fluid" as the fluid prepared and infused in the blood circuit (17), either in the blood withdrawal line (6) or in the blood return line (7) or in both blood lines (6, 7).

We define Isonatric dialysis' as a treatment where the sodium concentration of the dialysis fluid does not change pre- to post-filtration unit 2. It is then assumed that the sodium concentration of the dialysis fluid matches the sodium concentration of the plasma, and thus the diffusive sodium mass transfer is zero.

We define 'isotonic dialysis', as a treatment where the tonicity of the dialysis fluid does not change pre- to post-filtration unit 2. It is then assumed that the tonicity of the dialysis fluid matches the tonicity of the plasma.

We define an 'isonatrikalemic dialysis', as a treatment where the sum of sodium and potassium concentrations of the dialysis fluid does not change pre- to post-filtration unit 2.

We define 'isoconductive dialysis', as a dialysis treatment where the conductivity of the dialysis fluid does not change pre- to post-filtration unit 2, $\kappa_i = \kappa_{do}$, i.e. the pre- and post-dialyzer conductivities are equal on the fluid side.

We define 'plasma conductivity' (PC, $\kappa_p$) as the conductivity of the dialysis fluid in an isoconductive dialysis.

We define 'hemodialysis treatment mode' (HD) a dialysis treatment with fresh dialysis fluid is directed to the filtration unit 2 and no substitution fluid is infused in the blood circuit.

We define 'hemofiltration treatment mode' (HF) a treatment with substitution fluid directed into the blood circuit 17 and no fresh dialysis fluid is directed to the filtration unit 2.

We define 'hemofiltration treatment mode' in post-dilution (HF post-dilution) a treatment with substitution fluid directed into the blood circuit 17 downstream the filtration unit (no substitution fluid is directed in the blood circuit upstream the filtration unit).

We define 'hemofiltration treatment mode' in pre-dilution (HF pre-dilution) a treatment with substitution fluid directed into the blood circuit 17 upstream the filtration unit (no substitution fluid is directed in the blood circuit downstream the filtration unit).

We define 'hemodiafiltration treatment mode' (HDF) a treatment with both substitution fluid directed into the blood circuit 17 and fresh dialysis fluid directed to the filtration unit 2.

We define 'hemodiafiltration treatment mode' in post-dilution (HDF post-dilution) a treatment with both substitution fluid is directed into the blood circuit 17 downstream the filtration unit and fresh dialysis fluid directed to the filtration unit 2 (no substitution fluid is directed in the blood circuit upstream the filtration unit).

We define 'hemodiafiltration treatment mode' in pre-dilution (HDF pre-dilution) a treatment with both substitution fluid is directed into the blood circuit 17 upstream the filtration unit and fresh dialysis fluid directed to the filtration unit 2 (no substitution fluid is directed in the blood circuit downstream the filtration unit).

In this application, when "isotonic treatment" word is used alone, this actually implies isotonic, isonatric or isonatrikalemic dialyses.

In this application the term "citrate", and also the term "Cit", means that the component is in form of a salt of citric acid, such as sodium, magnesium, calcium, or potassium salt thereof. The citric acid (denoted $C_6H_8O_7$) is deprotonated stepwise, therefore the "citrate" include all the different forms, citrate (denoted $C_6H_5O_7^{3-}$), hydrogen citrate (denoted $C_6H_6O_7^{2-}$), and dihydrogen citrate (denoted $C_6H_7O_7^-$).

The term "citrate" or "total citrate" means that the total amount of citric acid and any salts thereof, such as its sodium, magnesium, calcium, or potassium salt thereof.

In other terms, "total citrate" is the sum of free citrate ions and citrate containing complexes and ion pairs.

Glossary

The following terms are consistently used throughout the equations provided in the following description of the detailed working of the extracorporeal blood treatment apparatus.

| Name | Description | Unit |
| --- | --- | --- |
| $\kappa_{d, pre} = \kappa_{di}$ | Dialysis fluid conductivity upstream the filtration unit (corresponding to final conductivity of the dialysis fluid); | mS/cm |
| $\kappa_{d, post} = \kappa_{do}$ | Dialysate conductivity downstream the filtration unit; | mS/cm |
| PC = $\kappa_p$ | Plasma conductivity; | mS/cm |
| $Q_{di}$ | Dialysis fluid flow rate at filtration unit inlet; | mL/min |
| $Q_d$ | Total dialysis fluid flow rate; | mL/min |
| $Q_{inf}$ | Dialysis fluid infusion flow rate, e.g. dialysis fluid directly infused in the blood circuit; | mL/min |
| $Q_{inf, pre}$ | Dialysis fluid pre-infusion flow rate, e.g. dialysis fluid directly infused in the blood circuit upstream the filtration unit; | mL/min |
| $Q_{inf, post}$ | Dialysis fluid post-infusion flow rate, e.g. dialysis fluid directly infused in the blood circuit downstream the filtration unit; | mL/min |
| $Q_{do}$ | Dialysate flow rate at filtration unit outlet (i.e., $Q_{di} + Q_{uf}$); | mL/min |
| $Q_{wl}$ | Weight loss rate; | mL/min |
| $Q_u$ | Total ultrafiltration flow rate; | mL/min |
| $Q_{bset}$ | Set blood flow rate at filtration unit inlet; | mL/min |
| $Q_b$ | Real blood flow rate at filtration unit inlet (set blood flow compensated for arterial pressure); | mL/min |
| $Q_{bwi}$ | Dialyzer inlet blood water flow rate; | mL/min |
| $Q_{bwo}$ | Dialyzer outlet blood water flow rate; | mL/min |
| $K_u$ | Filtration unit clearance for urea; | mL/min |
| $K_{b, Cit}$ | Filtration unit clearance for citrate; | mL/min |
| $K_m A$ | Modified mass transfer coefficient; | mL/min |

-continued

| Name | Description | Unit |
|---|---|---|
| $K_0A$ | Urea mass transfer coefficient of filtration unit (e.g. average of normally used dialyzers); | mL/min |
| Pe | Peclet number; | dimensionless |
| $c_{di, Na, start}$ | Dialysis fluid concentration of sodium ions (Na$^+$) at the start of treatment, automatically calculated and set by the machine before the start of the treatment; | mmol/L |
| $c_{di, Na, kp, pre}$ | Dialysis fluid concentration of sodium ions (Na$^+$) at isoconductive dialysis, i.e., when the dialysis fluid conductivity $\kappa_{di}$ matches the estimated pre-dialysis plasma conductivity $\kappa_{p, pre}$; | mmol/L |
| $c_{di, Na, set}$ | Dialysis fluid concentration of sodium ions (Na$^+$) to provide isotonic or isonatric or isonatrikalemic dialysis; | mmol/L |
| $c_{di, Na, set, isotonic}$ | Dialysis fluid concentration of sodium ions (Na$^+$) to provide isotonic dialysis; | mmol/L |
| $c_{di, Na, set, isotonic, adj}$ | Sodium set point adjustment (relative to isoconductive state) required to provide isotonic dialysis; | mmol/L |
| $c_{di, Na, set, isoNa}$ | Dialysis fluid concentration of sodium to provide isonatric dialysis; | mmol/L |
| $c_{di, Na, set, isoNa, adj}$ | Sodium set point adjustment (relative to isoconductive state) required to provide isonatric dialysis; | mmol/L |
| $c_{di, Na, set, isoNa+K}$ | Dialysis fluid concentration of sodium to provide isonatrikalemic dialysis; | mmol/L |
| $c_{di, Na, set, isoNa+K, adj}$ | Sodium set point adjustment (relative to isoconductive state) required to provide isonatrikalemic dialysis; | mmol/L |
| $c_{di, Na, set, compensated}$ | Sodium concentration set point to compensate unwanted sodium transfers; | mmol/L |
| $c_{di, Na, set, actual}$ | Actual dialysis fluid sodium concentration set point during the treatment at the time an additional compensation is to be applied for; | mmol/L |
| $c_{di, HCO_3}$ | Dialysis fluid concentration of bicarbonate as set by the operator; | mmol/L |
| $c_{di, K}$ | Dialysis fluid concentration of potassium ions (K$^+$) as determined by the used concentrate; | mmol/L |
| $c_{di, Ac}$ | Dialysis fluid concentration of acetate as determined by the used concentrate; | mmol/L |
| $c_{di, Na_3Cit}$ | Dialysis fluid concentration of total citrate as determined by the used concentrate; | mmol/L |
| $c_{di, g}$ | Dialysis fluid concentration of glucose as determined by the used concentrate; | mmol/L |
| $c_{pw, bi}$ | Plasma water concentration in blood entering the filtration unit; | mmol/L |
| $c_{pw, art}$ | Plasma water concentration in blood from patient; | mmol/L |
| $c_{pw, Na}$ | Estimated or measured pre-dialysis concentration of sodium ions (Na$^+$) in plasma water; | mmol/L |

-continued

| Name | Description | Unit |
|---|---|---|
| $c_{pw, HCO_3}$ | Estimated or measured pre-dialysis concentration of bicarbonate anions ($HCO_3^-$) in plasma water; | mmol/L |
| $c_{pw, Ac}$ | Estimated or measured pre-dialysis concentration of acetate anions ($CH_3COO^-$) in plasma water; | mmol/L |
| $c_{pw, K}$ | Estimated or measured pre-dialysis concentration of potassium ions ($K^+$) in plasma water; | mmol/L |
| $c_{pw, Na_3Cit}$ | Estimated or measured or known pre-dialysis concentration of total citrate in plasma water; | mmol/L |
| $c_{pw, art_{Na}}$ | Estimated or measured pre-dialysis concentration of sodium ions ($Na^+$) in blood from patient; | mmol/L |
| $c_{pw, art_{HCO3}}$ | Estimated or measured pre-dialysis concentration of bicarbonate anions ($HCO_3^-$) in blood from patient; | mmol/L |
| $c_{pw, art_{Ac}}$ | Estimated or measured pre-dialysis concentration of acetate anions ($CH_3COO^-$) in blood from patient; | mmol/L |
| $c_{pw, art_K}$ | Estimated or measured pre-dialysis concentration of potassium ions ($K^+$) in blood from patient; | mmol/L |
| $c_{pw, art_{Na_3Cit}}$ | Estimated or measured or known pre-dialysis concentration of total citrate in blood from patient; | mmol/L |
| $c_{p, g}$ | Estimated or measured pre-dialysis concentration of glucose in plasma; | mmol/L |
| $c_{p, u}$ | Estimated or measured pre-dialysis concentration of urea in plasma; | mmol/L |
| $c_{inf}$ | Infusion fluid flow concentration; | mmol/L |
| $f_{bw}$ | Apparent blood water fraction, i.e., the part of whole blood that appears as pure water for urea; | dimensionless |
| $f_{pw}$ | Plasma water fraction, i.e., the part of plasma that is pure water; | dimensionless |
| $f_i$ | Dialyzable blood water fraction for substance i of the dialyzer blood (i = $Na^+$, $HCO_3^-$, $K^+$, $Ac^-$, $Cit^{3-}$); | dimensionless |
| $f_{Na}$ | Dialyzable blood water fraction for sodium ions ($Na^+$) of the dialyzer blood; | dimensionless |
| $f_{HCO_3}$ | Dialyzable blood water fraction for bicarbonate ions ($HCO_3^-$) of the dialyzer blood; | dimensionless |
| $f_{Ac}$ | Dialyzable blood water fraction for acetate ions ($Ac^-$) of the dialyzer blood; | dimensionless |
| $f_K$ | Dialyzable blood water fraction for potassium ions ($K^+$) of the dialyzer blood; | dimensionless |
| $f_{Cit}$ | Dialyzable blood water fraction for substance citrate ions ($Cit^{3-}$) of the dialyzer blood; | dimensionless |
| $f_{g, KB}$ | Glucose clearance fraction, i.e., the relative glucose clearance compared to urea clearance; | dimensionless |
| $f_{cw}$ | Cell water fraction; | dimensionless |
| Hct | Red cell fraction of blood; | dimensionless |
| $\gamma_{cw, u}$ | Plasma water fraction; | dimensionless |
| $\gamma_{cw, i}$ | Fraction of cell water available for dialysis for substance i (i = $Na^+$, $HCO3^-$, $K^+$, $Ac^-$, $Cit^{3-}$); | dimensionless |

| Name | Description | Unit |
|---|---|---|
| $c_{p,tp}$ | Total plasma protein concentration in blood leaving patient; | g/L |
| $c_{pi,tp}$ | Total plasma protein concentration in blood entering dialyzer; | g/L |
| $\kappa_{0,di}$ | Dialysis fluid conductivity at filtration unit inlet for a pure electrolyte solution (i.e. without glucose, either because the actual solution does not contain glucose, or because the conductivity has been compensated for the influence of glucose); | mS/cm |
| $\kappa_{0,do}$ | Dialysate conductivity at filtration unit outlet for a pure electrolyte solution (i.e. without glucose and urea, because the conductivity has been compensated for the influence of glucose and urea); | mS/cm |
| $\kappa_{p,1}$ and $\kappa_{p,2}$ | 1st and 2nd estimate of plasma conductivity; | mS/cm |
| $\kappa_{p,pre}$ | Estimate of plasma conductivity at beginning of treatment (representing a pre-dialysis value); | mS/cm |
| $\kappa_{isotonic}$ | Conductivity offset between $\kappa_{do}$ and $\kappa_{di}$ to provide isotonic dialysis (correspondent to $c_{di,Na,isotonic,adj}$); | mS/cm |
| $\kappa_{isoNa}$ | Conductivity offset between $\kappa_{do}$ and $\kappa_{di}$ to provide isonatric dialysis (correspondent to $c_{di,Na,isoNa,adj}$); | mS/cm |
| $\kappa_{isoNa+K}$ | Conductivity offset between $\kappa_{do}$ and $\kappa_{di}$ to provide isonatrikalemic dialysis (correspondent to $c_{di,Na,isoNa+K,adj}$); | mS/cm |
| $\kappa_{rest1}$ | Conductivity contribution from lesser solutes 1; | mS/cm |
| $\kappa_{rest2}$ | Conductivity contribution from lesser solutes 2; | mS/cm |
| $\kappa_{rest3}$ | Conductivity contribution from lesser solutes 3; | mS/cm |
| $\gamma g$ | Conductivity correction term for glucose; | $M^{-1}$ = L/mol |
| $\gamma u$ | Conductivity correction term for urea; | $M^{-1}$ = L/mol |
| $M_{\kappa,NaHCO_3}$ | Molar conductivity of sodium bicarbonate ($NaHCO_3$) at ionic strength 150 mM; | L · mS/mol · cm |
| $M_{\kappa,NaCl}$ | Molar conductivity of sodium chloride (NaCl) at ionic strength 150 mM; | L · mS/mol · cm |
| $M_{\kappa,NaAc}$ | Molar conductivity of sodium acetate ($NaCH_3COO$) at ionic strength 150 mM; | L · mS/mol · cm |
| $M_{\kappa,KCl}$ | Molar conductivity of potassium chloride (KCl) at ionic strength 150 mM; | L · mS/mol · cm |
| $M_{\kappa,Na_3Cit}$ | Molar conductivity of trisodium citrate ($Na_3C_6H_5O_7$) at ionic strength 150 mM; | L · mS/mol · cm |
| T | Set total treatment time; | min |
| t | Elapsed time into treatment; | min |
| $\alpha$ | Donnan factor; | |
| $\alpha_{bi}$ | Donnan factor in HF/HDF pre-dilution mode; | |

The Donnan factor indicates a value of electroneutrality to be kept over the membrane. For estimating the Donnan factor reference is made to Trans Am Soc Artif Intern Organs, 1983; 29; 684-7, "Sodium Fluxes during hemodialysis", Lauer A., Belledonne M., Saccaggi A., Glabman S., Bosch J.

Solution Proposal

The technical solution here described is applicable to HD, HDF, and HF treatment modes, particularly making use of concentrates with acetate and/or citrate. The solution consists of three main parts:

Estimating PC at the beginning of the treatment (i.e., $\kappa_{p,pre}$); in more detail, isoconductivity is estimated at the beginning of treatment. In particular, the estimation is done with an iterative method; after one/two iterations the estimated value is generally considered sufficiently accurate;

Setting the dialysis fluid sodium concentration such that the dialysis fluid tonicity (or sodium or sodium+potassium concentration) is not changed during its passage through the filtration unit; this is achieved by creating a dialysis fluid with a conductivity that is equal to the isoconductivity corrected by an offset;

Maintaining the dialysis fluid composition throughout the whole treatment.

The various steps of the proposed method described below are intended to be performed by the control unit 12 of the extracorporeal blood treatment device 1, even if not explicitly stated.

In particular a treatment session is started, preferably, but not necessarily, as a double needle hemodialysis treatment.

The user shall input the treatment mode (e.g. HD, HF, HDF) and the prescription values through the user interface 22. For example the set values for total weight loss WL and total treatment time T are provided, as well as the blood flow rate $O_b$ and the fresh dialysis flow rate $Q_{di}$. If required also infusion rate $Q_{inf}$ or the total accumulated infusion volume ($V_{inf}$), is provided.

Other parameters may be entered through the user interface, such as concentrate type, sodium user limits, etc.

The operator has to further input the 'bicarbonate' set before starting the treatment.

The control unit 12 calculates either the initial dialysis liquid conductivity or the initial concentration of at least one solute, e.g. sodium, in the dialysis liquid in order to start with a dialysis fluid conductivity as close as possible to the expected patient pre-dialytic plasma conductivity.

In order to not disturb the tonicity of the patient, it is necessary to set the fluid composition as quickly as possible so that the patient initial plasma conductivity is not inadvertently changed. Thus, estimating of the plasma conductivity has to be done as rapidly as possible when treatment starts; moreover, since the estimation is preferably performed only once, this measure should be as reliable as possible.

In this respect it is worth to note that, in the following detailed description, reference is made to regulating means controlling concentration of an ionic substance, in detail sodium concentration, in the preparation of the dialysis fluid so as to obtain a desired conductivity of the dialysis fluid.

However, regulating means directly regulating the overall dialysis fluid conductivity is also included in the spirit of the present description or, alternatively, regulating means modifying the concentration of a different ionic substance is included in the present description, too.

Given the above, the control unit 12 sets a parameter value for the dialysis fluid in the dialysis fluid supply line 8 at an initial set point; in general the parameter of the dialysis fluid is either the conductivity of the dialysis fluid, or a conductivity-related parameter of the dialysis fluid, or concentration of at least a substance (in particular an ionic substance and in more detail sodium) in the dialysis fluid, or a concentration-related parameter of at least a substance (e.g. sodium) in the dialysis fluid.

In detail, the control unit 12 is configured to set the parameter value for the dialysis fluid at the initial set point so that a dialysis fluid conductivity matches a first estimate of the plasma conductivity of the blood.

In the specific, the control unit 12 calculates the initial set point of the substance concentration and drives the regulating means 10 acting on the sodium concentration in the dialysis liquid.

The set point is calculated before starting the blood circulation (i.e. before starting the treatment).

In order to calculate the dialysis composition initial set point alternative ways might be used, e.g. determine a certain sodium concentration (see below), or using an average plasma conductivity from a large population, or using an average plasma conductivity from a large population corrected for the composition of the dialysis fluid, or calculate based on historic patient data.

In any case, the initial set point for the dialysis liquid is calculated by the control unit 12 so that the expected plasma conductivity is the best guess of plasma conductivity that may be calculated, without prior knowledge of the individual patient.

The selected treatment mode (HD/HF/HDF) also affects the initial estimation of the isoconductivity.

Before explaining in detail the estimation of the initial set point for the dialysis liquid, it is worth to clarify how certain relevant parameters paying a role in the estimation are determined.

Estimation of Dialyzer Clearance

Since the filtration unit (dialyzer) clearance K isn't known, it is necessary to estimate it. For the purpose of the estimation, it is assumed that all ions have the same dialyzer clearance, which is equal to the urea clearance.

In HDF treatments it is of fundamental importance to distinguish between the dialyzer clearance, which is related to the transport across the membrane, and the treatment (patient) clearance which describes the removal of a substance from the patient. The patient clearance has clinical interest, whereas for the purpose of calculating the initial set point the interest is in the dialyzer properties. Thus, when clearance is referred to in this document, unless otherwise stated, it is the filtration unit/dialyzer clearance.

In the calculation of clearance, the ultrafiltration flow through the membrane must be taken into account. The total ultrafiltration flow $Q_u$ is the sum of the weight loss flow rate $Q_{wl}$ and the infusion flow $Q_{inf}$:

$$Q_u = Q_{wl} + Q_{inf} \tag{1}$$

In HD treatment mode, the infusion flow $Q_{inf}$ is zero.

In general, the infusion flow $Q_{inf}$ is the sum of the pre-infusion flow rate $Q_{inf,pre}$ (i.e. the fluid infused in the blood circuit 17 upstream the filtration unit 2) and the post-infusion flow rate $Q_{inf,post}$ (i.e. the fluid infused in the blood circuit 17 downstream the filtration unit 2).

The dialyzer inlet fluid flow is:

$$Q_{di} = Q_d - Q_{inf} \tag{2}$$

where $Q_d$ is the total dialysis fluid flow rate, i.e. the total flow rate of dialysis fluid which is prepared by the preparation device 9 and which is then split (if appropriate) into a fluid flow ($Q_{di}$) to the filtration unit and a fluid flow ($Q_{inf}$) to be infused in the blood circuit.

In HF treatment mode, the dialyzer inlet fluid flow $Q_{di}$ is zero, since $Q_d = Q_{inf}$.

The dialyzer outlet fluid flow $Q_{do}$ can be calculated as:

$$Q_{do} = Q_{di} + Q_u \quad (3)$$

The clearance $K_u$ can be calculated with the following equations:

$$K_u = Q_{bwi} \cdot \frac{1 - \frac{Q_{bwo}}{Q_{bwi}} \cdot \psi}{1 - \frac{Q_{bwo}}{Q_{do}} \cdot \psi} \quad (4)$$

where $$\psi = \frac{Q_{do}}{Q_{di}} \cdot \left(\frac{Q_{bwo} \cdot Q_{do}}{Q_{bwi} \cdot Q_{di}}\right)^{\frac{k_m A}{Q_u}} \quad (5)$$

$k_m A$ is the modified mass transfer coefficient:

$$k_m A = \frac{Pe}{e^{Pe} - 1} * k_0 A \quad (6)$$

and $k_0 A$ is the mass transfer coefficient of the dialyzer.

$k_0 A$ may be derived having information about the dialyzer used, e.g. the apparatus may receive the data from the user or by reading the specific component identification data.

Alternatively the control unit 12 may assume a standard dialyzer with, e.g. a $k_0 A = 1100$ ml/min as a fixed value. In this latter case, the error in calculated K will be within ±10% for all the commonly used dialyzers.

Pe is the so called Peclet number which is defined as $$Pe = \frac{Q_u}{k_0 A} \quad (7)$$

$Q_{bwi}$ is the dialyzer inlet blood water flow, which in HD and HDF post-dilution can be calculated as:

$$Q_{bwi} = f_{bw} Q_b \quad (8)$$

Vice versa, in HDF pre-dilution, the dialyzer inlet blood water flow must include the infusion flow:

$$Q_{bwi} = f_{bw} Q_b + Q_{inf} \quad (9)$$

In this equation, $Q_b$ is the real (arterial) blood flow rate and $f_{bw}$ is the dialyzable blood water fraction, which can be calculated with the equation:

$$f_{bw} = f_{cw} \cdot \gamma_{cw,u} \cdot Hct + f_{pw} \cdot (1 - Hct) \quad (10)$$

wherein the used symbols meaning is clarified in the glossary section.

With the reference values stated above, the dialyzable blood water fraction $f_{bw}$ for urea will be, e.g. 0.89 at normal conditions for hemodialysis.

The dialyzer outlet blood water flow can be calculated from $$Q_{bwo} = Q_{bwi} - Q_u \quad (11)$$

Estimation of Dialyzer Clearance—HF Treatment

In the HF treatment mode, the clearance calculation is simple, since the clearance is equal to the dialyzer outlet flow:

$$K_u = Q_{do} = Q_u = Q_w + Q_{wl} \quad (12)$$

Since by definition, $Q_{di} = 0$ in HF.

Estimation of Citrate Clearance

For citrate, the free ion $Cit^{3-}$ does not dominate over its complexes and ion pairs. There are substantial parts of $CaCit^-$, $MgCit^-$ and $NaCit^{2-}$ together with some $HCit^{2-}$ depending on pH in blood plasma and dialysis solutions.

We approximate that the individual clearance values are close to a single value denoted $K_{b_{Cit}}$.

This clearance is calculated for the actual flow rates using a mass transfer coefficient value of $k_0 A_{Cit} = 0.212 \cdot k_0 A$ into the $K_u$ formulas (4), (5), (6).

Estimation of the Plasma Water Fraction

HD and HDF/HF Post-Dilution

The plasma water fraction depends on the total plasma protein concentration $c_{p,tp}$ and can be estimated as:

$$f_{pw} = 1 - 0.00107 \cdot c_{p,tp} \quad (13)$$

where $c_{p,tp}$ is the plasma protein concentration. With a normal plasma protein concentration $c_{p,tp} = 70$ g/L, the plasma water fraction is $f_{pw} = 0.925$.

HDF/HF Pre-Dilution

In HDF and HF pre-dilution mode, the dilution of the blood and the corresponding reduction of the total protein concentration must be taken into account to calculate the plasma water fraction for the blood in the dialyzer.

This is done with the following equations:

$$c_{pi,tp} = \frac{Q_b * (1 - Hct) * c_{p,tp}}{Q_b * (1 - Hct) + Q_{inf}} \quad (14)$$

$$f_{pw} = 1 - 0.00107 \cdot c_{pi,tp} \quad (15)$$

the used symbols meaning is clarified in the glossary section.

Estimation of the Donnan Factor α

HD and HDF/HF Post-Dilution

The transport of charged permeable substances over the dialyzer membrane is affected by the charged plasma proteins. The effect is quantified by a Donnan factor α.

If the plasma protein concentration $c_{p,tp}$ is known, the Donnan factor α for a single charged cation can be estimated with the equation:

$$\alpha = 1.004 \cdot e^{-0.0008 * c_{p,tp}} \quad (16)$$

With a normal plasma total protein concentration $c_{p,tp} = 70$ g/L, the Donnan factor is α=0.95 at conditions typical for hemodialysis.

HDF/HF Pre-Dilution

In HDF and HF pre-dilution mode, the dilution of the blood and the corresponding reduction of the total protein concentration must be taken into account when calculating the Donnan factor for the blood in the dialyzer.

This is done with the following equations:

$$c_{pi,tp} = \frac{Q_b * (1 - Hct) * c_{p,tp}}{Q_b * (1 - Hct) + Q_{inf}} \quad (17)$$

$$\alpha_{bi} = 1.004 * e^{-0.0008 * c_{pi,tp}} \quad (18)$$

wherein the used symbols meaning is clarified in the glossary section.

Estimation of Dialysis Fluid Starting Composition

In general terms, the control unit 12 is configured to calculate the initial set point of the substance concentration to be set (e.g. sodium) in the dialysis fluid as a function of the treatment mode. In other terms, depending on whether HD, HF or HDF is selected, the control unit 12 determines the initial set point based on different mathematical relationships which will be here below explained and detailed.

Moreover, the control unit 12 is configured to calculate the initial set point as a function of the difference in concentration of at least one (and in detail several) further substance in the dialysis fluid and the same further substance in the plasma. It is noted that in case of HDF pre-dilution and HF pre-dilution treatment modes, the concentration of the substance in the plasma is adjusted to take into consideration its dilution due to infusion.

The calculation is based on average pre-dialysis concentrations of at least one (and preferably all) substance chosen between sodium, potassium, acetate, citrate, and bicarbonate (as well as other solutes) in a large patient population, plus the contribution related to dialysis fluid of bicarbonate, potassium, acetate, and citrate resulting from the prescription and from the chosen concentrate combination.

The control unit 12 calculates the initial set point also as a function of the concentration of at least one, in particular two, and precisely all the substances in the dialysis fluid included in the group comprising bicarbonate, potassium, acetate, and citrate.

Furthermore, the control unit 12 calculates the initial set point of the substance (i.e. sodium) in the dialysis fluid also as a function of the difference in concentration of one or more further substances in the dialysis fluid different from sodium; in particular these substances include bicarbonate, potassium, acetate, and citrate and two, and precisely all, the differences, in particular weighted differences, in concentration value of the mentioned substances in the dialysis fluid and in the plasma are taken into account.

The control unit 12 calculates the initial set point of the substance in the dialysis fluid also as a function of the molar conductivities of one or more substances, such as one, two, three, or all of the following substances in the dialysis fluid which are sodium bicarbonate ($NaHCO_3$), sodium chloride (NaCl), sodium acetate ($NaCH_3COO$), trisodium citrate ($Na_3C_6H_5O_7$), potassium chloride (KCl), and sodium lactate ($Na_3C_3H_5O_3$).

The control unit 12 calculates the initial set point of the substance in the dialysis fluid as a function of an estimated plasma water concentration of at least sodium, and/or bicarbonate, and/or potassium and/or acetate and/or citrate. The estimated plasma water concentration of sodium, bicarbonate, potassium, acetate, and citrate, is, for example, the mean pre-dialysis values of the corresponding substance for large patient populations, or historical document for a particular patient.

In case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion.

In this case, the dilution of the plasma water concentration is a function of blood flow rate and infusion flow rate. Additionally, the dilution of the plasma water concentration is a function of the infusion fluid concentration of the specific substance (i).

The initial set point may also be a function of one or more flow rates, in particular of the dialysate flow rate at the outlet of the secondary chamber 4.

Also an efficiency parameter of the filtration unit 2 plays a role in the initial set point calculation of sodium. In particular a clearance $K_u$ of the filtration unit 2 may be used (e.g. the urea clearance).

Dialysis Fluid Starting Composition—HD Mode

Specifically in HD mode, the control unit 12 is configured to calculate the initial set point of sodium concentration to be set in the dialysis fluid before the start of the treatment using the following relationship:

$$c_{di,Na,start} = \alpha * c_{pw,Na} + \tag{19}$$
$$\frac{1}{M_{K_{NaCl}}}(M_{K_{NaHCO_3}} - M_{K_{NaCl}})\left(\frac{1}{\alpha} * c_{pw,HCO_3} - c_{di,HCO_3}\right) ++$$
$$\frac{1}{M_{K_{NaCl}}}(M_{K_{NaAc}} - M_{K_{NaCl}})\left(\frac{1}{\alpha} * c_{pw,Ac} - c_{di,Ac}\right) +$$
$$\frac{M_{K_{KCl}}}{M_{K_{NaCl}}}(\alpha * c_{pw,K} - c_{di,K}) ++ \frac{1}{M_{K_{NaCl}}}\frac{Q_{do}}{K_u}K_{rest3}$$

wherein the used symbols meaning is clarified in the glossary section.

In HD mode case, in case also citrate has to be taken into consideration, the control unit 12 may alternatively use the following relationship:

$$c_{di,Na,start} = \alpha * c_{pw,Na} + \tag{20}$$
$$\frac{1}{M_{K_{NaCl}}}(M_{K_{NaHCO_3}} - M_{K_{NaCl}})\left(\frac{1}{\alpha} * c_{pw,HCO_3} - c_{di,HCO_3}\right) ++$$
$$\frac{1}{M_{K_{NaCl}}}(M_{K_{NaAc}} - M_{K_{NaCl}})\left(\frac{1}{\alpha} * c_{pw,Ac} - c_{di,Ac}\right) +$$
$$\frac{M_{K_{KCl}}}{M_{K_{NaCl}}}(\alpha * c_{pw,K} - c_{di,K}) ++ \frac{K_{b_{Cit}}}{K_u}(M_{Na_3Cit} - M_{K_{NaCl}})$$
$$((0.167\alpha^{-3} + 0.125\alpha^{-2} + 0.706\alpha^{-1}) * c_{pw,Na_3Cit} - c_{di,Na_3Cit}) ++$$
$$\frac{1}{M_{K_{NaCl}}}\frac{Q_{do}}{K_u}K_{rest3}$$

wherein the used symbols meaning is clarified in the glossary section.

For $K_u$ calculations, see previous section.

Dialysis Fluid Starting Composition—HDF Post-Dilution Mode

In case of HDF post-dilution mode is selected, the same equations (19) and (20) apply. Differently from HD mode, dialyzer clearance $K_u$ is calculated for the HDF post-dilution mode with the substitution flow rate $Q_{inf}$ taken into account (see equations (4-8)).

Dialysis Fluid Starting Composition—HDF Pre-Dilution Mode

In case of HDF pre-dilution mode is selected, the dilution of the blood before it enters the dialyzer must be taken into account.

The equations for HDF pre-dilution are somehow similar to HDF post-dilution.

The dilution of the plasma water concentration of substance i in pre-dilution mode is described by the following equation:

$$c_{pw,bi} = \frac{Q_b * f_i * c_{pw,art} + Q_{inf} * c_{inf}}{Q_b * f_i + Q_{inf}} \quad (21)$$

wherein the used symbols meaning is clarified in the glossary section.

Thus, the plasma water concentrations for all substances is replaced with the corresponding diluted blood concentration as defined by the equation (21) above.

Also the "normal" Donnan factor $\alpha$ is replaced with Donnan factor $\alpha_{bi}$ calculated for the diluted protein concentration, as described in equations (17) and (18).

The dialyzable blood water fraction $f_i$ can be calculated with the equation:

$$f_i = f_{cw} \cdot \gamma_{cw,i} \cdot \text{Hct} + f_{pw} \cdot (1 - \text{Hct}) \quad (22)$$

wherein the used symbols meaning is clarified in the glossary section.

Of course, in HDF pre-dilution, the calculated isotonic or isonatric or isonatrikalemic sodium set point needs to be adjusted if the substitution fluid flow or blood flow is changed during treatment, since this changes the dilution of the blood compared to the conditions during the identification phase.

Specifically in HDF pre-dilution mode, the control unit 12 is configured to calculate the initial set point of sodium concentration to be set in the dialysis fluid before the start of the treatment using the following relationship:

$$c_{di,Na,start} = \quad (23)$$

$$\alpha_{bi} \cdot \frac{Q_b \cdot f_{Na} \cdot c_{pw,artNa}}{Q_b \cdot f_{Na} \cdot (1 - \alpha_{bi}) \cdot Q_{inf}} + + \frac{1}{M_{\kappa_{NaCl}}} \Big( (M_{\kappa_{NaHCO_3}} - M_{\kappa_{NaCl}})$$

$$\left( \frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - \right.$$

$$\left. c_{di,HCO_3} \right) + + (M_{\kappa_{NaAc}} - M_{\kappa_{NaCl}})$$

$$\left( \frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac} \right) + +$$

$$M_{\kappa_{KCl}} \cdot \left( \alpha_{bi} \cdot \frac{Q_b \cdot f_K \cdot c_{pw,artK} + Q_{inf} \cdot c_{di,K}}{Q_b \cdot f_K + Q_{inf}} - c_{di,K} \right) + +$$

$$\frac{K_{b,Cit}}{K_u} \cdot (M_{\kappa_{Na_3Cit}} - 3M_{\kappa_{NaCl}})$$

$$\left( (0.167 \alpha_{bi}^{-3} + 0.125 \alpha_{bi}^{-2} + 0.706 \alpha_{bi}^{-1}) \cdot \cdot \right.$$

$$\left. \frac{Q_b \cdot f_{Cit} \cdot c_{pw,artCit} + Q_{inf} \cdot c_{di,Cit}}{Q_b \cdot f_{Cit} + Q_{inf}} - c_{di,Na_3Cit} \right) +$$

$$\left. \frac{Q_{do}}{K_u} \kappa_{rest3} \right) \cdot \frac{Q_b \cdot f_{Na} + Q_{inf}}{Q_b \cdot f_{Na} + (1 - \alpha_{bi}) \cdot Q_{inf}}$$

Dialysis Fluid Starting Composition—HF Post-Dilution Mode

The equations for HF post-dilution mode are the same as for to HD, but the dialyzer clearance is substituted by the dialysate flow rate at filtration unit outlet, i.e. $K_u = Q_{do}$.

Dialysis Fluid Starting Composition—HF Pre-Dilution Mode

In case of HF pre-dilution mode is selected, the dilution of the blood before it enters the dialyzer must be taken into account.

The equations for HF pre-dilution are the same as for to HDF post-dilution, but the dialyzer clearance is substituted by the dialysate flow rate at filtration unit outlet, i.e. $K_u = Q_{do}$.

Of course, for each and every treatment mode, different mathematical relationships may be used taking into account exclusively some of the considered substances and/or exclusively some of the conductivities and/or molar differences.

Estimation of Isoconductivity

Once the sodium initial set point has been calculated (based on the selected HD/HDF/HF treatment mode and the above mathematical relationships) and a corresponding dialysis fluid has been prepared by the control unit 12 driving the regulating means 10, the treatment may start.

The dialysis fluid is prepared and then circulated through the dialysis fluid circuit 32. Depending on the selected treatment mode, the dialysis fluid is directed:
- to the secondary chamber 4 of the filtration unit 2 only so as to exchange with blood (HD mode);
- to the secondary chamber 4 of the filtration unit 2 so as to exchange with blood and infused into the blood circuit 17 (HDF mode);
- to the blood circuit only (HF mode); in this case an ultrafiltration flow rate is set to achieve a $Q_u = Q_{do}$.

Correspondingly, blood is withdrawn from the patient and circulated in the extracorporeal blood circuit 17 and particularly is circulated through the primary chamber 3 of the filtration unit 2.

At least one, and in general a plurality, of consecutive initial values of the parameter (in the specific example, the conductivity) of the dialysate downstream of the secondary chamber 4 are measured at the beginning of the treatment through sensor 11.

The post-dialyzer conductivity will change initially, due to e.g. dynamics when treatment is started (e.g. leaving bypass conditions) or when blood flow is ramped up. However, it is expected to stabilize within few (e.g. 4) minutes. The measurement is made as soon as certain stability criteria are fulfilled.

The set point calculated by the machine according to the previously disclosed equations includes the effect of glucose (if present in the concentrate) and thus the conductivity $\kappa_{di,start,set}$ has to be compensated for this accordingly to create the pure ion solution conductivity $\kappa_{0,di,start,set}$ which is to be used for the calculation.

The control unit 12 is configured to validate and further process the measurement of an initial value of the conductivity of the dialysate as soon as the diffusion process in the filtration unit 2 reaches stable conditions.

As mentioned, a transient exists when dialysis fluid and blood start exchanging during which the dialyzer outlet conductivity is not stable; during the transient period the measured outlet conductivity values should be disregarded.

Stable conditions for the diffusion process may be determined in case one or more of the following conditions occurs:
- a first derivative of the median or of the average value of the conductivity of the dialysate is lower in size than a first threshold;
- a first derivative of the value of conductivity of the dialysate is lower in size than a first threshold for a specified time window;
- a first derivative of the filtered value of conductivity of the dialysate is lower in size than a first threshold for a specified time window, the filtered value being a value filtered either by a median filter (which picks out the median) or a linear filter, either a finite impulse response filter (which is equal to a weighted average), or an infinite impulse response filter (which is standard, but has the form yf(t)=−a1*yf(t−1)− . . . −an*yf(t−n)+ b1*y(t−k−1)+ . . . +bm*y(t−k−m), where yf(t) is the filtered value at time t, y(t) is the measured value at time t, n and m are the number of parameters a and b (the order) of the filter and k is the number of pure time delays);

a second derivative of the median value of the conductivity of the dialysate is lower in size than a second threshold;

a second derivative of the filtered value of conductivity of the dialysate is lower in size than a first threshold for a specified time window;

a change or a relative change of the value itself or a filtered version of the value of the conductivity since a fixed previous point in time is below a first threshold (an expanding window);

a change or the relative change of the value itself or a filtered version of the value of the conductivity since a fixed time interval backwards is below a first threshold (a sliding window, constant in length);

a prefixed time has lapsed after starting circulation of both blood and fresh dialysis fluid in the filtration unit, in particular said pre-fixed time being not more than 15 minutes;

a variable time has lapsed after starting circulation of both blood and dialysis fluid in the filtration unit, said variable time being function of at least one parameter, such as the volume of the secondary chamber 4 of the filtration unit 2; in particular the variable time may be a function of further parameters such as dialysis fluid flow rate, blood flow rate, filtration unit permeability, etc. . . . .

The stability condition is preferably determined by observing, on a 1-minute window, the first derivative of $\kappa_{do}$ and checking when it is lower in size than a fixed threshold. Once this stability criterion is fulfilled, $\kappa_{do}$ is taken as the median value on the 1-minute window. The first derivative is used to avoid the presence of possible drifts in the outlet conductivity. Extracting the median and/or the average value of $\kappa_{do}$ allows discharging possible outliers of the outlet conductivity signal from the average calculation.

In order to minimize the time needed to reach stability conditions, changes in dialysis fluid flow rate and in bicarbonate prescription may be prevented during this preliminary isotonic sodium identification phase.

Changes in blood flow, ultrafiltration flow rate or bypass are vice versa generally allowed, but they will delay stability. Moreover, it is not possible to change the concentrate combination type after the treatment is started.

Alternatively, it might be possible to just estimate the initial value of the conductivity of the dialysate fluid representative of the conditions prevailing after the diffusion process has reached stable conditions; the estimate is based on one or more conductivity measurements in the dialysate before reaching the stable conditions and using proper estimate algorithms.

Glucose and urea, the main electrically neutral substances in dialysis fluid, reduce the conductivity of the dialysis fluid. The effect is small but noticeable and leads to a plasma conductivity underestimation and thus to an underestimation of the plasma sodium. Hence, a compensation for urea and glucose contribution may also be applied to the measured conductivities $\kappa_{di}$ and $\kappa_{do}$: the resulting conductivities for pure ion solutions ($\kappa_{0,di}$ and $\kappa_{0,do}$) may alternatively be used in all the calculations using conductivities reported below.

The control unit 12 may compensate the measured initial conductivity value of the dialysate as a function of the concentration of at least glucose.

Moreover, the control unit may compensate the measured initial conductivity value of the dialysate as a function of a flow rate, such as the dialysate flow rate at the outlet.

The control unit 12 may compensate the measured initial conductivity value of the dialysate as a function of an efficiency parameter of the filtration unit 2, (e.g. a clearance of the filtration unit 2, in detail the urea clearance).

Furthermore, the control unit 12 may compensate the measured initial conductivity value of the dialysate as a function of an estimated plasma concentration of glucose and/or urea.

The specific formula to compensate the measured initial conductivity value of the dialysate is the following:

$$\kappa_{0,do} = \frac{\kappa_{do}}{\left(1 - \gamma_g * \left(c_{di,g} + \frac{f_{g,K_B} K_u}{Q_{do}}\left(\frac{c_{p,g}}{f_{pw}} - c_{di,g}\right)\right)\right)\left(1 - \gamma_u \frac{K_u}{Q_{do}} \frac{c_{p,u}}{f_{pw}}\right)} \quad (24)$$

The significance of the denotations and constants above is given in the Glossary.

The estimated values of dialyzer clearance $K_u$ and plasma water fraction $f_{pw}$ depend on the selected treatment mode (HD/HDF/HF) and should be calculated as described in the previous sections (see eq. (13) and (15)).

Moreover, in HDF and HF pre-dilution mode, the plasma concentrations of glucose and urea $c_{p,g}$ and $c_{p,u}$ must be replaced with the corresponding diluted concentrations (see eq. (17)).

The control unit 12 may be configured to compensate the initial conductivity of the dialysis fluid as a function of the concentration of glucose, if glucose is present in the dialysis liquid.

The control unit 12 is specifically configured to compensate the initial conductivity of the fresh dialysis fluid using the following formula:

$$\kappa_{0,di} = \frac{\kappa_{di}}{1 - \gamma_g c_{di,g}} \quad (25)$$

The significance of the denotations and constants above is given in the Glossary.

It is worth to note that the initial conductivity of the fresh dialysis fluid upstream the secondary chamber 4 may be either measured or taken as the set value for dialysis conductivity.

In general, it is preferred to measure the initial conductivity of the dialysis fluid through the sensor 35, too.

It is important to underline that the initial setting of the sodium concentration calculated or determined as above stated to be as close as possible to the expected plasma conductivity (eq. 1) may be optional, meaning that the method for estimating the initial plasma conductivity may be performed even if the sodium content of the dialysis conductivity is initially simply set by the operator.

Also correction based on main electrically neutral substances is optional and may be used or not to increase accuracy.

The compensation for the main electrically neutral substances (e.g. urea and glucose) may be alternatively applied to the final adjustment contribution terms.

Vice versa, it is relevant to measure at least the conductivity downstream the filtration unit (and preferably also the conductivity upstream the filtration unit) as soon as possible, i.e. as soon as stable conditions are reached or as soon as an estimate of such conductivity in stable conditions may be performed.

This is due to the need of matching as much as possible the patient initial plasma conductivity which is clearly affected/changed by the different conductivity of the dialysis fluid circulating during the treatment.

In order to make a first estimate of the plasma conductivity based on measured values, two embodiments are provided, which may be used together or alternatively.

Firstly, the control unit 12 calculates the value of the initial plasma conductivity, based on the measured initial parameter value of the dialysate (i.e. based on conductivity or concentration measurement of dialysate on the filtration unit outlet) and on the corresponding parameter value of the dialysis fluid in the dialysis fluid supply line 8 e.g. conductivity or concentration). During the start of the treatment and particularly during circulating the dialysis fluid through the secondary chamber 4 and/or in the infusion line 39 up to measuring the initial value of the parameter of the dialysate downstream of the secondary chamber used for the calculating of the initial plasma conductivity, the dialysis fluid conductivity (or concentration) is kept substantially constant.

In other words, the calculation of the initial plasma conductivity is performed with no conductivity step as it was normally made in the prior art devices.

Indeed, both the two embodiments allowing plasma conductivity estimation do not require to change the dialysis conductivity or the sodium content in the dialysis liquid and to take measures at the inlet and at the outlet of the dialyzer in both conditions.

In this respect the term 'substantially constant' means that the conductivity of the dialysis fluid is not changed by the machine or by the operator, but it may not be exactly constant due to small oscillations on the measured value caused by noise, tolerances in the concentrate dosing system or tolerances in the conductivity measurements. Generally these small variations around the set value are less than 0.2 mS/cm.

Just a single reliable measurement at the inlet and at the outlet of the dialyzer may be sufficient to have a preliminary (to be made more accurate) or an already final estimation of the PC.

From a general point of view, the control unit 12 is further configured to calculate the plasma conductivity as a function of at least one or more flow rates.

The flow rates include the dialysate flow rate at the outlet of the secondary chamber 4; in addition, the flow rates may include the blood flow rate in the blood lines too.

Also an efficiency parameter of the filtration unit 2, in particular a clearance of the filtration unit 2 (e.g. the urea clearance) is used for plasma conductivity. Of course, a nominal clearance and/or a calculated clearance may be used; the calculated clearance may be both an estimated clearance as well as a compensated clearance.

Moreover, the plasma conductivity depends on an (possibly compensated) initial conductivity of the dialysate and on a (possibly compensated) conductivity of the dialysis fluid in the dialysis supply line 8.

According to a first embodiment, the control unit 12 is programmed to calculate the initial plasma conductivity based on the sum of at least the initial conductivity of the dialysate plus a difference between inlet and outlet conductivity at the filtration unit, or dialyzer, weighted by a factor of the dialysate flow rate. In more detail the difference between inlet and outlet conductivity at the dialyzer is weighted by a factor of the blood flow rate in the blood lines too.

Specifically, according to the first embodiment, the control unit 12 is configured to calculate the plasma conductivity using the following formula:

$$\kappa'_{p,1} = \kappa_{0,do} + \frac{Q_{do}}{Q_{Bset}}(\kappa_{0,do} - \kappa_{0,di}) \tag{26}$$

The significance of the denotations above is given in the Glossary.

It is worth to underline that during the above described calculation of the initial plasma conductivity (formula (26)), the dialysis fluid circulates through the secondary chamber 4 and/or is infused into the blood circuit 17 (depending on selected HD/HF/HDF mode) maintaining the dialysis fluid parameter value substantially constant.

In the second embodiment, the control unit 12 is programmed to calculate the initial plasma conductivity based on the sum of at least the initial conductivity of the fresh dialysis fluid plus a difference between inlet and outlet conductivity at the dialyzer weighted by a factor of the dialysate flow rate. In more detail the difference between inlet and outlet conductivity at the filtration unit, or dialyzer, is weighted by a factor of the dialyzer clearance too.

Specifically, according to the second embodiment, the control unit 12 is configured to calculate the plasma conductivity using the following formula:

$$\kappa''_{p,1} = \kappa_{0,di} + \frac{Q_{do}}{K_u}(\kappa_{0,do} - \kappa_{0,di}) \tag{27}$$

The significance of the denotations and constants above is given in the Glossary.

It is worth to underline that during the above described calculation of the initial plasma conductivity (formula (27)), the dialysis fluid circulates through the secondary chamber 4 and/or is infused into the blood circuit 17 (depending on selected HD/HF/HDF mode) maintaining the dialysis fluid parameter value substantially constant.

In more detail, in the formulas above:

$k_{0,di}$ is the set/measured-by-sensor 35 value for conductivity of the dialysis fluid, corrected for glucose (see previous equation);

$k_{0,do}$ is the mean value of outlet conductivity on the stability 1-minute window, corrected for glucose and urea;

$Q_{bset}$ and $Q_{do}$ are the mean values, respectively, of blood flow rate set and of dialysate flow rate at the filtration unit, or dialyzer, outlet, on the stability window;

$K_u$ is the dialyzer diffusive clearance for urea (to be determined according to the treatment mode and respective equation—previously described)

According to first estimate, $k_{p,1}$ may be found after approx. 6 to 10 minutes after treatment start.

Of course, both formulas (26) and (27) for estimation of plasma conductivity may be iteratively applied, meaning that the newly calculated estimate of PC ($k_{p,1}$) is imposed to the dialysis fluid and a new estimate ($k_{p,2}$) again calculated after taking measures of the conductivity at the inlet and outlet of the filter as soon as stable conditions are reached.

Of course, in case of iteration of anyone of the above calculations according to formulas (26) or (27), after the first plasma conductivity estimation, the dialysis fluid parameter value is changed since the newly calculated estimate of PC ($k_{p,1}$) is imposed to the dialysis fluid, meaning that the conductivity of the dialysis fluid is changed. This however does not impact on the fact that the first calculation according to formulas (26) and (27) is made without a change in the conductivity of the dialysis fluid.

In one way of exploiting the method, the first formula (26) or the second formula (27) is applied only once and the estimated PC ($k_{p,1}$) is considered already a good estimation of initial plasma conductivity.

In another way, the first formula (26) is applied twice.

In a further way, the second formula (27) is applied twice; in this case, the dialysis fluid sodium concentration correspondent to $k_{p,1}$ is iteratively calculated and applied. $k_{do}$ is measured again as soon as stable conditions are reached: the stability criteria are the same as previously described. A second estimation of PC ($k_{p,2}$) according to formula (27) is done and $k_{p,2}$ is used as $k_{p,pre}$.

In this second case $k_{p,2}$ should be found after approx. 11-17 minutes after treatment start.

Figure 3:
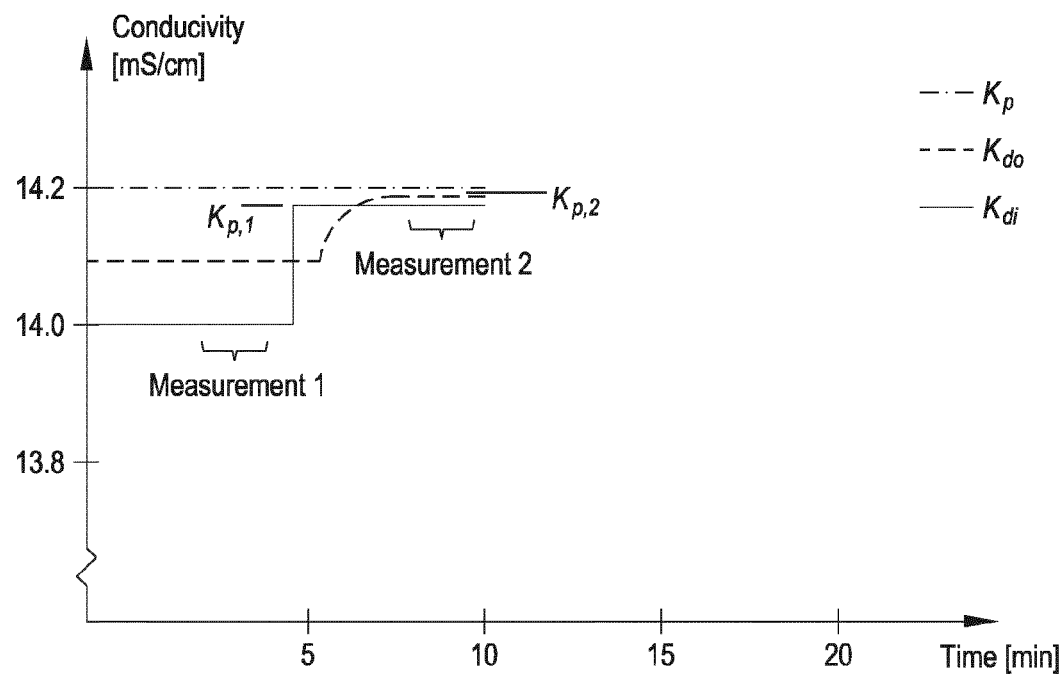
FIG. 3 is a diagram showing dialysis fluid and dialysate conductivity values at the start of the treatment when performing a calculation according to an embodiment of the invention.

The above mentioned steps according to one of the described embodiment are schematically shown in FIG. 3.

It is relevant to note that in equations (26) and (27), $k_{do}$ and $k_{di}$ may be used instead of $k_{0,do}$ and $k_{0,di}$.

A timeout may be provided for each of $k_{p,1}$ and $k_{p,2}$ estimation phases (due to e.g. a change in some parameters). At the end of either one of these timeouts (e.g., if the stability has not been reached), an alarm shall be triggered to de-activate the isotonic treatment procedure. In general it does not make sense to apply isotonic dialysis too late into the treatment.

The dialysis fluid sodium concentration correspondent to $k_{p,pre}$ is then determined.

The resulting dialysis fluid sodium concentration applied, $c_{di,Na, kp,pre}$, would correspond to implement an isoconductive dialysis.

In summary, the proposed method of estimating isoconductivity at the beginning of treatment is done through the following main steps:
1. Set the dialysis fluid conductivity $k_{di,start}$ to be as close to the isoconductivity as possible before treatment start. This is done by calculating a start sodium concentration based on average data from a large patient population;
2. Measure dialysis fluid conductivity upstream and downstream the dialyzer ($k_{0di}$ and $k_{0do}$) as soon as stable conditions have been reached after treatment start;
3. Make a first estimate of the isoconductivity $k_{p,1}"$ from the measured difference between $k_{0di}$ and $k_{0do}$;
4. Set $k_{0di}$ equal to $k_{p,1}"$;
5. Measure dialysis fluid conductivity upstream and downstream the dialyzer ($k_{0di}$ and $k_{0do}$) again, calculate a second estimate $k_{p,2}$
6. Use $k_{p,2}$ second estimate as an estimate of $k_{p,pre}$.

Setting of the Dialysis Fluid Sodium Concentration

The starting point for setting the individualized sodium concentration is isoconductive dialysis, i.e., when pre and post dialyzer conductivities are equal. This is achieved when the dialysis fluid conductivity has been set to the estimated pre-dialysis isoconductivity.

The dialysis fluid sodium concentration shall then be set to provide either isotonic, isonatric or isonatrikalemic treatment based on determined dialysis fluid conductivity for isoconductive dialysis.

The setting can be done either as an adjustment in conductivity set point or as an adjustment in sodium set point, but a sodium set point change is chosen as main implementation.

Since an isotonic or isonatric or isonatrikalemic dialysis is to be applied, this sodium value may be adjusted with a proper adjustment factor (depending on the selected treatment mode—HF/HDF/HD—and depending on the choice to apply isotonic, isonatric or isonatrikalemic dialysis).

In respect to the above mentioned treatments, it is relevant to note the following.

An isonatric dialysis may in general terms be considered as a treatment where the sodium concentration in the extracellular fluid of the patient is maintained stable or undergoes reduced variations throughout treatment.

It is however worth noting that tonicity is determined by the particles that are osmotically active.

Actually, the dialysis fluid (and the plasma) contains a multitude of substances that influence tonicity/osmolality, not just sodium, even if this is the main determinant of serum osmolality.

Hence, an isotonic dialysis may be considered as a dialysis where the tonicity of the fluids in the patient is maintained stable or undergoes reduced variations throughout dialysis treatment. This would be achieved by maintaining the tonicity of the dialysis fluid substantially equal to the tonicity of the extracellular fluid throughout treatment. In this case, the tonicity of the dialysis fluid does not change pre- to post-filtration unit 2.

An isonatrikalemic dialysis, may in general terms be considered as a treatment where the sum of sodium and potassium concentrations in the patient extracellular fluid is maintained stable or undergoes reduced variations throughout dialysis treatment (in this case, the sum of sodium and potassium concentrations of the dialysis fluid does not change pre- to post-filtration unit 2). Considering that a patient shall lose a certain amount of potassium during treatment, the isonatrikalemic condition may be maintained with a proportional increase in serum sodium concentration.

An isoconductive dialysis may in general terms be considered as a dialysis treatment maintaining the conductivity of the dialysis fluid equal to the conductivity of the extracellular fluid, which in this case is represented by the plasma conductivity.

The plasma conductivity (PC, $\kappa_p$) is the conductivity at which the dialysis fluid conductivity is not changed during its passage through the dialyzer. Then the conductivities upstream and downstream the filtration unit 2 are equal: $\kappa_{di}=\kappa_{do}$.

In case of an isotonic or isonatric or isonatrikalemic treatment is to be performed, the mentioned adjustment factor is calculated based on molar conductivities, dialysis fluid composition, and the best estimate of plasma water composition as will better emerge from the following description. The best estimate of plasma water composition may be derived from literature, or may be based on statistical prepared values, or test of patient, or obtained with direct lab measurements made before the treatment.

According to an innovative aspect, the control unit 12 receives a value representative of a parameter of the blood in said blood lines 6, 7. The blood parameter may be the plasma conductivity or a plasma conductivity-related parameter.

In particular, the control unit 12 may be programmed for calculating the plasma conductivity, for example executing the method previously disclosed or, alternatively using known methods such as those described in EP 2377563.

Alternatively, the control unit 12 directly receives as an input the plasma conductivity. For example, the physician or the nurse may receive a lab analysis and may provide the datum to the machine through the user interface of the dialysis monitor; the control unit 12 is programmed for storing in a memory the plasma conductivity to be used for the following dialysis fluid parameter regulation.

Finally, the plasma conductivity may be directly measured in vivo by the monitor before starting the treatment session using a proper plasma conductivity sensor.

The control unit 12 is generally configured for setting a parameter value for the dialysis fluid in the dialysis supply line 8 at a set point.

The parameter of the dialysis fluid is chosen between a conductivity of the dialysis fluid, a conductivity-related parameter of the dialysis fluid, a concentration of a substance in the dialysis fluid and a concentration-related parameter of a substance in the dialysis fluid.

Depending on the specific dialysis monitor, the sodium content (or the content of more than one electrolyte) may be regulated in the dialysis line. Alternatively, the control parameter may be the overall conductivity of the dialysis fluid.

The setting of the parameter value in the dialysis fluid (which is hereinafter identified as sodium concentration set point in the dialysis fluid with no limiting effect) includes the sub-step of calculating the sodium concentration set point (at least) as a function of a main contribution term based on/function of the plasma conductivity and as a function of an adjustment contribution term, i.e. a term which takes into account the transport driving gradient of certain specific substances. Additionally, compensation for unwanted sodium transfer may be applied as explained in detail in the last paragraphs of the present description.

The main contribution term may affect (may contribute to) the dialysis fluid sodium concentration set point for at least 80% of the same parameter value (and in particular for at least 90% of the parameter value), i.e. the general value of the sodium concentration mainly depend on plasma conductivity.

In more detail, the adjustment contribution term may contribute to the dialysis fluid sodium concentration set point for less than 15% of the same parameter value (and in particular for less than 10% of the parameter value).

The calculation is an algebraic sum of at least the main contribution term ($C_{di,Na,\kappa_{p,pre}}$) and the adjustment contribution term ($C_{di,Na,adj}$) according to the following general formula:

$$c_{di,Na,set} = c_{di,Na,\kappa_{p,pre}} + c_{di,Na,adj} \qquad (28)$$

In order to obtain a dialysis fluid sodium implementing a certain kind of dialysis, i.e. $C_{di,Na,set}$, a adjustment factor $C_{di,Na,adj}$ needs to be applied to make the dialysis fluid matching a certain specific concentration of the plasma.

($c_{di,Na,K_{p,pre}}$) is the dialysis fluid concentration of sodium at isoconductive state, i.e. when the dialysis fluid conductivity $\kappa_{di}$ matches the estimated pre-dialysis plasma conductivity $K_{p,pre}$.

Though not essential since a calculation may be made based on conductivities too, the main contribution term and the adjustment contribution term are dimensionally concentrations of a substance (e.g. sodium) in a fluid.

The adjustment contribution term is the sodium concentration set point adjustment relative to an isoconductive state to provide a specific treatment which may be, for example, chosen in the group including isotonic dialysis, isonatric dialysis, and isonatrikalemic dialysis.

The Applicant has understood that certain specific substances, namely bicarbonate, potassium, acetate, and citrate have a major effect which should be taken into account when it is desired to run an isotonic, or isonatric, or isonatrikalemic dialysis treatment.

Indeed, an isoconductive dialysis (i.e. a dialysis maintaining the conductivity of the dialysis fluid equal to the conductivity of the extracellular fluid, which in this case is represented by the plasma conductivity—as defined, plasma conductivity (PC, $\kappa_p$) as the conductivity at which the dialysis fluid conductivity is not changed during its passage through the dialyzer so that the pre-dialyzer and the post-dialyzer conductivities are equal: $\kappa_{di} = \kappa_{do}$) causes an overload of sodium in the patient.

To avoid overloading at least the effect of the above substances must be taken into duly consideration. Of course other substances play a role, such as lactate, magnesium, and calcium.

Furthermore, the difference in concentration between same substances in the blood and in the dialysis fluid influences, as well, the sodium overload in case of isoconductive treatments.

Given the above, the Applicant also realized that in calculating the adjustment contribution term, certain parameters having a weight in determining the overload of sodium are known and depends on the machine dressing (e.g. used concentrates) or on the prescription for the patient (e.g. dialysate flow rate). Other parameters depend on the patient undergoing the treatment and therefore may be either directly measured (e.g. lab analysis) or estimated (e.g. based on large population numbers or patient history).

Since isoconductive dialysis causes sodium overload, the adjustment contribution term generally assumes a negative value, i.e. reduces the set point concentration of sodium in the dialysis fluid calculated for isoconductive treatment.

In more detail, the control unit is configured to calculate the adjustment contribution term based on a concentration of at least a substance in the dialysis fluid chosen in the group including bicarbonate, potassium, acetate, lactate, and citrate; in particular calculation is made as a function of the concentration of at least two of said substances, and in further detail as a function of the concentration of bicarbonate, potassium, acetate, and/or citrate, and lactate in the dialysis fluid.

As mentioned, the control unit is configured to calculate the adjustment contribution term as a function of the difference, in particular weighted difference, in concentration of at least one of the above cited substances in the dialysis fluid and the same substances in the blood plasma.

In case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion.

Additionally, the control unit calculates the adjustment contribution term as a function of the molar conductivities of at least a substance in the dialysis fluid; in detail the substance may be chosen from the group including acids or salts of bicarbonate, chloride, acetate, phosphate, and sulphate, wherein the salt is formed with sodium, potassium, calcium, or magnesium.

In more detail, the calculations take into account the molar conductivities of at least two of said substances, specifically of at least three and particularly of sodium bicarbonate (NaHCO$_3$), sodium chloride (NaCl), sodium acetate (NaCH$_3$COO), trisodium citrate (Na$_3$C$_6$H$_5$O$_7$), and potassium chloride (KCl).

Again, the adjustment contribution term is a function of the differences between two molar conductivities, a first molar conductivity of a substance chosen in the group including sodium bicarbonate (NaHCO$_3$), sodium acetate (NaCH$_3$COO), trisodium citrate (Na$_3$C$_6$H$_5$O$_7$), and potassium chloride (KCl), and a molar conductivity of sodium chloride (NaCl).

Alternatively, the adjustment contribution term is a function of the differences between two molar conductivities, a first molar conductivity of a substance chosen in the group including sodium bicarbonate (NaHCO$_3$), trisodium citrate (Na$_3$C$_6$H$_5$O$_7$), and potassium chloride (KCl), and a molar conductivity of sodium chloride (NaCl).

The control unit is also configured to calculate the adjustment contribution term as a function of an estimated plasma water concentration of at least a substance in blood entering the dialyzer; the substance is chosen in the group including bicarbonate, potassium, acetate, lactate, and citrate; in particular the calculation is made based on the estimated plasma water concentration of at least two, three or four of said substances; in the specific example of the present description the adjustment contribution term is a function of the estimated plasma water concentration of bicarbonate, potassium, and acetate or is a function of the estimated plasma water concentration of bicarbonate, potassium, citrate, and acetate.

In HD, HDF post-dilution and HF post-dilution, the estimated plasma water concentration of bicarbonate, potassium, citrate, and acetate is the mean pre-dialysis values of the corresponding substance for large patient populations. As previously mentioned, the estimated plasma water concentration of bicarbonate, potassium, and acetate may alternatively be based on other statistical prepared values, or historical values for the specific patient, or direct measurements made before the treatment.

In respect to HDF pre-dilution and HF pre-dilution, the estimated plasma water concentration in blood entering the dialyzer takes into account the dilution of the blood due to the infusion of substitution fluid upstream the dialyzer.

The estimated plasma water concentration in HDF pre-dilution and HF pre-dilution modes is a function of the blood flow rate $Q_b$ and of the infusion flow rate $Q_{inf}$. Furthermore, it is also function of the dialyzable blood water fraction for the selected substance (calculated based on hematocrit—Hct—and cell water fraction) and of the plasma water concentration in blood from patient (i.e. upstream the pre-dilution infusion point); the estimated plasma water concentration is also function of the infusion fluid concentration of the same substance.

Note that, in the specific formula, the estimated plasma water concentration is adjusted by a respective (preferably, but not necessarily, fixed) adjusting factor. Numerical values can be, e.g. 0.95 or 1.05, but other values may be used (generally depending on the protein content, or charge of ions).

More in detail, the adjusting factor is function of the charged plasma proteins, and particularly of the Donnan factor. In HD, HDF post-dilution and HF post-dilution modes, the adjusting factor is the Donnan factor $\alpha$ or its reciprocal $\alpha^{-1}$. In HDF pre-dilution and HF pre-dilution modes, the adjusting factor should take into consideration the reduction of total protein concentration due to pre-dilution infusion. Therefore, the adjusting factor is in this latter case function of the diluted protein concentration affected by blood flow $O_b$, infusion flow $Q_{inf}$, and red cell fraction of blood Hct (see e.g. equation (14)).

The adjustment contribution term is an algebraic sum of a plurality of components, a first component being function of the difference, in particular weighted difference, in concentration of at least a substance in the dialysis fluid and the same substance in the blood plasma, the second component being function of the difference, in particular weighted difference, in concentration of at least a second substance in the dialysis fluid and the same second substance in the blood plasma, the third component being function of the difference, in particular weighted difference, in concentration of at least a third substance in the dialysis fluid and the same third substance in the blood plasma, optionally the fourth component being function of the difference, in particular a weighted difference, in concentration of at least a fourth substance in the dialysis fluid and the same fourth substance in the blood plasma, the fifth component depends on at least a ratio between one flow rate, in particular the dialysate flow rate at the outlet of the secondary chamber 4, and an efficiency parameter of the filtration unit 2, in particular a clearance of the filtration unit 2, optionally the urea clearance.

The substance may be chosen in the group including bicarbonate anions (HCO$_3^-$), acetate anions (CH$_3$COO$^-$), citrate anions (C$_6$H$_5$O$_7^{3-}$), and potassium ions (K$^+$), but additionally also lactate.

Again, in case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion. Therefore, the difference above mentioned is a difference between a diluted blood concentration and the concentration in the dialysis fluid of the same substance.

The above general consideration is reflected in specific and non-limiting implementing formulas which allow, when the plasma conductivity is known, to determine the precise set point for sodium concentration in the dialysis fluid for running an isotonic, isonatric or isonatrikalemic treatment.

Of course, different formulas including one or more of the general principles/substances above stated may be alternatively used.

Isotonic Dialysis

In order to obtain a dialysis fluid sodium implementing isotonic dialysis, i.e. $c_{di,Na,set,isotonic}$, an adjustment factor $c_{di,Na,isotonic,adj}$ needs to be applied to make the dialysis fluid matching the tonicity of the plasma:

$$c_{di,Na,set,isotonic} = c_{di,Na,\kappa_{p,pre}} + c_{di,Na,isotonic,adj} \quad (29)$$

Isotonic Dialysis—HD Treatment Mode

In case of HD treatment mode:

$$c_{di,Na,isotonic,adj} = \qquad (30)$$
$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right) + \right.$$
$$(M_{\kappa_{NaAc}} - M_{\kappa_{NaCl}})\left(\frac{1}{\alpha} * c_{pw,Ac} - c_{di,Ac}\right) + +$$
$$\left. (M_{\kappa_{KCl}} - M_{\kappa_{NaCl}})(\alpha * c_{pw,K} - c_{di,K}) + \frac{Q_{do}}{K_u}(\kappa_{rest1} + \kappa_{rest2})\right)$$

or where the adjustment factor also takes care of citrate according to the following relationship:

$$c_{di,Na,isotonic,adj} = \quad (31)$$

$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right) + \right.$$

$$(M_{\kappa_{NaAc}} - M_{\kappa_{NaCl}})\left(\frac{1}{\alpha} * c_{pw,Ac} - c_{di,Ac}\right) + + (M_{\kappa_{KCl}} - M_{\kappa_{NaCl}})$$

$$(\alpha * c_{pw,K} - c_{di,K}) + + \frac{K_{b_{Cit}}}{K_u}(M_{Na_3Cit} - M_{\kappa_{NaCl}})$$

$$((0.167\alpha^{-3} + 0.125\alpha^{-2} + 0.706\alpha^{-1}) * c_{pw,Na_3Cit} -$$

$$\left. c_{di,Na_3Cit}) + + \frac{Q_{do}}{K_u}(\kappa_{rest1} + \kappa_{rest2})\right)$$

$K_{b_{Cit}}$ is the approximated clearance value for citrate. This clearance is calculated for the actual flow rates using a mass transfer value of $K_0A_{Cit}=0.212*K_0A_{Urea}$ in the corresponding $K_u$ formula.

Figure 4:
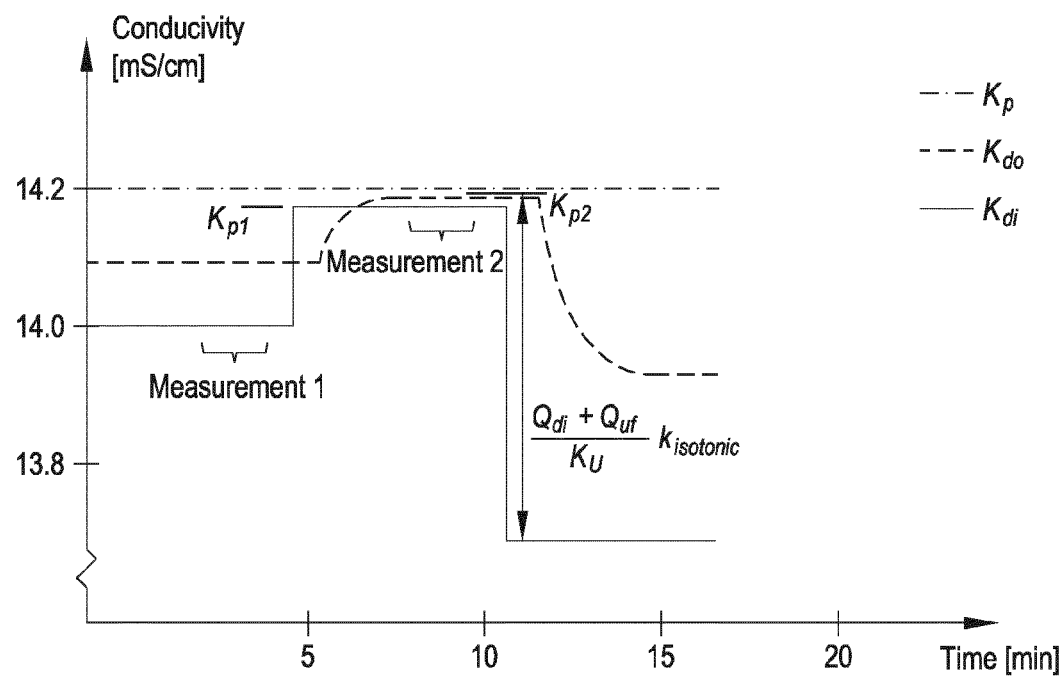
FIG. 4 is a diagram showing dialysis fluid and dialysate conductivity values after adjusting sodium concentration in dialysis fluid to run an isotonic dialysis treatment.

FIG. 4 shows the conductivity values upstream and downstream the dialyzer after setting the fresh dialysis fluid sodium concentration for running an isotonic dialysis treatment.

It is worth to mention that the plasma conductivity might be also measured using conductivity steps and applying the methods described in publications n. EP 547025 and/or in EP 920877. This alternative or additional estimation of plasma conductivity may further improve the plasma conductivity estimation made with the previously described technique.

Factor k (namely, $k_{rest1}$, $k_{rest2}$, and $k_{rest3}$—see also the following formulas) defines the effect on the conductivity due to other components in the dialysis fluid different from the components already treated and included in the respective formula. Thus, the effect of salts containing calcium, magnesium, lactate, phosphate, and sulphate may have upon the conductivity. The effect created by these components is most often small, and does not vary considerably between the dialysis treatments.

Isotonic Dialysis—HDF Post-Dilution Treatment Mode

In case of HDF treatment mode post-dilution, the same equations (30), (31) as for HD treatment mode applies, but with the clearance $K_u$ calculated for the HDF treatment case with the substitution flow rate taken into account (see equations (4-8)).

Isotonic Dialysis—HDF Pre-Dilution Treatment Mode

The equations for HDF pre-dilution are similar to HDF post, but we must take into account the dilution of the blood before it enters the dialyzer.

The dilution of the plasma water concentration of substance 1 in pre-dilution mode is described by equation (21) here-below reported for ease of comprehension:

$$c_{pw,bi} = \frac{Q_b \cdot f_i \cdot c_{pw,art} + Q_{inf} \cdot c_{inf}}{Q_b \cdot f_i + Q_{inf}} \quad (21)$$

The adjustment factor is calculated as follows:

$$c_{di,Na,isotonic,adj} = -\frac{1}{M_{\kappa_{NaCl}}}\left((M_{\kappa_{NaHCO_3}} - M_{\kappa_{NaCl}}) \right. \quad (32)$$

$$\left(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\right) + +$$

-continued $$(M_{\kappa_{NaAc}} - M_{\kappa_{NaCl}}) \cdot$$

$$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right) + +$$

$$(M_{\kappa_{HCl}} - M_{\kappa_{NaCl}}) \cdot$$

$$\left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right) + +$$

$$\frac{K_{b,Cit}}{K_u} \cdot (M_{\kappa_{Na_3Cit}} - M_{\kappa_{NaCl}})$$

$$\left((0.167\alpha_{bi}^{-3} + 0.125\alpha_{bi}^{-2} + 0.706\alpha_{bi}^{-1}) \cdot \cdot \right.$$

$$\frac{Q_b \cdot f_{Cit} \cdot c_{pwm,artCit} + Q_{inf} \cdot c_{di,Cit}}{Q_b \cdot f_{Cit} + Q_{inf}} -$$

$$\left. c_{di,Na_3Cit}\right) + + \frac{Q_{do}}{K_u}(\kappa_{rest1} + \kappa_{rest2})\right)$$

Isotonic Dialysis—HF Pre-Dilution Treatment Mode

The equations for HF pre-dilution are the same equations as HDF pre-dilution, but with the filtration unit clearance equal to dialysate flow rate at filtration unit outlet, i.e. $K_u=O_{do}$.

Isotonic Dialysis—HF Post-Dilution Treatment Mode

The equations for HF post-dilution are the same equations as HD, but with the filtration unit clearance equal to dialysate flow rate at filtration unit outlet, i.e. $K_u=Q_{do}$.

Isonatric Dialysis

In order to obtain a dialysis fluid sodium implementing isonatric dialysis, i.e. $C_{di,Na,set,isoNa}$, an adjustment factor $c_{di,Na,isoNa,adj}$ needs to be applied to make the sodium concentration of dialysate out from the dialyzer matching the sodium concentration of dialysis fluid at the inlet of the dialyzer:

$$c_{di,Na,set,isoNa} = c_{di,Na,\kappa_{p,pre}} + c_{di,Na,isoNa,adj} \quad (33)$$

Isonatric Dialysis—HD Treatment Mode

In case of HD treatment mode:

$$c_{di,Na,isoNa,adj} = \quad (34)$$

$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right) + \right.$$

$$(M_{\kappa_{NaAc}} - M_{\kappa_{NaCl}})\left(\frac{1}{\alpha} * c_{pw,Ac} - c_{di,Ac}\right) + +$$

$$\left. M_{\kappa_{KCl}}(\alpha * c_{pw,K} - c_{di,K}) + \frac{Q_{do}}{K_u}\kappa_{rest3}\right)$$

Where the adjustment factor also takes care of citrate, the adjustment factor is calculated according to the following relationship:

$$c_{di,Na,isoNa,adj} = \quad (35)$$

$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right) + \right.$$

$$(M_{\kappa_{NaAc}} - M_{\kappa_{NaCl}})\left(\frac{1}{\alpha} * c_{pw,Ac} - c_{di,Ac}\right) + +$$

$$\frac{K_{b_{Cit}}}{K_u}(M_{Na_3Cit} - 3M_{\kappa_{NaCl}})$$

-continued
$$((0.167\alpha^{-3} + 0.125\alpha^{-2} + 0.706\alpha^{-}) * c_{pw,Na_3Cit} -$$
$$c_{di,Na_3Cit}) + + M_{\kappa_{KCl}}(\alpha * c_{pw,K} - c_{di,K}) + \frac{Q_{do}}{K_u}\kappa_{rest3}\bigg)$$

For $K_{b_{Cit}}$ calculation see above.

Isonatric Dialysis—HDF Post-Dilution Treatment Mode

In case of HDF treatment mode post-dilution, the same equations ... as for HD treatment mode applies, but with the clearance $K_u$ calculated for the HDF treatment case with the substitution flow rate taken into account (see equations (4-8)).

Isonatric Dialysis—HDF Pre-Dilution Treatment Mode

The equations for HDF pre-dilution are similar to HDF post, but we must take into account the dilution of the blood before it enters the dialyzer.

The adjustment factor is calculated as follows:

$$c_{di,Na,isoNa,adj} = -\frac{1}{M_{\kappa_{NaCl}}}\bigg((M_{\kappa_{NaHCO_3}} - M_{\kappa_{NaCl}}) \quad (36)$$

$$\bigg(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\bigg) + +$$

$$(M_{\kappa_{NaAc}} - M_{\kappa_{NaCl}})$$

$$\bigg(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\bigg) + +$$

$$M_{\kappa_{KCl}} \cdot \bigg(\alpha_{bi} \cdot \frac{Q_b \cdot f_K]c_{pw,artK} + Q_{inf} \cdot c_{di,K}}{Q_b \cdot f_K + Q_{inf}} - c_{di,K}\bigg) + +$$

$$\frac{K_{b,XCit}}{K_u} \cdot (M_{\kappa_{Na_3Cit}} - 3M_{\kappa_{NaCl}})$$

$$\bigg((0.167\alpha_{bi}^{-3} + 0.125\alpha_{bi}^{-2} + 0.7066_{bi}^{-1}) \cdot \cdot$$

$$\frac{Q_b \cdot f_{Cit} \cdot c_{pw,artCit} + Q_{inf} \cdot c_{di,Cit}}{Q_b \cdot f_{Cit} + Q_{inf}} -$$

$$c_{di,Na_3Cit}\bigg) + + \frac{Q_{do}}{K_u}K_{rest3}\bigg)$$

Isonatric Dialysis—HDF Pre- and Post-Dilution Treatment Mode

It is also possible to handle combined pre and post treatment modes. The infusion flow $Q_{inf}$ is divided into two parts $Q_{inf,pre}$ and $Q_{inf,post}$, wherein $$Q_{inf} = Q_{inf,pre} + Q_{inf,post} \quad (37)$$

General formulas covers combinations and pure pre- and post-dilution as special cases. In this case the adjustment factor can be calculated as follows:

$$c_{di,Na,isoNa,adj} = -\frac{1}{M_{\kappa_{NaCl}}}\bigg((M_{\kappa_{NaHCO_3}} - M_{\kappa_{NaCl}}) \quad (38)$$

$$\bigg(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\bigg) + +$$

$$(M_{\kappa_{NaAc}} - M_{\kappa_{NaCl}})$$

$$\bigg(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\bigg) + +$$

$$(M_{\kappa_{KCl}}) \cdot \bigg(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\bigg) + +$$

-continued
$$\frac{K_{b,Cit}}{K_u} \cdot (M_{\kappa_{Na_3Cit}} - M_{\kappa_{NaCl}})$$

$$\bigg((0.167\alpha_{bi}^{-3} + 0.125\alpha_{bi}^{-2} + 0.706\alpha_{bi}^{-1}) \cdot \cdot$$

$$\frac{Q_b \cdot f_{Cit} \cdot c_{pw,artCit} + Q_{inf} \cdot c_{di,Cit}}{Q_b \cdot f_{Cit} + Q_{inf}} -$$

$$c_{di,Na_3Cit}\bigg) + + \frac{Q_{do}}{K_u}(K_{rest3})\bigg)$$

Wherein, $$c_{pw,bi} = \frac{Q_b \cdot f_i \cdot c_{pw,art} + Q_{inf,pre} \cdot c_{inf}}{Q_b \cdot f_i + Q_{inf,pre}}$$

$$c_{pi,bi_{initial\ protein}} = \frac{Q_b \cdot (1 - HCt) \cdot c_{p,a\square_{initial\ protein}}}{Q_b \cdot (1 - Hct) + Q_{inf,pre}}$$

$$\alpha_{bi} = 1.004 \cdot e^{-0.008 \cdot c_{pi,bi_{initial\ protein}}}$$

The used symbols meaning is clarified in the glossary section.

It is noted that if $Q_{inf,pre}=0$, the formula for HDF post-dilution are obtained.

Regarding clearance calculations $Q_{inf}=Q_{inf,pre}+Q_{inf,post}$ should remain to be used as it is the sum of infusions that passes the dialyzer together with the weight loss. The technical solution here described is applicable to HD, HDF, and HF treatment modes, particularly making use of concentrates with acetate and/or citrate. The solution consists of three main parts:

Estimating PC at the beginning of the treatment (i.e., $\kappa_{p,pre}$); in more detail, isoconductivity is estimated at the beginning of treatment. In particular, the estimation is done with an iterative method; after one/two iterations the estimated value is generally considered sufficiently accurate;

Setting the dialysis fluid sodium concentration such that the dialysis fluid tonicity (or sodium or sodium+potassium concentration) is not changed during its passage through the filtration unit; this is achieved by creating a dialysis fluid with a conductivity that is equal to the isoconductivity corrected by an offset;

Maintaining the dialysis fluid composition throughout the whole treatment.

intended to be performed by the control unit 12 of the extracorporeal blood treatment device 1, even if not explicitly stated.

In particular a treatment session is started, preferably, but not necessarily, as a double needle hemodialysis treatment.

The user shall input the treatment mode (e.g. HD, HF, HDF) and the prescription values through the user interface 22. For example the set values for total weight loss WL and total treatment time T are provided, as well as the blood flow rate $Q_b$ and the fresh dialysis flow rate $Q_{di}$. If required also infusion rate, $Q_{inf}$ or total accumulated infusion volume, $V_{inf}$ is provided.

Other parameters may be entered through the user interface, such as bag type, sodium user limits, etc.

The operator has to further input the 'bicarbonate' set before starting the treatment.

The control unit 12 calculates either the initial dialysis liquid conductivity or the initial concentration of at least one solute, e.g. sodium, in the dialysis liquid in order to start with a dialysis fluid conductivity as close as possible to the expected patient pre-dialytic plasma conductivity.

In order to not disturb the tonicity of the patient, it is necessary to set the fluid composition as quickly as possible so that the patient initial plasma conductivity is not inadvertently changed. Thus, estimating of the plasma conductivity has to be done as rapidly as possible when treatment starts; moreover, since the estimation is preferably performed only once, this measure should be as reliable as possible.

In this respect it is worth to note that, in the following detailed description, reference is made to regulating means controlling concentration of an ionic substance, in detail sodium concentration, in the preparation of the dialysis fluid so as to obtain a desired conductivity of the dialysis fluid.

However, regulating means directly regulating the overall dialysis fluid conductivity is also included in the spirit of the present description or, alternatively, regulating means modifying the concentration of a different ionic substance is included in the present description, too.

Given the above, the control unit 12 sets a parameter value for the dialysis fluid in the dialysis fluid supply line 8 at an initial set point; in general the parameter of the dialysis fluid is either the conductivity of the dialysis fluid, or a conductivity-related parameter of the dialysis fluid, or concentration of at least a substance (in particular an ionic substance and in more detail sodium) in the dialysis fluid, or a concentration-related parameter of at least a substance (e.g. sodium) in the dialysis fluid.

In detail, the control unit 12 is configured to set the parameter value for the dialysis fluid at the initial set point so that a dialysis fluid conductivity matches a first estimate of the plasma conductivity of the blood.

In the specific, the control unit 12 calculates the initial set point of the substance concentration and drives the regulating means 10 acting on the sodium concentration in the dialysis liquid.

The set point is calculated before starting the blood circulation (i.e. before starting the treatment).

In order to calculate the dialysis composition initial set point alternative ways might be used, e.g. determine a certain sodium concentration (see below), or using an average plasma conductivity from a large population, or using an average plasma conductivity from a large population corrected for the composition of the dialysis fluid, or calculate based on historic patient data.

In any case, the initial set point for the dialysis liquid is calculated by the control unit 12 so that the expected plasma conductivity is the best guess of plasma conductivity that may be calculated, without prior knowledge of the individual patient.

The selected treatment mode (HD/HF/HDF) also affects the initial estimation of the isoconductivity.

Before explaining in detail the estimation of the initial set point for the dialysis liquid, it is worth to clarify how certain relevant parameters playing a role in the estimation are determined.

Estimation of Dialyzer Clearance

Since the filtration unit (dialyzer) clearance $K_u$ isn't known, it is necessary to estimate it. For the purpose of the estimation, it is assumed that all ions have the same dialyzer clearance, which is equal to the urea clearance.

In HDF treatments it is of fundamental importance to distinguish between the dialyzer clearance, which is related to the transport across the membrane, and the treatment (patient) clearance which describes the removal of a substance from the patient. The patient clearance has clinical interest, whereas for the purpose of calculating the initial set point the interest is in the dialyzer properties. Thus, when clearance is referred to in this document, unless otherwise stated, it is the filtration unit/dialyzer clearance.

In the calculation of clearance, the ultrafiltration flow through the membrane must be taken into account. The total ultrafiltration flow $Q_u$ is the sum of the weight loss flow rate $Q_{wl}$ and the infusion flow $Q_{inf}$:

$$Q_u = Q_{wl} + Q_{inf} \tag{1}$$

In HD treatment mode, the infusion flow $Q_{inf}$ is zero.

In general, the infusion flow $Q_{inf}$ is the sum of the pre-infusion flow rate $Q_{inf,pre}$ (i.e. the fluid infused in the blood circuit 17 upstream the filtration unit 2) and the post-infusion flow rate $Q_{inf,post}$ (i.e. the fluid infused in the blood circuit 17 downstream the filtration unit 2).

The dialyzer inlet fluid flow is:

$$Q_{di} = Q_d - Q_{inf} \tag{2}$$

where $Q_d$ is the total dialysis fluid flow rate, i.e. the total flow rate of dialysis fluid which is prepared by the preparation device 9 and which is then split (if appropriate) into a fluid flow ($Q_{di}$) to the filtration unit and a fluid flow ($Q_{inf}$) to be infused in the blood circuit.

In HF treatment mode, the dialyzer inlet fluid flow $Q_{di}$ is zero, since $Q_d = Q_{inf}$.

The dialyzer outlet fluid flow $Q_{do}$ can be calculated as:

$$Q_{do} = Q_{di} + Q_u \tag{3}$$

The clearance $K_u$ can be calculated with the following equations:

$$K_u = Q_{bwi} \cdot \frac{1 - \frac{Q_{bwo}}{Q_{bwi}} \cdot \psi}{1 - \frac{Q_{bwo}}{Q_{bwi}} \cdot \psi} \tag{4}$$

where $$\psi = \frac{Q_{do}}{Q_{di}} \cdot \left(\frac{Q_{bwo} \cdot Q_{do}}{Q_{bwi} \cdot Q_{di}}\right)^{\frac{k_m A}{Q_u}} \tag{5}$$

$k_m A$ is the modified mass transfer coefficient:

$$k_m A = \frac{Pe}{e^{Pe} - 1} * k_0 A \tag{6}$$

and $k_0 A$ is the mass transfer coefficient of the dialyzer.

$k_0 A$ may be derived having information about the dialyzer used, e.g. the apparatus may receive the data from the user or by reading the specific component identification data. Alternatively the control unit 12 may assume a standard dialyzer with, e.g. a $k_0 A = 1100$ ml/min as a fixed value. In this latter case, the error in calculated K will be within ±10% for all the commonly used dialyzers.

Pe is the so called Peclet number which is defined as $$Pe = \frac{Q_u}{k_0 A} \tag{7}$$

$Q_{bwi}$ is the dialyzer inlet blood water flow, which in HD and HDF post-dilution can be calculated as:

$$Q_{bwi} = f_{bw} Q_b \tag{8}$$

Vice versa, in HDF pre-dilution, the dialyzer inlet blood water flow must include the infusion flow:

$$Q_{bwi} = f_{bw} Q_b 3 Q_{inf} \tag{9}$$

In this equation, $Q_b$ is the real (arterial) blood flow rate and $f_{bw}$ is the dialyzable blood water fraction, which can be calculated with the equation:

$$f_{bw} = f_{cw} \cdot \gamma_{cw,u} \cdot Hct + f_{pw} \cdot (1-Hct) \tag{10}$$

wherein the used symbols meaning is clarified in the glossary section.

With the reference values stated above, the dialyzable blood water fraction $f_{bw}$ for urea will be, e.g. 0.89 at normal conditions for hemodialysis.

The dialyzer outlet blood water flow can be calculated from $$Q_{bwo} = Q_{bwi} - Q_u \tag{11}$$

Estimation of Dialyzer Clearance—HF Treatment

In the HF treatment mode, the clearance calculation is simple, since the clearance is equal to the dialyzer outlet flow:

$$K_u = Q_{do} = Q_u = Q_{inf} + Q_{wl} \tag{12}$$

Since by definition, $Q_{di}=0$ in HF.

Estimation of Citrate Clearance

For citrate, the free ion $Cit^{3-}$ does not dominate over its complexes and ion pairs. There are substantial parts of $CaCit^-$, $MgCit^-$ and $NaCit^{2-}$ together with some $HCit^{2-}$ depending on pH in blood plasma and dialysis solutions.

We approximate that the individual clearance values are close to a single value denoted $K_{b_{Cit}}$.

This clearance is calculated for the actual flow rates using a mass transfer coefficient value of $k_0 A_{Cit} = 0.212 \cdot k_0 A$ into the $K_u$ formulas (4), (5), (6).

Estimation of the Plasma Water Fraction

HD and HDF/HF Post-Dilution

The plasma water fraction depends on the total plasma protein concentration $c_{p,tp}$ and can be estimated as:

$$f_{pw} = 1 - 0.00107 \cdot c_{p,tp} \tag{13}$$

where $c_{p,tp}$ is the plasma protein concentration. With a normal plasma protein concentration $c_{p,tp}=70$ g/L, the plasma water fraction is $f_{pw}=0.925$.

HDF/HF Pre-Dilution

In HDF and HF pre-dilution mode, the dilution of the blood and the corresponding reduction of the total protein concentration must be taken into account to calculate the plasma water fraction for the blood in the dialyzer.

This is done with the following equations:

$$c_{pi,tp} = \frac{Q_b * (1 - Hct) * c_{p,tp}}{Q_b * (1 - Hct) + Q_{inf}} \tag{14}$$

$$f_{pw} = 1 - 0.00107 \cdot 9 c_{pi,tp} \tag{15}$$

the used symbols meaning is clarified in the glossary section.

Estimation of the Donnan Factor $\alpha$

HD and HDF/HF Post-Dilution

The transport of charged permeable substances over the dialyzer membrane is affected by the charged plasma proteins. The effect is quantified by a Donnan factor $\alpha$.

If the plasma protein concentration c p,tp is known, the Donnan factor $\alpha$ for a single charged cation can be estimated with the equation:

$$\alpha = 1.004 \cdot e^{-0.0008 * c_{p,tp}} \tag{16}$$

With a normal plasma total protein concentration $c_{p,tp}=70$ g/L, the Donnan factor is $\alpha=0.95$ at conditions typical for hemodialysis.

HDF/HF Pre-Dilution

In HDF and HF pre-dilution mode, the dilution of the blood and the corresponding reduction of the total protein concentration must be taken into account when calculating the Donnan factor for the blood in the dialyzer.

This is done with the following equations:

$$c_{pi,tp} = \frac{Q_b * (1 - Hct) * c_{p,tp}}{Q_b * (1 - Hct) + Q_{inf}} \tag{17}$$

$$\alpha_{bi} = 1.004 * e^{-0.0008 * c_{pi,tp}} \tag{18}$$

wherein the used symbols meaning is clarified in the glossary section.

Estimation of Dialysis Fluid Starting Composition

In general terms, the control unit 12 is configured to calculate the initial set point of the substance concentration to be set (e.g. sodium) in the dialysis fluid as a function of the treatment mode. In other terms, depending on whether HD, HF or HDF is selected, the control unit 12 determines the initial set point based on different mathematical relationships which will be here below explained and detailed.

Moreover, the control unit 12 is configured to calculate the initial set point as a function of the difference in concentration of at least one (and in detail several) further substance in the dialysis fluid and the same further substance in the plasma. It is noted that in case of HDF pre-dilution and HF pre-dilution treatment modes, the concentration of the substance in the plasma is adjusted to take into consideration its dilution due to infusion.

The calculation is based on average pre-dialysis concentrations of at least one (and preferably all) substance chosen between sodium, potassium, acetate, citrate, and bicarbonate (as well as other solutes) in a large patient population, plus the contribution related to dialysis fluid of bicarbonate, potassium, acetate, and citrate resulting from the prescription and from the chosen concentrate combination.

The control unit 12 calculates the initial set point also as a function of the concentration of at least one, in particular two, and precisely all the substances in the dialysis fluid included in the group comprising bicarbonate, potassium, acetate, and citrate.

Furthermore, the control unit 12 calculates the initial set point of the substance (i.e. sodium) in the dialysis fluid also as a function of the difference in concentration of one or more further substances in the dialysis fluid different from sodium; in particular these substances include bicarbonate, potassium, acetate, and citrate and two, and precisely all, the differences, in particular weighted differences, in concentration value of the mentioned substances in the dialysis fluid and in the plasma are taken into account.

The control unit 12 calculates the initial set point of the substance in the dialysis fluid also as a function of the molar conductivities of one or more substances, such as one, two, three, or all of the following substances in the dialysis fluid which are sodium bicarbonate ($NaHCO_3$), sodium chloride (NaCl), sodium acetate (NaCH$_3$COO), trisodium citrate (Na$_3$C$_6$H$_5$O$_7$), potassium chloride (KCl), and sodium lactate (Na$_3$C$_3$H$_5$O$_3$).

The control unit 12 calculates the initial set point of the substance in the dialysis fluid as a function of an estimated plasma water concentration of at least sodium, and/or bicarbonate, and/or potassium and/or acetate and/or citrate. The estimated plasma water concentration of sodium, bicarbonate, potassium, acetate, and citrate, is, for example, the mean pre-dialysis values of the corresponding substance for large patient populations, or historical document for a particular patient.

In case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion.

In this case, the dilution of the plasma water concentration is a function of blood flow rate and infusion flow rate. Additionally, the dilution of the plasma water concentration is a function of the infusion fluid concentration of the specific substance (i).

The initial set point may also be a function of one or more flow rates, in particular of the dialysate flow rate at the outlet of the secondary chamber 4.

Also an efficiency parameter of the filtration unit 2 plays a role in the initial set point calculation of sodium. In particular a clearance $K_u$ of the filtration unit 2 may be used (e.g. the urea clearance).

Dialysis Fluid Starting Composition—HD Mode

Specifically in HD mode, the control unit 12 is configured to calculate the initial set point of sodium concentration to be set in the dialysis fluid before the start of the treatment using the following relationship:

$$c_{di,Na,start} = \alpha * c_{pw,Na} + \qquad (19)$$
$$\frac{1}{M_{K_{NaCl}}}(M_{K_{NaHCO_3}} - M_{K_{NaCl}})\left(\frac{1}{\alpha} * c_{pw,HCO_3} - c_{di,HCO_3}\right) + +$$
$$\frac{1}{M_{K_{NaCl}}}(M_{K_{NaAc}} - M_{K_{NaCl}})\left(\frac{1}{\alpha} * c_{pw,Ac} - c_{di,Ac}\right) +$$
$$\frac{M_{K_{Cl}}}{M_{K_{NaCl}}}(\alpha * c_{pw,K} - c_{di,K}) + + \frac{1}{M_{K_{NaCl}}} \frac{Q_{do}}{K_u} K_{rest3}$$

wherein the used symbols meaning is clarified in the glossary section.

In HD mode case, in case also citrate has to be taken into consideration, the control unit 12 may alternatively use the following relationship:

$$c_{di,Na,start} = \alpha * c_{pw,Na} + \qquad (20)$$
$$\frac{1}{M_{K_{NaCl}}}(M_{K_{NaHCO_3}} - M_{K_{NaCl}})\left(\frac{1}{\alpha} * c_{pw,HCO_3} - c_{di,HCO_3}\right) + +$$
$$\frac{1}{M_{K_{NaCl}}}(M_{K_{NaAc}} - M_{K_{NaCl}})\left(\frac{1}{\alpha} * c_{pw,Ac} - c_{di,Ac}\right) +$$
$$\frac{M_{K_{Cl}}}{M_{K_{NaCl}}}(\alpha * c_{pw,K} - c_{di,K}) + + \frac{K_{bCit}}{K_u}(M_{Na_3Cit} - 3M_{K_{NaCl}})$$

-continued
$$((0.167\alpha^{-3} + 0.125\alpha^{-2} + 0.706\alpha^{-1}) * c_{pw,Na_3Cit} - c_{di,Na_3Cit}) + +$$
$$\frac{1}{M_{K_{NaCl}}} \frac{Q_{do}}{K_u} K_{rest3}$$

wherein the used symbols meaning is clarified in the glossary section.

For $K_u$ calculations, see previous section.

Dialysis Fluid Starting Composition—HDF Post-Dilution Mode

In case of HDF post-dilution mode is selected, the same equations (19) and (20) apply. Differently from HD mode, dialyzer clearance $K_u$ is calculated for the HDF post-dilution mode with the substitution flow rate $Q_{inf}$ taken into account (see equations (4-8)).

Dialysis Fluid Starting Composition—HDF Pre-Dilution Mode

In case of HDF pre-dilution mode is selected, the dilution of the blood before it enters the dialyzer must be taken into account.

The equations for HDF pre-dilution are somehow similar to HDF post-dilution.

The dilution of the plasma water concentration of substance i in pre-dilution mode is described by the following equation:

$$c_{pw,bi} = \frac{Q_b * f_i * c_{pw,art} + Q_{inf} * c_{inf}}{Q_b * f_i + Q_{inf}} \qquad (21)$$

wherein the used symbols meaning is clarified in the glossary section.

Thus, the plasma water concentrations for all substances is replaced with the corresponding diluted blood concentration as defined by the equation (21) above.

Also the "normal" Donnan factor $\alpha$ is replaced with Donnan factor $\alpha_{bi}$ calculated for the diluted protein concentration, as described in equations (17) and (18).

The dialyzable blood water fraction $f_i$ can be calculated with the equation:

$$f_i = f_{cw} \cdot \gamma_{cw,i} \cdot Hct + f_{pw} \cdot (1-Hct) \qquad (22)$$

wherein the used symbols meaning is clarified in the glossary section.

Of course, in HDF pre-dilution, the calculated isotonic or isonatric or isonatrikalemic sodium set point needs to be adjusted if the substitution fluid flow or blood flow is changed during treatment, since this changes the dilution of the blood compared to the conditions during the identification phase.

Specifically in HDF pre-dilution mode, the control unit 12 is configured to calculate the initial set point of sodium concentration to be set in the dialysis fluid before the start of the treatment using the following relationship:

$$c_{di,Na,start} = \qquad (23)$$
$$\alpha_{bi} \cdot \frac{Q_b \cdot f_{Na} \cdot c_{pw,artNa}}{Q_b \cdot f_{Na} + (1-\alpha_{bi}) \cdot Q_{inf}} + + \frac{1}{M_{K_{NaCl}}}\Big((M_{K_{NaHCO_3}} - M_{K_{NaCl}})$$
$$\Big(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} -$$
$$c_{di,HCO_3}\Big) + + (M_{K_{NaAc}} - M_{K_{NaCl}})$$

-continued $$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right)++$$

$$M_{\kappa_{KCl}} \cdot \left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right)++$$

$$\frac{K_{b,Cit}}{K_u} \cdot (M_{\kappa_{Na_3Cit}} - 3M_{\kappa_{NaCl}})$$

$$\left((0.167\alpha_{bi}^{-3} + 0.125\alpha_{bi}^{-2} + 0.706\alpha_{bi}^{-1}) \cdot \cdot \right.$$

$$\left. \frac{Q_b \cdot f_{Cit} \cdot c_{pw,artCit} + Q_{inf} \cdot c_{di,Cit}}{Q_b \cdot f_{Cit} + Q_{inf}} - c_{di,Na_3Cit}\right)++$$

$$\frac{Q_{do}}{K_u} \kappa_{rest3}\right) \cdot \frac{Q_b \cdot f_{Na} + Q_{inf}}{Q_b \cdot f_{Na} + (1-\alpha_{bi}) \cdot Q_{inf}}$$

Dialysis Fluid Starting Composition—HF Post-Dilution Mode

The equations for HF post-dilution mode are the same as for to HD, but the dialyzer clearance is substituted by the dialysate flow rate at filtration unit outlet, i.e. $K_u = Q_{do}$.

Dialysis Fluid Starting Composition—HF Pre-Dilution Mode

In case of HF pre-dilution mode is selected, the dilution of the blood before it enters the dialyzer must be taken into account.

The equations for HF pre-dilution are the same as for to HDF post-dilution, but the dialyzer clearance is substituted by the dialysate flow rate at filtration unit outlet, i.e. $K_u = Q_{do}$.

Of course, for each and every treatment mode, different mathematical relationships may be used taking into account exclusively some of the considered substances and/or exclusively some of the conductivities and/or molar differences.

Estimation of Isoconductivity

Once the sodium initial set point has been calculated (based on the selected HD/HDF/HF treatment mode and the above mathematical relationships) and a corresponding dialysis fluid has been prepared by the control unit 12 driving the regulating means 10, the treatment may start.

The dialysis fluid is prepared and then circulated through the dialysis fluid circuit 32. Depending on the selected treatment mode, the dialysis fluid is directed:
- to the secondary chamber 4 of the filtration unit 2 only so as to exchange with blood (HD mode);
- to the secondary chamber 4 of the filtration unit 2 so as to exchange with blood and infused into the blood circuit 17 (HDF mode);
- to the blood circuit only (HF mode); in this case an ultrafiltration flow rate is set to achieve a $Q_U = Q_{do}$.

Correspondingly, blood is withdrawn from the patient and circulated in the extracorporeal blood circuit 17 and particularly is circulated through the primary chamber 3 of the filtration unit 2.

At least one, and in general a plurality, of consecutive initial values of the parameter (in the specific example, the conductivity) of the dialysate downstream of the secondary chamber 4 are measured at the beginning of the treatment through sensor 11.

The post-dialyzer conductivity will change initially, due to e.g. dynamics when treatment is started (e.g. leaving bypass conditions) or when blood flow is ramped up. However, it is expected to stabilize within few (e.g. 4) minutes. The measurement is made as soon as certain stability criteria are fulfilled.

The set point calculated by the machine according to the previously disclosed equations includes the effect of glucose (if present in the concentrate) and thus the conductivity $\kappa_{di,start,set}$ has to be compensated for this accordingly to create the pure ion solution conductivity $\kappa_{0,di,start,set}$ which is to be used for the calculation.

The control unit 12 is configured to validate and further process the measurement of an initial value of the conductivity of the dialysate as soon as the diffusion process in the filtration unit 2 reaches stable conditions.

As mentioned, a transient exists when dialysis fluid and blood start exchanging during which the dialyzer outlet conductivity is not stable; during the transient period the measured outlet conductivity values should be disregarded.

Stable conditions for the diffusion process may be determined in case one or more of the following conditions occurs:
- a first derivative of the median or of the average value of the conductivity of the dialysate is lower in size than a first threshold;
- a first derivative of the value of conductivity of the dialysate is lower in size than a first threshold for a specified time window;
- a first derivative of the filtered value of conductivity of the dialysate is lower in size than a first threshold for a specified time window, the filtered value being a value filtered either by a median filter (which picks out the median) or a linear filter, either a finite impulse response filter (which is equal to a weighted average), or an infinite impulse response filter (which is standard, but has the form yf(t)=−a1*yf(t−1)− . . . −an*yf(t−n)+b1*y(t−k−1)+ . . . +bm*y(t−k−m), where yf(t) is the filtered value at time t, y(t) is the measured value at time t, n and m are the number of parameters a and b (the order) of the filter and k is the number of pure time delays);
- a second derivative of the median value of the conductivity of the dialysate is lower in size than a second threshold;
- a second derivative of the filtered value of conductivity of the dialysate is lower in size than a first threshold for a specified time window;
- a change or a relative change of the value itself or a filtered version of the value of the conductivity since a fixed previous point in time is below a first threshold (an expanding window);
- a change or the relative change of the value itself or a filtered version of the value of the conductivity since a fixed time interval backwards is below a first threshold (a sliding window, constant in length);
- a prefixed time has lapsed after starting circulation of both blood and fresh dialysis fluid in the filtration unit, in particular said pre-fixed time being not more than 15 minutes;
- a variable time has lapsed after starting circulation of both blood and dialysis fluid in the filtration unit, said variable time being function of at least one parameter, such as the volume of the secondary chamber 4 of the filtration unit 2; in particular the variable time may be a function of further parameters such as dialysis fluid flow rate, blood flow rate, filtration unit permeability, etc. . . . .

The stability condition is preferably determined by observing, on a 1-minute window, the first derivative of $\kappa_{do}$ and checking when it is lower in size than a fixed threshold. Once this stability criterion is fulfilled, $\kappa_{do}$ is taken as the median value on the 1-minute window. The first derivative is used to avoid the presence of possible drifts in the outlet conductivity. Extracting the median and/or the average value of $\kappa_{do}$ allows discharging possible outliers of the outlet conductivity signal from the average calculation.

In order to minimize the time needed to reach stability conditions, changes in dialysis fluid flow rate and in bicarbonate prescription may be prevented during this preliminary isotonic sodium identification phase.

Changes in blood flow, ultrafiltration flow rate or bypass are vice versa generally allowed, but they will delay stability. Moreover, it is not possible to change the concentrate combination type after the treatment is started.

Alternatively, it might be possible to just estimate the initial value of the conductivity of the dialysate fluid representative of the conditions prevailing after the diffusion process has reached stable conditions; the estimate is based on one or more conductivity measurements in the dialysate before reaching the stable conditions and using proper estimate algorithms.

Glucose and urea, the main electrically neutral substances in dialysis fluid, reduce the conductivity of the dialysis fluid. The effect is small but noticeable and leads to a plasma conductivity underestimation and thus to an underestimation of the plasma sodium. Hence, a compensation for urea and glucose contribution may also be applied to the measured conductivities $\kappa_{do}$ and $\kappa_{do}$: the resulting conductivities for pure ion solutions ($\kappa_{0,di}$ and $\kappa_{0,do}$) may alternatively be used in all the calculations using conductivities reported below.

The control unit 12 may compensate the measured initial conductivity value of the dialysate as a function of the concentration of at least glucose.

Moreover, the control unit may compensate the measured initial conductivity value of the dialysate as a function of a flow rate, such as the dialysate flow rate at the outlet.

The control unit 12 may compensate the measured initial conductivity value of the dialysate as a function of an efficiency parameter of the filtration unit 2, (e.g. a clearance of the filtration unit 2, in detail the urea clearance).

Furthermore, the control unit 12 may compensate the measured initial conductivity value of the dialysate as a function of an estimated plasma concentration of glucose and/or urea.

The specific formula to compensate the measured initial conductivity value of the dialysate is the following:

$$\kappa_{0,do} = \frac{\kappa_{do}}{\left(1 - \gamma_g\left(c_{di,g} + \frac{f_g \kappa_B K_u}{Q_{do}}\left(\frac{c_{p,g}}{f_{pw}} - c_{di,g}\right)\right)\right)\left(1 - \gamma_u \frac{K_u}{Q_{do}} \frac{c_{p,u}}{f_{pw}}\right)} \quad (24)$$

The significance of the denotations and constants above is given in the Glossary.

The estimated values of dialyzer clearance $K_u$ and plasma water fraction $f_{pw}$ depend on the selected treatment mode (HD/HDF/HF) and should be calculated as described in the previous sections (see eq. (13) and (15)).

Moreover, in HDF and HF pre-dilution mode, the plasma concentrations of glucose and urea $c_{p,g}$ and $c_{p,g}$ must be replaced with the corresponding diluted concentrations (see eq. (17)).

The control unit 12 may be configured to compensate the initial conductivity of the dialysis fluid as a function of the concentration of glucose, if glucose is present in the dialysis liquid.

The control unit 12 is specifically configured to compensate the initial conductivity of the fresh dialysis fluid using the following formula:

$$\kappa_{0,di} = \frac{\kappa_{di}}{1 - \gamma_g c_{di,g}} \quad (25)$$

The significance of the denotations and constants above is given in the Glossary.

It is worth to note that the initial conductivity of the fresh dialysis fluid upstream the secondary chamber 4 may be either measured or taken as the set value for dialysis conductivity.

In general, it is preferred to measure the initial conductivity of the dialysis fluid through the sensor 35, too.

It is important to underline that the initial setting of the sodium concentration calculated or determined as above stated to be as close as possible to the expected plasma conductivity (eq. 1) may be optional, meaning that the method for estimating the initial plasma conductivity may be performed even if the sodium content of the dialysis conductivity is initially simply set by the operator.

Also correction based on main electrically neutral substances is optional and may be used or not to increase accuracy.

The compensation for the main electrically neutral substances (e.g. urea and glucose) may be alternatively applied to the final adjustment contribution terms.

Vice versa, it is relevant to measure at least the conductivity downstream the filtration unit (and preferably also the conductivity upstream the filtration unit) as soon as possible, i.e. as soon as stable conditions are reached or as soon as an estimate of such conductivity in stable conditions may be performed.

This is due to the need of matching as much as possible the patient initial plasma conductivity which is clearly affected/changed by the different conductivity of the dialysis fluid circulating during the treatment.

In order to make a first estimate of the plasma conductivity based on measured values, two embodiments are provided, which may be used together or alternatively.

Firstly, the control unit 12 calculates the value of the initial plasma conductivity, based on the measured initial parameter value of the dialysate (i.e. based on conductivity or concentration measurement of dialysate on the filtration unit outlet) and on the corresponding parameter value of the dialysis fluid in the dialysis fluid supply line 8 e.g. conductivity or concentration). During the start of the treatment and particularly during circulating the dialysis fluid through the secondary chamber 4 and/or in the infusion line 39 up to measuring the initial value of the parameter of the dialysate downstream of the secondary chamber used for the calculating of the initial plasma conductivity, the dialysis fluid conductivity (or concentration) is kept substantially constant.

In other words, the calculation of the initial plasma conductivity is performed with no conductivity step as it was normally made in the prior art devices.

Indeed, both the two embodiments allowing plasma conductivity estimation do not require to change the dialysis conductivity or the sodium content in the dialysis liquid and to take measures at the inlet and at the outlet of the dialyzer in both conditions.

In this respect the term 'substantially constant' means that the conductivity of the dialysis fluid is not changed by the machine or by the operator, but it may not be exactly constant due to small oscillations on the measured value caused by noise, tolerances in the concentrate dosing system or tolerances in the conductivity measurements. Generally these small variations around the set value are less than 0.2 mS/cm.

Just a single reliable measurement at the inlet and at the outlet of the dialyzer may be sufficient to have a preliminary (to be made more accurate) or an already final estimation of the PC.

From a general point of view, the control unit 12 is further configured to calculate the plasma conductivity as a function of at least one or more flow rates.

The flow rates include the dialysate flow rate at the outlet of the secondary chamber 4; in addition, the flow rates may include the blood flow rate in the blood lines too.

Also an efficiency parameter of the filtration unit 2, in particular a clearance of the filtration unit 2 (e.g. the urea clearance) is used for plasma conductivity. Of course, a nominal clearance and/or a calculated clearance may be used; the calculated clearance may be both an estimated clearance as well as a compensated clearance.

Moreover, the plasma conductivity depends on an (possibly compensated) initial conductivity of the dialysate and on a (possibly compensated) conductivity of the dialysis fluid in the dialysis supply line 8.

According to a first embodiment, the control unit 12 is programmed to calculate the initial plasma conductivity based on the sum of at least the initial conductivity of the dialysate plus a difference between inlet and outlet conductivity at the filtration unit, or dialyzer, weighted by a factor of the dialysate flow rate. In more detail the difference between inlet and outlet conductivity at the dialyzer is weighted by a factor of the blood flow rate in the blood lines too.

Specifically, according to the first embodiment, the control unit 12 is configured to calculate the plasma conductivity using the following formula:

$$\kappa'_{p,1} = \kappa_{0,do} + \frac{Q_{do}}{Q_{Bset}}(\kappa_{0,do} - \kappa_{0,di}) \quad (26)$$

The significance of the denotations above is given in the Glossary.

It is worth to underline that during the above described calculation of the initial plasma conductivity (formula (26)), the dialysis fluid circulates through the secondary chamber 4 and/or is infused into the blood circuit 17 (depending on selected HD/HF/HDF mode) maintaining the dialysis fluid parameter value substantially constant.

In the second embodiment, the control unit 12 is programmed to calculate the initial plasma conductivity based on the sum of at least the initial conductivity of the fresh dialysis fluid plus a difference between inlet and outlet conductivity at the dialyzer weighted by a factor of the dialysate flow rate. In more detail the difference between inlet and outlet conductivity at the filtration unit, or dialyzer, is weighted by a factor of the dialyzer clearance too.

Specifically, according to the second embodiment, the control unit 12 is configured to calculate the plasma conductivity using the following formula:

$$\kappa''_{p,1} = \kappa_{0,di} + \frac{Q_{do}}{K_u}(\kappa_{0,do} - \kappa_{0,di}) \quad (27)$$

The significance of the denotations and constants above is given in the Glossary.

It is worth to underline that during the above described calculation of the initial plasma conductivity (formula (27)), the dialysis fluid circulates through the secondary chamber 4 and/or is infused into the blood circuit 17 (depending on selected HD/HF/HDF mode) maintaining the dialysis fluid parameter value substantially constant.

In more detail, in the formulas above:
- $k_{0,di}$ is the set/measured-by-sensor 35 value for conductivity of the dialysis fluid, corrected for glucose (see previous equation);
- $k_{0,do}$ is the mean value of outlet conductivity on the stability 1-minute window, corrected for glucose and urea;
- $Q_{bset}$ and $Q_{do}$ are the mean values, respectively, of blood flow rate set and of dialysate flow rate at the filtration unit, or dialyzer, outlet, on the stability window;
- $K_u$ is the dialyzer diffusive clearance for urea (to be determined according to the treatment mode and respective equation—previously described)

According to first estimate, $k_{p,1}$ may be found after approx. 6 to 10 minutes after treatment start.

Of course, both formulas (26) and (27) for estimation of plasma conductivity may be iteratively applied, meaning that the newly calculated estimate of PC ($k_{p,1}$) is imposed to the dialysis fluid and a new estimate ($k_{p,2}$) again calculated after taking measures of the conductivity at the inlet and outlet of the filter as soon as stable conditions are reached.

Of course, in case of iteration of anyone of the above calculations according to formulas (26) or (27), after the first plasma conductivity estimation, the dialysis fluid parameter value is changed since the newly calculated estimate of PC ($k_{p,1}$) is imposed to the dialysis fluid, meaning that the conductivity of the dialysis fluid is changed. This however does not impact on the fact that the first calculation according to formulas (26) and (27) is made without a change in the conductivity of the dialysis fluid.

In one way of exploiting the method, the first formula (26) or the second formula (27) is applied only once and the estimated PC ($k_{p,1}$) is considered already a good estimation of initial plasma conductivity.

In another way, the first formula (26) is applied twice.

In a further way, the second formula (27) is applied twice; in this case, the dialysis fluid sodium concentration correspondent to $k_{p,1}$ is iteratively calculated and applied. k do is measured again as soon as stable conditions are reached: the stability criteria are the same as previously described. A second estimation of PC ($k_{p,2}$) according to formula (27) is done and $k_{p,2}$ is used as $k_{p,pre}$.

In this second case $k_{p,2}$ should be found after approx. 11-17 minutes after treatment start.

The above mentioned steps according to one of the described embodiment are schematically shown in FIG. 3.

It is relevant to note that in equations (26) and (27), k do and k d, may be used instead of $k_{0,do}$ and $k_{0,di}$.

A timeout may be provided for each of $k_{p,1}$ and $k_{p,2}$ estimation phases (due to e.g. a change in some parameters). At the end of either one of these timeouts (e.g., if the stability has not been reached), an alarm shall be triggered to de-activate the isotonic treatment procedure. In general it does not make sense to apply isotonic dialysis too late into the treatment.

The dialysis fluid sodium concentration correspondent to $k_{p,pre}$ is then determined.

The resulting dialysis fluid sodium concentration applied, $C_{di,Na, kp,pre}$, would correspond to implement an isoconductive dialysis.

In summary, the proposed method of estimating isoconductivity at the beginning of treatment is done through the following main steps:

7. Set the dialysis fluid conductivity $k_{di,start}$ to be as close to the isoconductivity as possible before treatment start. This is done by calculating a start sodium concentration based on average data from a large patient population;
8. Measure dialysis fluid conductivity upstream and downstream the dialyzer ($k_{Odi}$ and $k_{Odo}$) as soon as stable conditions have been reached after treatment start;
9. Make a first estimate of the isoconductivity $k_{p,1}''$ from the measured difference between $k_{Odi}$ and $k_{Odo}$;
10. Set $k_{Odi}$ equal to $k_{p,1}''$;
11. Measure dialysis fluid conductivity upstream and downstream the dialyzer ($k_{Odi}$ and $k_{Odo}$) again, calculate a second estimate $k_{p,2}''$.
12. Use $k_{p,2}''$ second estimate as an estimate of $k_{p,pre}$.

Setting of the Dialysis Fluid Sodium Concentration

The starting point for setting the individualized sodium concentration is isoconductive dialysis, i.e., when pre and post dialyzer conductivities are equal. This is achieved when the dialysis fluid conductivity has been set to the estimated pre-dialysis isoconductivity.

The dialysis fluid sodium concentration shall then be set to provide either isotonic, isonatric or isonatrikalemic treatment based on determined dialysis fluid conductivity for isoconductive dialysis.

The setting can be done either as an adjustment in conductivity set point or as an adjustment in sodium set point, but a sodium set point change is chosen as main implementation.

Since an isotonic or isonatric or isonatrikalemic dialysis is to be applied, this sodium value may be adjusted with a proper adjustment factor (depending on the selected treatment mode—HF/HDF/HD—and depending on the choice to apply isotonic, isonatric or isonatrikalemic dialysis).

In respect to the above mentioned treatments, it is relevant to note the following.

An isonatric dialysis may in general terms be considered as a treatment where the sodium concentration in the extracellular fluid of the patient is maintained stable or undergoes reduced variations throughout treatment.

It is however worth noting that tonicity is determined by the particles that are osmotically active.

Actually, the dialysis fluid (and the plasma) contains a multitude of substances that influence tonicity/osmolality, not just sodium, even if this is the main determinant of serum osmolality.

Hence, an isotonic dialysis may be considered as a dialysis where the tonicity of the fluids in the patient is maintained stable or undergoes reduced variations throughout dialysis treatment. This would be achieved by maintaining the tonicity of the dialysis fluid substantially equal to the tonicity of the extracellular fluid throughout treatment. In this case, the tonicity of the dialysis fluid does not change pre- to post-filtration unit 2.

An isonatrikalemic dialysis, may in general terms be considered as a treatment where the sum of sodium and potassium concentrations in the patient extracellular fluid is maintained stable or undergoes reduced variations throughout dialysis treatment (in this case, the sum of sodium and potassium concentrations of the dialysis fluid does not change pre- to post-filtration unit 2). Considering that a patient shall lose a certain amount of potassium during treatment, the isonatrikalemic condition may be maintained with a proportional increase in serum sodium concentration.

An isoconductive dialysis may in general terms be considered as a dialysis treatment maintaining the conductivity of the dialysis fluid equal to the conductivity of the extracellular fluid, which in this case is represented by the plasma conductivity.

The plasma conductivity (PC, $\kappa_p$) is the conductivity at which the dialysis fluid conductivity is not changed during its passage through the dialyzer. Then the conductivities upstream and downstream the filtration unit 2 are equal: $\kappa_{di}=\kappa_{do}$.

In case of an isotonic or isonatric or isonatrikalemic treatment is to be performed, the mentioned adjustment factor is calculated based on molar conductivities, dialysis fluid composition, and the best estimate of plasma water composition as will better emerge from the following description. The best estimate of plasma water composition may be derived from literature, or may be based on statistical prepared values, or test of patient, or obtained with direct lab measurements made before the treatment.

According to an innovative aspect, the control unit 12 receives a value representative of a parameter of the blood in said blood lines 6, 7. The blood parameter may be the plasma conductivity or a plasma conductivity-related parameter.

In particular, the control unit 12 may be programmed for calculating the plasma conductivity, for example executing the method previously disclosed or, alternatively using known methods such as those described in EP 2377563.

Alternatively, the control unit 12 directly receives as an input the plasma conductivity. For example, the physician or the nurse may receive a lab analysis and may provide the datum to the machine through the user interface of the dialysis monitor; the control unit 12 is programmed for storing in a memory the plasma conductivity to be used for the following dialysis fluid parameter regulation.

Finally, the plasma conductivity may be directly measured in vivo by the monitor before starting the treatment session using a proper plasma conductivity sensor.

The control unit 12 is generally configured for setting a parameter value for the dialysis fluid in the dialysis supply line 8 at a set point.

The parameter of the dialysis fluid is chosen between a conductivity of the dialysis fluid, a conductivity-related parameter of the dialysis fluid, a concentration of a substance in the dialysis fluid and a concentration-related parameter of a substance in the dialysis fluid.

Depending on the specific dialysis monitor, the sodium content (or the content of more than one electrolyte) may be regulated in the dialysis line. Alternatively, the control parameter may be the overall conductivity of the dialysis fluid.

The setting of the parameter value in the dialysis fluid (which is hereinafter identified as sodium concentration set point in the dialysis fluid with no limiting effect) includes the sub-step of calculating the sodium concentration set point (at least) as a function of a main contribution term based on/function of the plasma conductivity and as a function of an adjustment contribution term, i.e. a term which takes into account the transport driving gradient of certain specific substances. Additionally, compensation for unwanted sodium transfer may be applied as explained in detail in the last paragraphs of the present description.

The main contribution term may affect (may contribute to) the dialysis fluid sodium concentration set point for at least 80% of the same parameter value (and in particular for at least 90% of the parameter value), i.e. the general value of the sodium concentration mainly depend on plasma conductivity.

In more detail, the adjustment contribution term may contribute to the dialysis fluid sodium concentration set point for less than 15% of the same parameter value (and in particular for less than 10% of the parameter value).

The calculation is an algebraic sum of at least the main contribution term ($C_{di,Na,\kappa_{p,pre}}$) and the adjustment contribution term ($c_{di,Na,adj}$) according to the following general formula:

$$c_{di,Na,set} = c_{di,Na,\kappa_{p,pre}} + c_{di,Na,adj} \tag{28}$$

In order to obtain a dialysis fluid sodium implementing a certain kind of dialysis, i.e. $C_{di,Na,set}$, a adjustment factor $C_{di,Na,adj}$ needs to be applied to make the dialysis fluid matching a certain specific concentration of the plasma.

($C_{di,Na,\kappa_{p,pre}}$) is the dialysis fluid concentration of sodium at isoconductive state, i.e. when the dialysis fluid conductivity $\kappa_{di}$ matches the estimated pre-dialysis plasma conductivity $\kappa_{p,pre}$.

Though not essential since a calculation may be made based on conductivities too, the main contribution term and the adjustment contribution term are dimensionally concentrations of a substance (e.g. sodium) in a fluid.

The adjustment contribution term is the sodium concentration set point adjustment relative to an isoconductive state to provide a specific treatment which may be, for example, chosen in the group including isotonic dialysis, isonatric dialysis, and isonatrikalemic dialysis.

The Applicant has understood that certain specific substances, namely bicarbonate, potassium, acetate, and citrate have a major effect which should be taken into account when it is desired to run an isotonic, or isonatric, or isonatrikalemic dialysis treatment. Indeed, an isoconductive dialysis (i.e. a dialysis maintaining the conductivity of the dialysis fluid equal to the conductivity of the extracellular fluid, which in this case is represented by the plasma conductivity—as defined, plasma conductivity (PC, $\kappa_p$) as the conductivity at which the dialysis fluid conductivity is not changed during its passage through the dialyzer so that the pre-dialyzer and the post-dialyzer conductivities are equal: $\kappa_{1i} = \kappa_{do}$) causes an overload of sodium in the patient.

To avoid overloading at least the effect of the above substances must be taken into duly consideration. Of course other substances play a role, such as lactate, magnesium, and calcium.

Furthermore, the difference in concentration between same substances in the blood and in the dialysis fluid influences, as well, the sodium overload in case of isoconductive treatments.

Given the above, the Applicant also realized that in calculating the adjustment contribution term, certain parameters having a weight in determining the overload of sodium are known and depends on the machine dressing (e.g. used concentrates) or on the prescription for the patient (e.g. dialysate flow rate). Other parameters depend on the patient undergoing the treatment and therefore may be either directly measured (e.g. lab analysis) or estimated (e.g. based on large population numbers or patient history).

Since isoconductive dialysis causes sodium overload, the adjustment contribution term generally assumes a negative value, i.e. reduces the set point concentration of sodium in the dialysis fluid calculated for isoconductive treatment.

In more detail, the control unit is configured to calculate the adjustment contribution term based on a concentration of at least a substance in the dialysis fluid chosen in the group including bicarbonate, potassium, acetate, lactate, and citrate; in particular calculation is made as a function of the concentration of at least two of said substances, and in further detail as a function of the concentration of bicarbonate, potassium, acetate, and/or citrate, and lactate in the dialysis fluid.

As mentioned, the control unit is configured to calculate the adjustment contribution term as a function of the difference, in particular weighted difference, in concentration of at least one of the above cited substances in the dialysis fluid and the same substances in the blood plasma.

In case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion.

Additionally, the control unit calculates the adjustment contribution term as a function of the molar conductivities of at least a substance in the dialysis fluid; in detail the substance may be chosen from the group including acids or salts of bicarbonate, chloride, acetate, phosphate, and sulphate, wherein the salt is formed with sodium, potassium, calcium, or magnesium.

In more detail, the calculations take into account the molar conductivities of at least two of said substances, specifically of at least three and particularly of sodium bicarbonate ($NaHCO_3$), sodium chloride ($NaCl$), sodium acetate ($NaCH_3COO$), trisodium citrate ($Na_3C_6H_5O_7$), and potassium chloride ($KCl$).

Again, the adjustment contribution term is a function of the differences between two molar conductivities, a first molar conductivity of a substance chosen in the group including sodium bicarbonate ($NaHCO_3$), sodium acetate ($NaCH_3COO$), trisodium citrate ($Na_3C_6H_5O_7$), and potassium chloride ($KCl$), and a molar conductivity of sodium chloride ($NaCl$).

Alternatively, the adjustment contribution term is a function of the differences between two molar conductivities, a first molar conductivity of a substance chosen in the group including sodium bicarbonate ($NaHCO_3$), trisodium citrate ($Na_3C_6H_5O_7$), and potassium chloride ($KCl$), and a molar conductivity of sodium chloride ($NaCl$).

The control unit is also configured to calculate the adjustment contribution term as a function of an estimated plasma water concentration of at least a substance in blood entering the dialyzer; the substance is chosen in the group including bicarbonate, potassium, acetate, lactate, and citrate; in particular the calculation is made based on the estimated plasma water concentration of at least two, three or four of said substances; in the specific example of the present description the adjustment contribution term is a function of the estimated plasma water concentration of bicarbonate, potassium, and acetate or is a function of the estimated plasma water concentration of bicarbonate, potassium, citrate, and acetate.

In HD, HDF post-dilution and HF post-dilution, the estimated plasma water concentration of bicarbonate, potassium, citrate, and acetate is the mean pre-dialysis values of the corresponding substance for large patient populations. As previously mentioned, the estimated plasma water concentration of bicarbonate, potassium, and acetate may alternatively be based on other statistical prepared values, or historical values for the specific patient, or direct measurements made before the treatment.

In respect to HDF pre-dilution and HF pre-dilution, the estimated plasma water concentration in blood entering the dialyzer takes into account the dilution of the blood due to the infusion of substitution fluid upstream the dialyzer.

The estimated plasma water concentration in HDF pre-dilution and HF pre-dilution modes is a function of the blood flow rate $Q_b$ and of the infusion flow rate $Q_{inf}$. Furthermore, it is also function of the dialyzable blood water fraction for the selected substance (calculated based on hematocrit—Hct—and cell water fraction) and of the plasma water concentration in blood from patient (i.e. upstream the pre-dilution infusion point); the estimated plasma water concentration is also function of the infusion fluid concentration of the same substance.

Note that, in the specific formula, the estimated plasma water concentration is adjusted by a respective (preferably, but not necessarily, fixed) adjusting factor. Numerical values can be, e.g. 0.95 or 1.05, but other values may be used (generally depending on the protein content, or charge of ions).

More in detail, the adjusting factor is function of the charged plasma proteins, and particularly of the Donnan factor. In HD, HDF post-dilution and HF post-dilution modes, the adjusting factor is the Donnan factor $\alpha$ or its reciprocal $\alpha^{-1}$. In HDF pre-dilution and HF pre-dilution modes, the adjusting factor should take into consideration the reduction of total protein concentration due to pre-dilution infusion. Therefore, the adjusting factor is in this latter case function of the diluted protein concentration affected by blood flow $Q_b$, infusion flow $Q_{inf}$, and red cell fraction of blood Hct (see e.g. equation (14)).

The adjustment contribution term is an algebraic sum of a plurality of components, a first component being function of the difference, in particular weighted difference, in concentration of at least a substance in the dialysis fluid and the same substance in the blood plasma, the second component being function of the difference, in particular weighted difference, in concentration of at least a second substance in the dialysis fluid and the same second substance in the blood plasma, the third component being function of the difference, in particular weighted difference, in concentration of at least a third substance in the dialysis fluid and the same third substance in the blood plasma, optionally the fourth component being function of the difference, in particular a weighted difference, in concentration of at least a fourth substance in the dialysis fluid and the same fourth substance in the blood plasma, the fifth component depends on at least a ratio between one flow rate, in particular the dialysate flow rate at the outlet of the secondary chamber 4, and an efficiency parameter of the filtration unit 2, in particular a clearance of the filtration unit 2, optionally the urea clearance.

The substance may be chosen in the group including bicarbonate anions ($HCO_3^-$), acetate anions ($CH_3COO^-$), citrate anions ($C_6H_5O_7^{3-}$), and potassium ions ($K^+$), but additionally also lactate.

Again, in case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion. Therefore, the difference above mentioned is a difference between a diluted blood concentration and the concentration in the dialysis fluid of the same substance.

The above general consideration is reflected in specific and non-limiting implementing formulas which allow, when the plasma conductivity is known, to determine the precise set point for sodium concentration in the dialysis fluid for running an isotonic, isonatric or isonatrikalemic treatment.

Of course, different formulas including one or more of the general principles/substances above stated may be alternatively used.

Isotonic Dialysis

In order to obtain a dialysis fluid sodium implementing isotonic dialysis, i.e. $c_{di,Na,set,isotonic}$, an adjustment factor $c_{di,Na,isotonic,adj}$ needs to be applied to make the dialysis fluid matching the tonicity of the plasma:

$$c_{di,Na,set,isotonic} = c_{di,Na,K_{p,pre}} + c_{di,Na,isotonic,adj} \quad (29)$$

Isotonic Dialysis—HD Treatment Mode

In case of HD treatment mode:

$$c_{di,Na,isotonic,adj} = \quad (30)$$
$$-\frac{1}{M_{K_{NaCl}}}\Bigg((M_{K_{NaHCO_3}} - M_{K_{NaCl}})\Big(\frac{1}{\alpha}*c_{pw,HCO_3} - c_{di,HCO_3}\Big) +$$
$$(M_{K_{NaAc}} - M_{K_{NaCl}})\Big(\frac{1}{\alpha}*c_{pw,Ac} - c_{di,Ac}\Big) + +$$
$$(M_{K_{KCl}} - M_{K_{NaCl}})(\alpha*c_{pw,K} - c_{di,K}) + \frac{Q_{do}}{K_u}(K_{rest1} + K_{rest2})\Bigg)$$

or where the adjustment factor also takes care of citrate according to the following relationship:

$$c_{di,Na,isotonic,adj} = \quad (31)$$
$$-\frac{1}{M_{K_{NaCl}}}\Bigg((M_{K_{NaHCO_3}} - M_{K_{NaCl}})\Big(\frac{1}{\alpha}*c_{pw,HCO_3} - c_{di,HCO_3}\Big) +$$
$$(M_{K_{NaAc}} - M_{K_{NaCl}})\Big(\frac{1}{\alpha}*c_{pw,Ac} - c_{di,Ac}\Big) + + (M_{K_{KCl}} - M_{K_{NaCl}})$$
$$(\alpha*c_{pw,K} - c_{di,K}) + + \frac{K_{b_{Cit}}}{K_u}(M_{Na_3Cit} - 3M_{K_{NaCl}})$$
$$((0.167\alpha^{-3} + 0.125\alpha^{-2} + 0.706\alpha^{-1})*c_{pw,Na_3Cit} -$$
$$c_{di,Na_3Cit}) + + \frac{Q_{do}}{K_u}(K_{rest1} + K_{rest2})\Bigg)$$

$\kappa_{b_{Cit}}$ is the approximated clearance value for citrate. This clearance is calculated for the actual flow rates using a mass transfer value of $K_0A_{Cit}=0{,}212*K_0A_{Urea}$ in the corresponding $K_u$ formula.

FIG. 4 shows the conductivity values upstream and downstream the dialyzer after setting the fresh dialysis fluid sodium concentration for running an isotonic dialysis treatment.

It is worth to mention that the plasma conductivity might be also measured using conductivity steps and applying the methods described in publications n. EP 547025 and/or in EP 920877. This alternative or additional estimation of plasma conductivity may further improve the plasma conductivity estimation made with the previously described technique.

Factor k (namely, $k_{rest1}$, $k_{rest2}$, and $k_{rest3}$—see also the following formulas) defines the effect on the conductivity due to other components in the dialysis fluid different from the components already treated and included in the respective formula. Thus, the effect of salts containing calcium, magnesium, lactate, phosphate, and sulphate may have upon the conductivity. The effect created by these components is most often small, and does not vary considerably between the dialysis treatments.

Isotonic Dialysis—HDF Post-Dilution Treatment Mode

In case of HDF treatment mode post-dilution, the same equations (30), (31) as for HD treatment mode applies, but with the clearance $\kappa_u$ calculated for the HDF treatment case with the substitution flow rate taken into account (see equations (4-8)).

Isotonic Dialysis—HDF Pre-Dilution Treatment Mode

The equations for HDF pre-dilution are similar to HDF post, but we must take into account the dilution of the blood before it enters the dialyzer.

The dilution of the plasma water concentration of substance 1 in pre-dilution mode is described by equation (21) here-below reported for ease of comprehension:

$$c_{pw,bi} = \frac{Q_b \cdot f_i \cdot c_{pw,art} + Q_{inf} \cdot c_{inf}}{Q_b \cdot f_i + Q_{inf}} \quad (21)$$

The adjustment factor is calculated as follows:

$$c_{di,Na,isotonic,adj} = -\frac{1}{M_{\kappa_{NaCl}}}\left((M_{\kappa_{NaHCO_3}} - M_{\kappa_{NaCl}})\right. \quad (32)$$

$$\left(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\right)++$$

$$(M_{\kappa_{NaAc}} - M_{\kappa_{NaCl}})$$

$$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right)++$$

$$(M_{\kappa_{KCl}} - M_{\kappa_{NaCl}}) \cdot$$

$$\left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right)++$$

$$\frac{K_{b,Cit}}{K_u} \cdot (M_{\kappa_{Na_3Cit}} - M_{\kappa_{NaCl}})$$

$$\left((0.167\alpha_{bi}^{-3} + 0.125\alpha_{bi}^{-2} + 0.706\alpha_{bi}^{-1}) \cdot \cdot\right.$$

$$\frac{Q_b \cdot f_{Cit} \cdot c_{pw,artCit} + Q_{inf} \cdot c_{di,Cit}}{Q_b \cdot f_{Cit} + Q_{inf}} -$$

$$\left.c_{di,Na_3Cit}\right)\right)++\frac{Q_{do}}{K_u}(\kappa_{rest1} + \kappa_{rest2})$$

Isotonic Dialysis—HF Pre-Dilution Treatment Mode

The equations for HF pre-dilution are the same equations as HDF pre-dilution, but with the filtration unit clearance equal to dialysate flow rate at filtration unit outlet, i.e. $K_u = Q_{do}$.

Isotonic Dialysis—HF Post-Dilution Treatment Mode

The equations for HF post-dilution are the same equations as HD, but with the filtration unit clearance equal to dialysate flow rate at filtration unit outlet, i.e. $K_u = Q_{do}$.

Isonatric Dialysis

In order to obtain a dialysis fluid sodium implementing isonatric dialysis, i.e. $c_{di,Na,set,isoNa}$, an adjustment factor $c_{di,Na,isoNa,adj}$ needs to be applied to make the sodium concentration of dialysate out from the dialyzer matching the sodium concentration of dialysis fluid at the inlet of the dialyzer:

$$c_{di,Na,set,isoNa} = c_{di,Na,\kappa_p,pre} + c_{di,Na,isoNa,adj} \quad (33)$$

Isonatric Dialysis—HD Treatment Mode

In case of HD treatment mode:

$$c_{di,Na,isoNa,adj} = \quad (34)$$

$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right)+\right.$$

$$(M_{\kappa_{NaAc}} - M_{\kappa_{NaCl}})\left(\frac{1}{\alpha} * c_{pw,Ac} - c_{di,Ac}\right)++$$

$$\left.M_{\kappa_{KCl}}(\alpha * c_{pw,K} - c_{di,K}) + \frac{Q_{do}}{K_u}\kappa_{rest3}\right)$$

Where the adjustment factor also takes care of citrate, the adjustment factor is calculated according to the following relationship:

$$c_{di,Na,isoNa,adj} = \quad (35)$$

$$-\frac{1}{M_{\kappa_{NaCl}}}\left((M_{\kappa_{NaHCO_3}} - M_{\kappa_{NaCl}})\left(\frac{1}{\alpha} * c_{pw,HCO_3} - c_{di,HCO_3}\right)+\right.$$

$$(M_{\kappa_{NaAc}} - M_{\kappa_{NaCl}})\left(\frac{1}{\alpha} * c_{pw,Ac} - c_{di,Ac}\right)++$$

$$\frac{K_{b,Cit}}{K_u}(M_{\kappa_{Na_3Cit}} - 3M_{\kappa_{NaCl}})$$

$$((0.167\alpha^{-3} + 0.125\alpha^{-2} + 0.706\alpha^{-1}) * c_{pw,Na_3Cit} -$$

$$\left.c_{di,Na_3Cit})++M_{\kappa_{KCl}}(\alpha * c_{pw,K} - c_{di,K}) + \frac{Q_{do}}{K_u}\kappa_{rest3}\right)$$

For $K_{b_{Cit}}$ calculation see above.

Isonatric Dialysis—HDF Post-Dilution Treatment Mode

In case of HDF treatment mode post-dilution, the same equations as for HD treatment mode applies, but with the clearance $K_u$ calculated for the HDF treatment case with the substitution flow rate taken into account (see equations (4-8)).

Isonatric Dialysis—HDF Pre-Dilution Treatment Mode

The equations for HDF pre-dilution are similar to HDF post, but we must take into account the dilution of the blood before it enters the dialyzer.

The adjustment factor is calculated as follows:

$$c_{di,Na,isoNa,adj} = -\frac{1}{M_{\kappa_{NaCl}}}\left((M_{\kappa_{NaHCO_3}} - M_{\kappa_{NaCl}})\right. \quad (36)$$

$$\left(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\right)++$$

$$(M_{\kappa_{NaAc}} - M_{\kappa_{NaCl}})$$

$$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right)++$$

$$M_{\kappa_{KCl}} \cdot \left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right)++$$

$$\frac{K_{b,Cit}}{K_u} \cdot (M_{\kappa_{Na_3Cit}} - 3M_{\kappa_{NaCl}})$$

$$\left((0.167\alpha_{bi}^{-3} + 0.125\alpha_{bi}^{-2} + 0.706\alpha_{bi}^{-1}) \cdot \cdot\right.$$

$$\frac{Q_b \cdot f_{Cit} \cdot c_{pw,artCit} + Q_{inf} \cdot c_{di,Cit}}{Q_b \cdot f_{Cit} + Q_{inf}} -$$

$$\left.c_{di,Na_3Cit}\right)\right)++\frac{Q_{do}}{K_u}\kappa_{rest3}$$

Isonatric Dialysis—HDF Pre- and Post-Dilution Treatment Mode

It is also possible to handle combined pre and post treatment modes. The infusion flow $Q_{inf}$ is divided into two parts $Q_{inf,pre}$ and $Q_{inf,post}$, wherein $$Q_{inf} = Q_{inf,pre} + Q_{inf,post} \tag{37}$$

General formulas covers combinations and pure pre- and post-dilution as special cases. In this case the adjustment factor can be calculated as follows:

$$c_{di,Na,isoNa,adj} = -\frac{1}{M_{K_{NaCl}}}\Bigg((M_{K_{NaHCO_3}} - M_{K_{NaCl}}) \tag{38}$$

$$\left(\frac{1}{\alpha_{bi}} \cdot \frac{Q_b \cdot f_{HCO_3} \cdot c_{pw,artHCO_3} + Q_{inf,pre} \cdot c_{di,HCO_3}}{Q_b \cdot f_{HCO_3} + Q_{inf,pre}} - c_{di,HCO_3}\right) + + (M_{K_{NaAc}} - M_{K_{NaCl}})$$

$$\left(\frac{1}{\alpha_{bi}} \cdot \frac{Q_b \cdot f_{Ac} \cdot c_{pw,artAc} + Q_{inf,pre} \cdot c_{di,Ac}}{Q_b \cdot f_{Ac} + Q_{inf,pre}} - c_{di,Ac}\right) + +$$

$$M_{K_{KCl}} \cdot \left(\alpha_{bi} \cdot \frac{Q_b \cdot f_K \cdot c_{pw,artK} + Q_{inf,pre} \cdot c_{di,K}}{Q_b \cdot f_K + Q_{inf,pre}} - c_{di,K}\right) + +$$

$$\frac{K_{b,Cit}}{K_u} \cdot (M_{K_{Na_3Cit}} - 3M_{K_{NaCl}})$$

$$\left((0.167\alpha_{bi}^{-3} + 0.125\alpha_{bi}^{-2} + 0.706\alpha_{bi}^{-1}) \cdot \cdot\right.$$

$$\left.\frac{Q_b \cdot f_{Cit} \cdot c_{pw,artCit} + Q_{inf,pre} \cdot c_{di,Cit}}{Q_b \cdot f_{Cit} + Q_{inf,pre}} - c_{di,Na_3Cit}\right)\Bigg) + + \frac{Q_{do}}{K_u}(\kappa_{rest1} + \kappa_{rest2})$$

Together with $$c_{pw,bi} = \frac{Q_b \cdot f_i \cdot c_{pw,art} + Q_{inf,pre} \cdot c_{inf}}{Q_b \cdot f_i + Q_{inf,pre}} \tag{39}$$

$$c_{pi,bi_{initial\ protein}} = \frac{Q_b \cdot (1-Hct) \cdot c_{p,art_{initial\ protein}}}{Q_b \cdot (1-Hct) + Q_{inf,pre}} \tag{40}$$

$$\alpha_{bi} = 1.004 \cdot e^{-0.008 \cdot c_{pi,bi_{initial\ protein}}} \tag{41}$$

The used symbols meaning is clarified in the glossary section.

It is noted that if $Q_{inf,pre}=0$, the formula for HDF post-dilution are obtained.

Regarding clearance calculations $Q_{inf}=Q_{inf,pre}+Q_{inf,post}$ should remain to be used as it is the sum of infusions that passes the dialyzer together with the weight loss.

Of course, in HF the same technique may be used and the clearance is equal to the dialyzer outlet fluid flow.

Isonatric Dialysis—HF Pre-Dilution Treatment Mode

The equations for HF pre-dilution are the same equations as HDF pre-dilution, but with the filtration unit clearance equal to dialysate flow rate at filtration unit outlet, i.e. $K_u=Q_{do}$.

Isonatric Dialysis—HF Post-Dilution Treatment Mode

The equations for HF post-dilution are the same equations as HD, but with the filtration unit clearance equal to dialysate flow rate at filtration unit outlet, i.e. $K_u=Q_{do}$.

Isonatrikalemic Dialysis

In order to obtain a dialysis fluid sodium implementing isonatrikalemic dialysis, i.e. $c_{di,Na,set,isoNa+K}$, an adjustment factor $c_{di,Na,isoNa+K,adj}$ needs to be applied to make the sum of sodium and potassium concentrations of dialysate out from the dialyzer matching the corresponding sum of concentrations of dialysis fluid at the inlet of the dialyzer:

$$c_{di,Na,set,isoNa+K} = c_{di,Na,K_{pre}} + c_{di,Na,isoNa+K,adj} \tag{42}$$

Isonatrikalemic Dialysis—HD Treatment Mode

In case of HD treatment mode:

$$c_{di,Na,isoNa+K,adj} = \tag{43}$$

$$-\frac{1}{M_{K_{NaCl}}}\Bigg((M_{K_{NaHCO_3}} - M_{K_{NaCl}})\left(\frac{1}{\alpha} * c_{pw,HCO_3} - c_{di,HCO_3}\right) +$$

$$(M_{K_{NaAc}} - M_{K_{NaCl}})\left(\frac{1}{\alpha} * c_{pw,Ac} - c_{di,Ac}\right) + +$$

$$(M_{K_{KCl}} - M_{K_{NaCl}})(\alpha * c_{pw,K} - c_{di,K}) + \frac{Q_{do}}{K_u}\kappa_{rest3}\Bigg)$$

or where the adjustment factor also takes care of citrate according to the following relationship:

$$c_{di,Na,isoNa+K,adj} = \tag{44}$$

$$-\frac{1}{M_{K_{NaCl}}}\Bigg((M_{K_{NaHCO_3}} - M_{K_{NaCl}})\left(\frac{1}{\alpha} * c_{pw,HCO_3} - c_{di,HCO_3}\right) +$$

$$(M_{K_{NaAc}} - M_{K_{NaCl}})\left(\frac{1}{\alpha} * c_{pw,Ac} - c_{di,Ac}\right) + +$$

$$\frac{K_{b,Cit}}{K_u}(M_{K_{Na_3Cit}} - 3M_{K_{NaCl}})$$

$$((0.167\alpha^{-3} + 0.125^{-2} + 0.706\alpha^{-1}) * c_{pw,Na_3Cit} - c_{di,Na_3Cit}) + +$$

$$(M_{K_{KCl}} - M_{K_{NaCl}})(\alpha * c_{pw,K} - c_{di,K}) + \frac{Q_{do}}{K_u}\kappa_{rest3}\Bigg)$$

For $K_{b_{Cit}}$ calculation see above.

Isonatrikalemic Dialysis—HDF Post-Dilution Treatment Mode

In case of HDF treatment mode post-dilution, the same equations (43), (44) as for HD treatment mode applies, but with the clearance $K_u$ calculated for the HDF treatment case with the substitution flow rate taken into account (see equation (4-8)).

Isonatrikalemic Dialysis—HDF Pre-Dilution Treatment Mode

The equations for HDF pre-dilution are similar to HDF post, but we must take into account the dilution of the blood before it enters the dialyzer.

The adjustment factor is calculated as follows:

$$c_{di,Na,isoNaK,adj} = -\frac{1}{M_{K_{NaCl}}}\Bigg((M_{K_{NaHCO_3}} - M_{K_{NaCl}}) \tag{45}$$

$$\left(\frac{1}{\alpha_{bi}} \cdot \frac{Q_b \cdot f_{HCO_3} \cdot c_{pw,artHCO_3} + Q_{inf} \cdot c_{di,HCO_3}}{Q_b \cdot f_{HCO_3} + Q_{inf}} - c_{di,HCO_3}\right) + +$$

$$(M_{K_{NaAc}} - M_{K_{NaCl}})$$

$$\left(\frac{1}{\alpha_{bi}} \cdot \frac{Q_b \cdot f_{Ac} \cdot c_{pw,artAc} + Q_{inf} \cdot c_{di,Ac}}{Q_b \cdot f_{Ac} + Q_{inf}} - c_{di,Ac}\right) + +$$

$$(M_{K_{KCl}} - M_{K_{NaCl}}) \cdot$$

$$\left(\alpha_{bi} \cdot \frac{Q_b \cdot f_K \cdot c_{pw,artK} + Q_{inf} \cdot c_{di,K}}{Q_b \cdot f_K + Q_{inf}} - c_{di,K}\right) + +$$

$$\frac{K_{b,Cit}}{K_u} \cdot (M_{K_{Na_3Cit}} - 3M_{K_{NaCl}})$$

$$\left((0.167\alpha_{bi}^{-3} + 0.125\alpha_{bi}^{-2} + 0.706\alpha_{bi}^{-1}) \cdot \cdot\right.$$

-continued $$\frac{Q_b \cdot f_{Cit} \cdot c_{pw,artCit} + Q_{inf} \cdot c_{di,Cit}}{Q_b \cdot f_{Cit} + Q_{inf}} -$$

$$c_{di,Na_3Cit}\bigg)\bigg) + + \frac{Q_{do}}{K_u} K_{rest3}$$

Isonatrikalemic Dialysis—HF Pre-Dilution Treatment Mode

The equations for HF pre-dilution are the same equations as HDF pre-dilution, but with the filtration unit clearance equal to dialysate flow rate at filtration unit outlet, i.e. $K_u = Q_{do}$.

Isonatrikalemic Dialysis—HF Post-Dilution Treatment Mode

The equations for HF post-dilution are the same equations as HD, but with the filtration unit clearance equal to dialysate flow rate at filtration unit outlet, i.e. $K_u = Q_{do}$.

Dialysis Fluid Sodium Concentration During Treatment

Once the set point for sodium is calculated, the control unit drives the regulating means 10 for regulating the conductivity or the concentration of the substance in the fresh dialysis fluid and sets the parameter value for the dialysis fluid in the dialysis fluid supply line 8 at the calculated set point.

With respect to all the above sodium concentrations set for the isotonic, isonatric, and isonatrikalemic dialysis treatments, it is worth to note that the calculated and proposed concentration shall be within the isotonic sodium set user limits.

These limits may be chosen by the operator before isotonic dialysis start, within the following limits:

For instance, the absolute safety range (e.g. 120÷160 mmol/l);

the sodium range corresponding to the conductivity allowed range of the machine (e.g. 12÷16 mS/cm), given the used bag and the prescribed bicarbonate.

Generally, if the calculated sodium concentration value for the set falls outside the user range, the isotonic dialysis should be de-activated and/or at least a warning is given to the operator.

Hence, the output of the described task is a new value for sodium concentration in the dialysis fluid, which is used as sodium set value for the regulating means (i.e. concentrate dosing system) when isotonic dialysis is active.

Advantageously, the changes to sodium set value will not affect the bicarbonate set value, which remains the one set by the operator.

In order to have a further degree of freedom for sodium set adjustment, before applying it to the remainder of the treatment, an additional offset may also be applied. This additional offset can be different depending on the isotonic dialysis type.

After the application of sodium adjustments above described, the inlet conductivity correspondent to the fresh dialysis fluid sodium concentration determined with corresponding equations shall then be kept constant throughout the remainder of the treatment.

After the setting of the sodium set point for the isotonic treatment, the plasma conductivity may be further calculated/monitored using common procedures, such as those described in patents EP 547025 or in EP 920877 to monitor PC throughout the treatment.

Compensation for Unwanted Sodium Transfer

To maintain the patient's sodium balance during the dialysis treatment, the calculated sodium set value must be adjusted to compensate for any additional unwanted sodium load to the patient.

During the identification phase (i.e. plasma conductivity initial estimate), the sodium setting is likely to be too high, leading to unwanted sodium load. The time for this estimation may slightly vary, but as an average is about 15 minutes; accordingly, the magnitude of the error is in the range of 5 mmol/l (of course varying with how well the expected plasma conductivity matches the actual plasma conductivity, as well as the magnitude of the isotonic adjustment).

Moreover, if common procedures such as those described in patents EP 547025 or in EP 920877 to monitor plasma conductivity throughout the treatment are used (e.g. Diascan measurements), a sodium transfer will result from the conductivity steps (10 mmol/L for 120 s for example). This sodium transfer can be either in the positive or negative direction.

Such unwanted transfers may need to be compensated for in order to maintain the desired sodium balance during the treatment.

In order to make the treatment truly isotonic (or better, to minimize the tonicity gradient between the dialysis fluid and the blood), such unwanted transfers need to be compensated for as a whole.

In order to manage multiple deviations e.g. from Diascan measurements, the compensation may be implemented by integrating some, or possibly any deviation from the intended sodium set point (i.e. the sodium concentration that is set after the measurement of the isoconductivity, $c_{di,Na,set}$) and then compensate for this over the remaining time of treatment (T−t, where T is the total treatment time and t is the elapsed treatment time).

The applied compensated sodium concentration set point may be calculated according to the following formula:

$$c_{di,Na,set,compensated} = \qquad (46)$$

$$c_{di,Na,set} + \sum_i \frac{1}{T - \tau_i} \int_{t_i}^{t_i + \Delta t_i} (c_{di,Na,set} - c_{di,Na,actual,i}) dt$$

where $C_{di,Na,set}$ is the sodium setpoint calculated by the described algorithm (in other terms $c_{di,Na,set}$ may be $c_{di,Na,set,isotonic}$, $c_{di,Na,set,isoNa}$, $c_{di,Na,set,isoNa+K}$; cf. formulas 8, 10, and 12), $c_{di,Na,actual}$ is the actual dialysis fluid sodium concentration set point used during the treatment at the time an additional compensation is to be applied for (note that $c_{di,Na,actual}$ may deviate from $c_{di,Na,set}$, due to both the initial estimation of isoconductivity and/or the plasma conductivity monitoring procedures, e.g. Diascan steps).

The compensation may be or may be not activated once $c_{di,Na,set}$ has been calculated (for example about 15 minutes after treatment start, i.e. at the end of the identification phase), and may (or may not) take the past history into account so that any sodium transfer during the isoconductivity identification phase is also compensated.

The compensation may be applied after every sodium i-th deviation, i.e., when sodium is equal to $c_{di,Na,actual,i}$ for a duration of $\Delta t_i$. Hence, also aborted Diascan measures may be taken into account (in this case, $\Delta t$ may be lower than the forecast conductivity step).

Instead of applying a single compensation factor for each deviation, a potential alternative is to apply an integral controller, which, on the basis of the current error on applied sodium set vs. isotonic/isonatric/isonatrikalemic set found and on the time still available, applies automatically a corrected set.

The invention claimed is:

1. An apparatus for extracorporeal blood treatment comprising:
   a filtration unit having a primary chamber and a secondary chamber separated by a semi-permeable membrane;
   a blood withdrawal line connected to an inlet of the primary chamber;
   a blood return line connected to an outlet of the primary chamber, said blood lines being configured for connection to a patient cardiovascular system;
   a dialysis supply line including at least an infusion line connected to said blood circuit;
   a dialysis effluent line connected to an outlet of the secondary chamber;
   a preparation device for preparing a dialysis fluid connected to said supply line and comprising a regulator for regulating the composition of the dialysis fluid; and
   a control unit in operable communication with the regulator, the control unit configured to:
      run at least one of a hemofiltration (HF) treatment or a hemodiafiltration (HDF) treatment, each of said treatments including an infusion of substitution fluid through said infusion line,
      receive a value representative of a first parameter, the first parameter being chosen from the group consisting of a plasma conductivity, a plasma conductivity-related parameter, a concentration of at least a substance in the blood, and a concentration-related parameter of at least a substance in the blood,
      set a second parameter value for the dialysis fluid in the dialysis supply line at a set point, said second parameter of the dialysis fluid being at least one chosen from a group consisting of a conductivity of the dialysis fluid, a conductivity-related parameter of the dialysis fluid, a concentration of at least a substance in the dialysis fluid, and a concentration-related parameter of at least a substance in the dialysis fluid,
      calculate, as a sub-step of setting the second parameter value in the dialysis fluid, the second parameter value as a function of a main contribution term based on the first parameter and as a function of an adjustment contribution term based on a concentration of at least a substance in the dialysis fluid chosen from the group consisting of bicarbonate, potassium, acetate, lactate, citrate, magnesium, calcium, sulphate, and phosphate, wherein the adjustment contribution term includes an amount with which to adjust a sodium concentration set point for an isoconductive dialysis to provide a sodium concentration set point needed for a treatment chosen from the group consisting of isotonic dialysis, isonatric dialysis and isonatrikalemic dialysis,
      receive a selection of (i) at least one treatment mode chosen from the group consisting of a hemofiltration treatment mode or a hemodiafiltration treatment mode, and (ii) at least one treatment chosen from the group consisting of isotonic dialysis, isonatric dialysis and isonatrikalemic dialysis, and
      drive the regulator as a function of the calculated plasma conductivity, the chosen treatment mode and the chosen treatment to set either a desired dialysis fluid inlet conductivity or a desired dialysis fluid inlet sodium concentration.

2. Apparatus according to claim 1, wherein the control unit is configured to calculate the adjustment contribution term based on the concentration of two or more substances in the dialysis fluid chosen from the group consisting of bicarbonate, potassium, acetate, lactate, citrate, magnesium, calcium, sulphate, and phosphate.

3. Apparatus according to claim 1, wherein the control unit is configured to calculate the adjustment contribution term as a function of the weighted difference in concentration of at least a substance in the dialysis fluid and the same substance in the plasma, said substance being chosen from the group consisting of bicarbonate, potassium, acetate, lactate and citrate.

4. Apparatus according to claim 1, wherein the blood parameter is the plasma conductivity, or the concentration of at least a substance in the blood, and wherein the parameter of the dialysis fluid is the conductivity of the dialysis fluid, or the concentration of at least a substance in the dialysis fluid, said substance being sodium.

5. Apparatus according to claim 1, wherein the main contribution term is dimensionally a concentration of a substance in a fluid, and wherein the main contribution term is a dialysis fluid concentration of sodium at an isoconductive dialysis.

6. Apparatus according to claim 1, wherein the adjustment contribution term is the sodium concentration set point adjustment relative to the sodium concentration set point for the isoconductive dialysis, the adjustment contribution applied to the sodium concentration set point for the isoconductive dialysis provides a treatment that removes from, or adds to, the plasma a defined amount of at least a substance.

7. Apparatus according to claim 1, wherein the control unit drives the regulator for regulating the conductivity or the concentration of at least a substance in the dialysis fluid, the control unit setting the second parameter value for the dialysis fluid in the dialysis supply line at the calculated set point.

8. Apparatus according to claim 1, wherein the control unit is configured to calculate the adjustment contribution term as a function of the molar conductivities of at least two substances in the dialysis fluid chosen from the group consisting of sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$).

9. Apparatus according to claim 1, wherein the control unit is configured to calculate the adjustment contribution term as a function of a difference between a first molar conductivity of a substance chosen from the group consisting of sodium bicarbonate ($NaHCO_3$), sodium acetate ($NaCH_3COO$), trisodium citrate ($Na_3C_6H_5O_7$), sodium lactate ($NaC_3H_5O_3$), and potassium chloride (KCl), and a second molar conductivity of sodium chloride (NaCl).

10. Apparatus according to claim 1, wherein the control unit is configured to calculate the adjustment contribution term as a function of an estimated or measured plasma water concentration of at least a substance chosen from the group consisting of bicarbonate, potassium, acetate, lactate, and citrate, and
   wherein for HDF pre-dilution treatment and HF pre-dilution treatment, said estimated or measured plasma water concentration is a diluted plasma concentration, the diluted plasma concentration being function of the blood flow rate and of the infusion flow rate.

11. Apparatus according to claim 1, wherein the control unit is configured to calculate the adjustment contribution term as an algebraic sum of at least two components, a first component being function of the difference in concentration of at least a substance in the dialysis fluid and the same substance in the blood plasma, the second component being function of the weighted difference in concentration of at least a second substance in the dialysis fluid and the same second substance in the blood plasma, and wherein said substance is chosen from the group consisting of bicarbonate anions ($HCO_3^-$), acetate anions ($CH_3COO^-$), citrate anions ($C_6H_5O_7^{3-}$), and potassium ions ($K^+$).

12. Apparatus according to claim 1, wherein the control unit is configured to calculate the adjustment contribution term as an algebraic sum of at least two components, a first component being function of a concentration of at least a substance in the dialysis fluid and/or in the blood plasma, a second component being function of a concentration of at least a second substance in the dialysis fluid and/or in the blood plasma, and wherein said substance is chosen from the group consisting of bicarbonate anions ($HCO_3^-$), acetate anions ($CH_3COO^-$), citrate anions ($C_6H_5O_7^{3-}$), and potassium ions ($K^+$).

13. Apparatus according to claim 1, wherein the control unit is configured to calculate the adjustment contribution term as a function of at least a ratio between the dialysate flow rate at the outlet of the secondary chamber and an efficiency parameter of the filtration unit.

14. Apparatus according to claim 13, wherein the control unit is configured to calculate the plasma conductivity as a function of the dialysate flow rate at the outlet of the secondary chamber and the blood flow rate in the blood lines.

15. Apparatus according to claim 1, wherein the control unit is configured to calculate the plasma conductivity as a function of at least an efficiency parameter of the filtration unit.

16. Apparatus according to claim 1, wherein the control unit is configured to calculate the plasma conductivity as a function of at least an initial conductivity of the dialysate and of at least a conductivity of the dialysis fluid in the dialysis supply line.

17. The apparatus according to claim 1, wherein the regulator includes a pump.

18. An apparatus for extracorporeal blood treatment comprising:
   a filtration unit having a primary chamber and a secondary chamber separated by a semi-permeable membrane;
   a blood withdrawal line connected to an inlet of the primary chamber;
   a blood return line connected to an outlet of the primary chamber, said blood lines being configured for connection to a patient cardiovascular system;
   a dialysis supply line connected to an inlet of the secondary chamber;
   a dialysis effluent line connected to an outlet of the secondary chamber;
   a preparation device for preparing a dialysis fluid connected to said supply line and comprising a regulator for regulating the composition of the dialysis fluid; and
   a control unit in operable communication with the regulator, the control unit configured to:
      receive a value for a first parameter, the first parameter being chosen from the group consisting of a plasma conductivity, and a concentration of at least sodium in the blood,
      set a second parameter value for the dialysis fluid in the dialysis supply line at a set point, said second parameter of the dialysis fluid being at least one chosen from a group consisting of a conductivity of the dialysis fluid and a concentration of at least a substance in the dialysis fluid,
      calculate, as a sub-step of setting the second parameter value in the dialysis fluid, the second parameter value as a function of a main contribution term based on the first parameter and as a function of an adjustment contribution term based on a concentration of at least a substance in the dialysis fluid chosen from a group consisting of bicarbonate, potassium, acetate, lactate, citrate, magnesium, calcium, sulphate, and phosphate, wherein the main contribution term includes a dialysis fluid concentration of sodium for an isoconductive dialysis, wherein the adjustment contribution term is the sodium concentration set point adjustment to the sodium concentration set point for the isoconductive dialysis, the adjustment contribution applied to the sodium concentration set point for the isoconductive dialysis providing a treatment chosen from a group consisting of isotonic dialysis, isonatremic dialysis, isonatrikalemic dialysis and a treatment that removes from, or adds to, the plasma a defined amount of at least a substance,
      receive a selection of (i) at least one treatment mode chosen from the group consisting of a hemofiltration treatment mode or a hemodiafiltration treatment mode, and (ii) at least one treatment chosen from the group consisting of isotonic dialysis, isonatric dialysis and isonatrikalemic dialysis, and
      drive the regulator as a function of the calculated plasma conductivity, the chosen treatment mode and the chosen treatment to set either a desired dialysis fluid inlet conductivity or a desired dialysis fluid inlet sodium concentration.

19. Apparatus according to claim 18, wherein the control unit is configured to calculate the adjustment contribution term as a function of the molar conductivities of at least three substances in the dialysis fluid chosen from the group consisting of sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$), and wherein the control unit is configured to drive the regulator for regulating the conductivity or the concentration of at least a substance in the dialysis fluid, the control unit setting the second parameter value for the dialysis fluid in the dialysis supply line at the calculated set point.

20. The apparatus according to claim 18, wherein the regulator includes a pump.

21. An apparatus for extracorporeal blood treatment comprising:
   a filtration unit having a primary chamber and a secondary chamber separated by a semi-permeable membrane;
   a blood withdrawal line connected to an inlet of the primary chamber;
   a blood return line connected to an outlet of the primary chamber, said blood lines being configured for connection to a patient cardiovascular system;
   a dialysis supply line including at least an infusion line connected to an inlet of the secondary chamber;
   a dialysis effluent line connected to an outlet of the secondary chamber;
   a preparation device for preparing a dialysis fluid connected to said supply line and comprising a regulator for regulating the composition of the dialysis fluid;
   a control unit in operable communication with the regulator, the control unit configured to:

run at least a hemofiltration treatment or a hemodiafiltration treatment, each of said treatment including an infusion of substitution fluid through said infusion line, receive a value representative of a first parameter, the first parameter being chosen from the group including a plasma conductivity, a plasma conductivity-related parameter, a concentration of at least a substance in the blood, a concentration-related parameter of at least a substance in the blood, set a second parameter value for the dialysis fluid in the dialysis supply line at a set point, said second parameter of the dialysis fluid being at least one chosen in a group including a conductivity of the dialysis fluid, a conductivity-related parameter of the dialysis fluid, a concentration of at least a substance in the dialysis fluid and a concentration-related parameter of at least a substance in the dialysis fluid, calculate, as a sub-step of setting the second parameter value in the dialysis fluid, the second parameter value as a function of a main contribution term based on the first parameter and as a function of an adjustment contribution term based on a concentration of at least a substance in the dialysis fluid chosen from a group consisting of bicarbonate, potassium, acetate, lactate, citrate, magnesium, calcium, sulphate, and phosphate, wherein the main contribution term is a dialysis fluid concentration of sodium at an isoconductive dialysis, calculate the adjustment contribution term as a function of a weighted difference in concentration of at least a substance in the dialysis fluid and the same substance in the plasma, said substance being chosen from the group consisting of bicarbonate, potassium, acetate, lactate and citrate, wherein the adjustment contribution applied to the sodium concentration set point for the isoconductive dialysis provides a sodium concentration set point needed for a treatment chosen from the group consisting of isotonic dialysis, isonatric dialysis and isonatrikalemic dialysis, receive a selection of: (i) at least one treatment mode chosen from the group consisting of hemofiltration treatment mode or hemodiafiltration treatment mode, and (ii) at least one treatment chosen from the group consisting of isotonic dialysis, isonatric dialysis and isonatrikalemic dialysis, and drive the regulator as a function of the calculated plasma conductivity, the chosen treatment mode and the chosen treatment to set either a desired dialysis fluid inlet conductivity or a desired dialysis fluid inlet sodium concentration.

22. The apparatus according to claim 21, wherein the regulator includes a pump.

* * * * *